(12) United States Patent
Araki et al.

(10) Patent No.: US 8,008,484 B2
(45) Date of Patent: Aug. 30, 2011

(54) USE OF SULFONANILIDES AS AGRICULTURAL AND HORTICULTURAL FUNGICIDE

(75) Inventors: Koichi Araki, Ushiku (JP); Sachio Kudo, Tsukuba (JP); Yoshitaka Sato, Tsukuba (JP); Masahito Ito, Ushiku (JP); Takuya Gomibuchi, Tsukuba (JP); Yasuo Araki, Kaminokawa-machi (JP); Tetsuya Inuta, Oyama (JP); Keiji Endo, Ami-machi (JP); Shinichi Shirakura, Oyama (JP); Shin Nakamura, Oyama (JP)

(73) Assignee: Bayer CropScience AG (DE)

( * ) Notice: Subject to any disclaimer, the term of this patent is extended or adjusted under 35 U.S.C. 154(b) by 0 days.

(21) Appl. No.: 11/632,832

(22) PCT Filed: Jul. 21, 2005

(86) PCT No.: PCT/EP2005/007948

§ 371 (c)(1),
(2), (4) Date: Mar. 19, 2007

(87) PCT Pub. No.: WO2006/008159

PCT Pub. Date: Jan. 26, 2006

(65) Prior Publication Data

US 2007/0219199 A1   Sep. 20, 2007

(30) Foreign Application Priority Data

Jul. 23, 2004 (JP) ................................ 2004-216399
Mar. 15, 2005 (JP) ................................ 2005-073005

(51) Int. Cl.
C07D 251/20 (2006.01)
C07D 251/24 (2006.01)

(52) U.S. Cl. ...................... 544/217; 544/219
(58) Field of Classification Search ................ 544/217, 544/219

See application file for complete search history.

(56) References Cited

U.S. PATENT DOCUMENTS

| | | | | |
|---|---|---|---|---|
| 5,885,935 | A * | 3/1999 | Gates et al. ................ | 504/230 |
| 6,458,748 | B1 * | 10/2002 | Yoshimura et al. ......... | 504/243 |
| 7,482,308 | B2 | 1/2009 | Araki et al. | |
| 7,829,703 | B2 | 11/2010 | Araki et al. | |
| 7,855,165 | B2 | 12/2010 | Endo et al. | |
| 2007/0167328 | A1 | 7/2007 | Endo et al. | |
| 2007/0197390 | A1 * | 8/2007 | Araki et al. ................ | 504/209 |
| 2009/0062536 | A1 | 3/2009 | Araki et al. | |
| 2009/0305894 | A1 | 12/2009 | Araki et al. | |
| 2010/0323896 | A1 | 12/2010 | Araki et al. | |

FOREIGN PATENT DOCUMENTS

| | | |
|---|---|---|
| DE | 10 2008 037 6 | 2/2010 |
| EP | 1101760 | 5/2001 |
| JP | 1989-217787 | 6/1989 |
| JP | 11-060562 | 2/1999 |
| JP | 1999-226160 | 3/1999 |
| JP | 2000-44546 | 2/2000 |
| JP | 2000/63360 | 2/2000 |
| JP | 2000/281513 | 10/2000 |
| JP | 2002-512998 | 5/2002 |
| JP | 2004/292417 | 10/2004 |
| JP | 2006-56870 | 3/2006 |
| JP | 2006-56871 | 3/2006 |
| JP | 2007-106745 | 4/2007 |
| WO | WO 93/09099 | 5/1993 |
| WO | WO 96/41799 | 12/1996 |
| WO | 2005/096818 | 10/2005 |
| WO | 2006/008159 | 1/2006 |
| WO | 2007-031208 | 3/2007 |
| WO | 2007/079965 | 7/2007 |
| WO | 2008/101595 | 8/2008 |
| WO | 2009/024251 | 2/2009 |
| WO | 2010/017921 | 2/2010 |
| WO | 2010/017922 | 2/2010 |
| WO | 2010/017923 | 2/2010 |
| WO | 2010/017924 | 2/2010 |
| WO | 2010/017925 | 2/2010 |
| WO | 2010/017926 | 2/2010 |
| WO | 2010/017927 | 2/2010 |
| WO | 2010/017928 | 2/2010 |
| WO | 2010/017929 | 2/2010 |
| WO | 2010/017930 | 2/2010 |
| WO | 2010/017931 | 2/2010 |

OTHER PUBLICATIONS

International Preliminary Report on Patentability for PCT/EP2005/002952.
International Search Report for PCT/EP2005/002952.
International Search Report for PCT/EP2008/006295.
El-Kerdawy et al., "Synthesis of Certain Substituted Pyrimidines as Potential Schisomicidal Agents", J. Heterocyclic Chem., 26, 913-915 (1989).

\* cited by examiner

*Primary Examiner* — Sharmila G. Landau
*Assistant Examiner* — Kortney L Klinkel
(74) *Attorney, Agent, or Firm* — Frommer Lawrence & Haug LLP

(57) ABSTRACT

Compounds of the formula (I), wherein Z represents $C-R^7$ or N, and $R^5$ represents alkyl that may be optionally substituted, alkenyl, alkynyl, cycloalkyl or alkoxycarbonylamino, are useful as agricultural and horticultural fungicides.

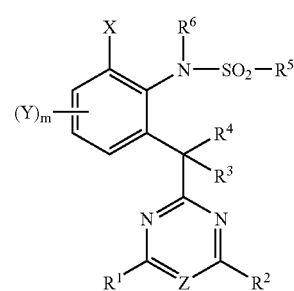

(I)

8 Claims, No Drawings

USE OF SULFONANILIDES AS AGRICULTURAL AND HORTICULTURAL FUNGICIDE

The present invention relates to a use of sulfonanilides as agricultural and horticultural fungicide, to novel sulfonanilides and to processes for their preparation.

It has been already known that some kinds of sulfonanilides show an action as herbicide (cf. for example, PCT International Laid-open Pamphlet WO 93/9099, PCT International Laid-open Pamphlet WO 96/41799, Japanese Laid-open Patent Publication No. 60562/1999, Japanese Laid-open Patent Publication No. 2000-44546, Japanese Laid-open Patent Publication No. 2000-63360).

It has now been found that a group of sulfonanilides of the following formulae (I) have fungicidal activities;

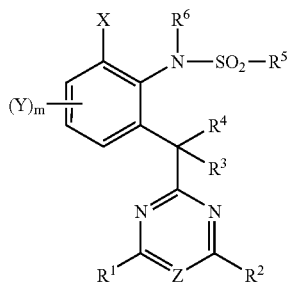

wherein

X represents hydrogen, halogen, alkyl, alkoxycarbonyl, acyl, dialkylaminocarbonyl, alkoxy, alkylsulfonyl, alkylsulfonyloxy, dialkylamino, haloalkyl, haloalkoxy, haloalkylthio, haloalkylsulfinyl, haloalkylsulfonyl, haloalkylsulfonyloxy, formyl, carboxy, cyano, nitro or phenoxy, Y represents halogen, alkyl that may be optionally substituted, alkoxyalkyl, alkoxycarbonyl, acyl, alkoxy, alkylthio, alkylsulfinyl, alkylsulfonyl, haloalkoxy, haloalkylthio, haloalkylsulfinyl, haloalkylsulfonyl, dialkylamino, cyano, amino or nitro, and 2 or 3 Y's may be identical or different each other in case that m is 2 or 3, Z represents C—$R^7$ or N, m represents an integer of 0 to 3, $R^1$ and $R^2$ each independently represents hydrogen, halogen, alkyl that may be optionally substituted, cycloalkyl, alkoxy, haloalkoxy, alkylthio or amino, $R^3$ and $R^4$ each independently represents hydrogen, halogen, alkyl, alkoxy that may be optionally substituted, alkylthio, alkylsulfonyl or amino, $R^3$ represents hydroxy and $R^4$ represents hydrogen or alkyl, or $R^3$ and $R^4$ together may form C=O with the carbon atom to which they are bonded, $R^5$ represents alkyl that may be optionally substituted, alkenyl, alkynyl, cycloalkyl or alkoxycarbonylamino, $R^6$ represents hydrogen, alkyl that may be optionally substituted, alkenyl, alkoxyalkyl, alkoxycarbonyl, acyl or group —$SO_2R^5$, and $R^7$ represents hydrogen or alkyl.

The sulfonanilides, represented by the following formula (IA) and included in the aforementioned formula (I) of the present invention, are novel compounds that were not described in the existing publications.

The formula

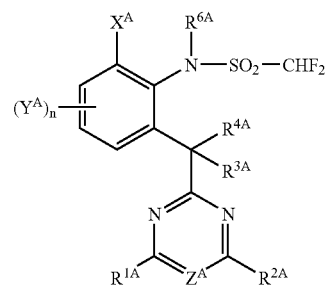

wherein $X^A$ represents hydrogen, halogen, alkyl, alkoxycarbonyl, acyl, dialkylaminocarbonyl, alkoxy, alkylsulfonyl, alkylsulfonyloxy, dialkylamino, haloalkoxy, haloalkylthio, haloalkylsulfinyl, haloalkylsulfonyl, haloalkylsulfonyloxy, formyl, carboxy, cyano, nitro or phenoxy, $Y^A$ represents halogen, alkyl that may be optionally substituted, alkoxyalkyl, alkoxycarbonyl, acyl, alkoxy, alkylsulfonyl, haloalkoxy, haloalkylthio, haloalkylsulfinyl, haloalkylsulfonyl, dialkylamino, cyano or nitro, and 2 or 3 $Y^A$'s may be identical or different each other in case that n is 2 or 3, $Z^A$ represents C—$R^{7A}$ or N, n represents an integer of 0-3, $R^{1A}$ and $R^{2A}$ each independently represents hydrogen, halogen, alkyl that may be optionally substituted, cycloalkyl, alkoxy, haloalkoxy or alkylthio, $R^{3A}$ and $R^{4A}$ each independently represents hydrogen, halogen, alkyl, alkoxy, alkylthio or alkylsulfonyl, $R^{3A}$ represents hydroxy and $R^{4A}$ represents hydrogen or alkyl, or $R^{3A}$ and $R^{4A}$ together may form C=O with the carbon atom to which they are bonded, $R^{6A}$ represents hydrogen, alkyl that may be optionally substituted, alkoxyalkyl, alkoxy-carbonyl, acyl or group —$SO_2R^{5A}$, $R^{5A}$ represents alkyl that may be optionally substituted, and $R^{7A}$ represents hydrogen or alkyl, with the exception of the following cases (T-1)-(T-3);

(T-1) the case in which $X^A$ represents alkyl, and n represents 0, (T-2) the case in which $X^A$ represents hydrogen, n represents 0, $Z^A$ represents CH, $R^{1A}$ and $R^{2A}$ represent methoxy, $R^{3A}$ represents hydroxy and $R^{4A}$ represents hydrogen, or $R^{3A}$ and $R^{4A}$ together form C=O with the carbon atom to which they are bonded, and $R^{6A}$ represents hydrogen, (T-3) the case in which $X^A$ represents halogen, n represents 0, $Z^A$ represents CH or N, $R^{1A}$ and $R^{2A}$ represent methoxy, $R^{3A}$ and $R^{4A}$ represent hydrogen, $R^{3A}$ represents hydroxy and $R^{4A}$ represents hydrogen, or $R^{3A}$ and $R^{4A}$ together form C=O with the carbon atom to which they are bonded, and $R^{6A}$ represents hydrogen.

The compounds of the formula (IA) can be obtained, similarly to the compounds of the formula (I) known from PCT International Laid-open Pamphlet WO 93/9099, PCT International Laid-open Pamphlet WO 96/41799, Japanese Laid-open Patent Publication No. 60562/1999, Japanese Laid-open Patent Publication No. 2000-44546, by a process in which a) in case that $R^{6A}$ represents hydrogen or difluoromethanesulfonyl:

compounds of the formula (II)

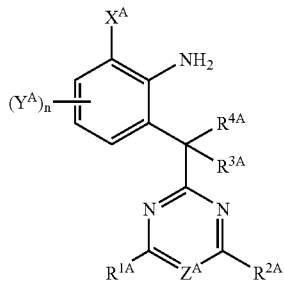

(II)

wherein $X^A, Y^A, Z^A, n, R^{1A}, R^{2A}, R^{3A}$ and $R^{4A}$ have the same definition as aforementioned, are reacted with difluoromethanesulfonyl chloride in the presence of innert solvents, and if appropriate, in the presence of an acid binder, or, b) In case that $R^{6A}$ represents alkyl that may be optionally substituted, alkoxyalkyl, acyl, alkoxycarbonyl or group $-SO_2R^{5A}$:

compounds of the formula (IAb)

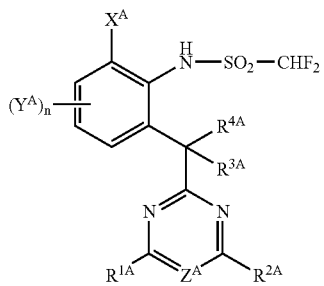

(IAb)

wherein $X^A, Y^A, Z^A, n, R^{1A}, R^{2A}, R^{3A}$ and $R^{4A}$ have the same definition as aforementioned, are reacted with compounds of the formula (III)

$R^{6A}-L^b$ (III)

wherein $R^{6A}$ represents alkyl that may be optionally substituted, alkoxyalkyl, acyl, alkoxycarbonyl or group $-SO_2R^{5A}$ $L^b$ represents halogen, in the presence of innert solvents, and if appropriate, in the presence of an acid binder, or, c) In case that $R^{3A}$ represents hydrogen and $R^{4A}$ represents hydrogen or alkyl:

compounds of the formula (IAc)

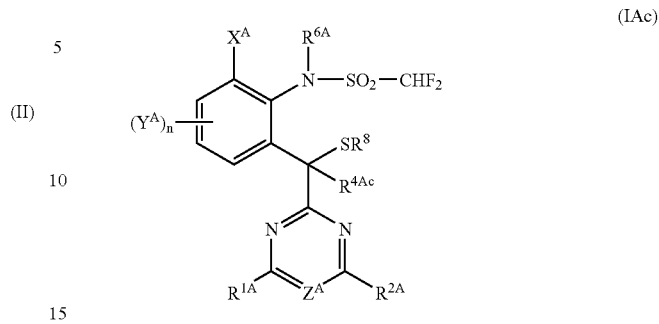

(IAc)

wherein $R^{4Ac}$ represents hydrogen or alkyl, $R^8$ represents alkyl, $X^A, Y^A, Z^A, n, R^{1A}, R^{2A}$ and $R^{6A}$ have the same definition as aforementioned, are reacted with a reducing agent in the presence of inner solvents, or, d) In case that $R^{3A}$ and $R^{4A}$ together form C=O with the carbon atom to which they are bonded: compounds of the formula (IAd)

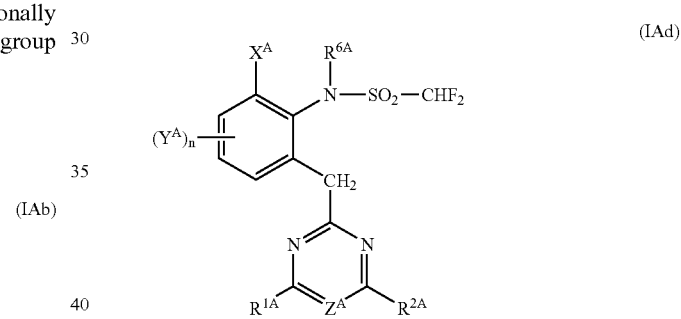

(IAd)

wherein $X^A, Y^A, Z^A, n, R^{1A}, R^{2A}$ and $R^{6A}$ have the same definition as aforementioned, are reacted with an oxidizing agent in the innert solvents, and if appropriate, in the presence of an acid catalyst, or, e) In case that $R^{3A}$ represents hydroxy and $R^{4A}$ represents alkyl:

compounds of the formula (IAe)

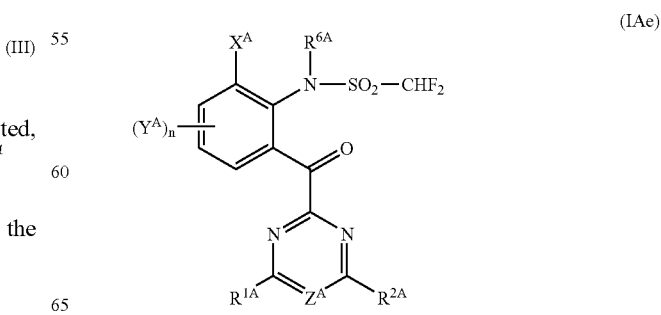

(IAe)

wherein
$X^A$, $Y^A$, $Z^A$, n, $R^{1A}$, $R^{2A}$ and $R^{6A}$ have the same definition as aforementioned,
are reacted with compounds of the formula (IV)

$$R^{4Ae}-Mg-L^e \quad (IV)$$

wherein
$R^{4Ae}$ represents alkyl,
$L^e$ represents halogen,
in the presence of innert solvents,
or,
f) in case that $R^{3A}$ represents hydroxy and $R^{4A}$ represents hydrogen:
compounds of the afore-mentioned formula (IAe) are reacted with an alkaline metal hydride complex compound or borane complex in the presence of innert solvents,
or,
g) in case that $R^{3A}$ represents hydrogen and $R^{4A}$ represents hydrogen or alkyl:
compounds of the formula (IAg)

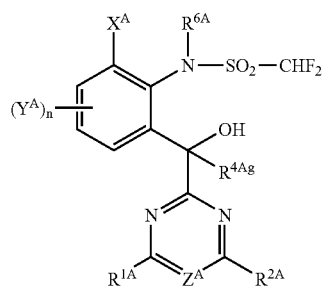

(IAg)

wherein
$R^{4Ag}$ represents hydrogen or alkyl,
$X^A$, $Y^A$, $Z^A$, n, $R^{1A}$, $R^{2A}$ and $R^{6A}$ have the same definition as aforementioned,
are reacted with a hologenating agent in the presence of innert solvents,
or,
h) in case that $R^{3A}$ represents alkoxy or alkylthio and $R^{4A}$ represents hydrogen or alkyl:
compounds of the formula (IAh)

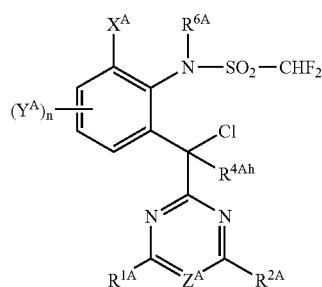

(IAh)

wherein
$R^{4Ah}$ represents hydrogen or alkyl,
$X^A$, $Y^A$, $Z^A$, n, $R^{1A}$, $R^{2A}$ and $R^{6A}$ have the same definition as aforementioned,
are reacted with compounds of the formula (V)

$$R^{3Ah}-M \quad (V)$$

wherein
$R^{3Ah}$ represents alkoxy or alkylthio,
M represents hydrogen or alkali metal,
in the presence of innert solvents, and if appropriate, in the presence of an acid binder.

The compounds represented by the formula (I), which include the novel compounds of the formula (IA), show a strong plant pest controlling action.

In the present specification,
"Halogen" represents fluorine, chlorine, bromine or iodine, preferably represents fluorine or chlorine.

"Alkyl" can be straight-chain or branched-chain and there can be mentioned, for example, $C_{1-6}$alkyl, specifically methyl, ethyl, n- or iso-propyl, n-, iso-, sec- or tert-butyl, n- or neo-pentyl, n-hexyl, etc.

"Cycloalkyl": there can be mentioned, for example, cyclopropyl, cyclobutyl, cyclopentyl, cyclohexyl, cycloheptyl, etc.

"Alkenyl" can be straight-chain or branched-chain and there can be mentioned, for example, $C_{2-7}$alkenyl, specifically vinyl, allyl, isopropenyl, 1-propenyl, 1-butenyl, 2-butenyl, 3-butenyl, 1-methyl-1-propenyl, 2-methyl-1-propenyl, 1-pentenyl, 2-pentenyl, 1-hexenyl, 2-hexenyl, 1-heptenyl, 2-heptenyl, etc.

"Alkynyl" can be straight-chain or branched-chain and there can be mentioned, for example, $C_{2-7}$alkynyl, specifically ethynyl, 1-propynyl, 2-propynyl, 1-butynyl, 2-butynyl, 3-butynyl, 1-pentynyl, 2-pentynyl, 1-hexynyl, 2-hexynyl, 1-heptynyl, 2-heptynyl, etc.

"Alkoxy" represents an alkyl-O-group, whose alkyl part has the above-mentioned meaning, and can be, for example, $C_{1-6}$alkoxy, and there can be specifically mentioned methoxy, ethoxy, n- or iso-propoxy, n-, iso-, sec- or tert-butoxy, n-pentyloxy, n-hexyloxy, etc.

"Alkylthio" represents an alkyl-S-group, whose alkyl part has the above-mentioned meaning, and can be, for example, $C_{1-6}$alkylthio, and there can be specifically mentioned methylthio, ethylthio, n- or iso-propylthio, n-, iso-, sec- or tert-butylthio, n-pentylthio, n-hexylthio, etc.

"Alkylsulfinyl" represents an alkyl-S(O)-group, whose alkyl part has the above-mentioned meaning, and can be, for example, $C_{1-6}$alkylsulfinyl, and there can be specifically mentioned methylsulfinyl, ethylsulfinyl, n- or iso-propylsulfinyl, n-, iso-, sec- or tert-butylsulfinyl, n-pentylsulfinyl, n-hexylsulfinyl, etc.

"Alkylsulfonyl" represents an alkyl-$SO_2$-group, whose alkyl part has the above-mentioned meaning, and can be, for example, $C_{1-6}$alkylsulfonyl, and there can be specifically mentioned methylsulfonyl, ethylsulfonyl, n- or iso-propylsulfonyl, n-, iso-, sec- or tert-butylsulfonyl, n-pentylsulfonyl, n-hexylsulfonyl, etc.

"Alkylsulfonyloxy" represents an alkyl-$SO_2$—O-group, whose alkyl part has the above-mentioned meaning, and can be, for example, $C_{1-6}$alkylsulfonyloxy, and there can be specifically mentioned methylsulfonyloxy, ethylsulfonyloxy, n- or iso-propylsulfonyloxy, n-, iso-, sec- or tert-butyl-sulfonyloxy, n-pentylsulfonyloxy, n-hexylsulfonyloxy, etc.

"Haloalkyl" represents a straight-chain or branched-chain alkyl, at least one of whose hydrogen is substituted with halogen and there can be mentioned, for example, $C_{1-6}$alkyl, substituted with 1 to 6 fluoro, chloro and/or bromo, and as specific examples there can be mentioned fluoromethyl, chloromethyl, dichloromethyl, bromomethyl, difluoromethyl, trifluoromethyl, chlorodifluoro-methyl, trichloromethyl, 2-fluoroethyl, 2-chloroethyl, 2,2,2-trifluoroethyl, 2-chloro-1,1,2-tri-fluoroethyl, 3-fluoropropyl, 3-chloropropyl, 2,2,3,3,3-pentafluoropropyl, 1,2,2,3,3,3-hexafluoropropyl, etc.

Haloalkyl part in "haloalkoxy", "haloalkylthio", "haloalkylsulfinyl",
"haloalkylsulfonyl" and "haloalkylsulfonyloxy" can be of the same definition as the afore-mentioned "haloalkyl" and
specifically as "haloalkoxy" there can be mentioned, for example, difluoromethoxy, trifluoromethoxy, chlorodifluoromethoxy, dichloromethoxy, 2-fluoroethoxy, 2-chloroethoxy, 2,2,2-trifluoroethoxy, 3-chloropropoxy, etc., specifically as "haloalkylthio" there can be mentioned, for example, difluoromethylthio, trifluoromethylthio, 2,2,2-trifluoroethylthio, 3-fluoropropylthio, etc., specifically as "haloalkylsulfinyl" there can be mentioned, for example, difluoromethylsulfinyl, trifluoromethylsulfinyl, 2,2,2-trifluoroethylsulfinyl, 3-fluoropropylsulfinyl, etc., specifically as "haloalkylsulfonyl" there can be mentioned, for example, difluoromethylsulfonyl, trifluoromethylsulfonyl, 2,2,2-trifluoroethylsulfonyl, 3-fluoropropylsulfonyl, etc., and specifically as "haloalkylsulfonyloxy" there can be mentioned, for example, difluoromethylsulfonyloxy, trifluoromethylsulfonyloxy, 2,2,2-trifluoroethylsulfonyloxy, 3-fluoropropylsulfonyloxy, etc., "Acyl" includes alkyl-(C=O)-group, whose alkyl part has the above-mentioned meaning, and cycloalkyl-(C=O)-group, whose cycloalkyl part has the above-mentioned meaning, and can be, for example, $C_{1-6}$alkyl-(C=O)-group or $C_{2-7}$cycloalkyl-(C=O)-group, and there can be specifically mentioned methylcarbonyl (acetyl), ethylcarbonyl (propionyl), cyclopropylcarbonyl, cyclopentylcarbonyl, cyclohexylcarbonyl, etc.

"Dialkylamino" is amino, substituted with two identical or different alkyls, and there can be specifically mentioned, for example, dimethylamino, diethylamino, di(n- or iso-propyl)amino, etc.

As "alkoxycarbonyl" there can be mentioned, for example, methoxycarbonyl, ethoxycarbonyl, n- or iso-propoxycarbonyl, etc.

As "dialkylaminocarbonyl": there can be mentioned, for example, dimethylaminocarbonyl, diethylaminocarbonyl, di(n-propyl)aminocarbonyl, etc.

As "alkoxycarbonylamino" there can be mentioned, for example, methoxycarbonylamino, ethoxycarbonylamino, n- or iso-propoxycarbonylamino, etc.

As "alkoxyalkyl" there can be mentioned, for example, methoxymethyl, 2-methoxyethyl, 1-methoxyethyl, 3-methoxypropyl, ethoxymethyl, 2-ethoxyethyl, etc.

As substituents in "alkyl that may be optionally substituted" there can be mentioned cyano, phenyl, alkoxycarbonyl, halogen, etc. and alkyl that may be substituted with such substituents includes, for example, $C_{1-6}$alkyl that may be cyano-substituted, $C_{1-6}$alkyl that may be phenyl-substituted, $C_{1-6}$alkyl that may be substituted with $C_{1-6}$alkoxycarbonyl, $C_{1-6}$alkyl, at least one hydrogen of which may be substituted with halogen atom, particularly with 1-6 fluoro, chloro and/or bromo, and there can be specifically mentioned methyl, ethyl, n- or iso-propyl, n-, iso-, sec- or tert-butyl, n- or neo-pentyl, n-heptyl; cyanomethyl, 1-cyanoethyl, 2-cyanoethyl; benzyl, 2-phenylethyl, 1-phenylethyl (phenethyl), 1-phenylpropyl, 2-phenylpropyl, 3-phenylpropyl; methoxycarbonylmethyl, ethoxycarbonylmethyl, (n- or iso-)propyloxycarbonylmethyl, (n-, iso-, sec- or tert-)butyloxycarbonylmethyl, 2-methoxycarbonylethyl, 3-methoxycarbonylpropyl; fluoromethyl, chloromethyl, dichloromethyl, bromomethyl, difluoromethyl, trifluoromethyl, chlorodifluoromethyl, dichloromethyl, trichloromethyl, 2,2,2-trifluoroethyl, 2-chloro-1,1,2-trifluoroethyl, 3-fluoropropyl, 3-chloropropyl, 2,2,3,3,3-pentafluoropropyl, 1,2,2,3,3,3-hexafluoropropyl, etc.

In the compounds of the aforementioned formula (IA), preferably $X^A$ represents hydrogen, fluorine, chlorine, $C_{1-6}$alkyl, $C_{1-6}$alkoxy-carbonyl, $C_{1-6}$alkyl-carbonyl, $C_{3-7}$cycloalkyl-carbonyl, di($C_{1-6}$alkyl)aminocarbonyl, $C_{1-6}$alkoxy, $C_{1-6}$alkylsulfonyl, $C_{1-6}$alkylsulfonyloxy, di($C_{1-6}$alkyl)amino, $C_{1-6}$haloalkoxy, $C_{1-6}$haloalkylthio, $C_{1-6}$haloalkylsulfinyl, $C_{1-6}$haloalkylsulfonyl, $C_{1-6}$haloalkylsulfonyloxy, formyl, carboxy, cyano, nitro or phenoxy, $Y^A$ represents fluorine, chlorine, $C_{1-6}$alkyl, at least one hydrogen of which may be optionally halogen-substituted, $C_{1-6}$alkoxy-$C_{1-6}$alkyl, $C_{1-6}$alkoxy-carbonyl, $C_{1-6}$alkyl-carbonyl, $C_{1-6}$alkoxy, $C_{1-6}$alkylsulfonyl, $C_{1-6}$haloalkoxy, $C_{1-6}$haloalkylthio, $C_{1-6}$haloalkylsulfinyl, $C_{1-6}$haloalkylsulfonyl, di($C_{1-6}$alkyl)amino, cyano or nitro, and 2 $Y^A$'s may be identical or different each other in case that n is 2, $Z^A$ represents C—$R^{7A}$ or N, n represents 0, 1 or 2, $R^{1A}$ and $R^{2A}$ each independently represents hydrogen, chlorine, $C_{1-6}$alkyl, at least one hydrogen of which may be optionally halogen-substituted, $C_{3-7}$cycloalkyl, $C_{1-6}$alkoxy, $C_{1-6}$haloalkoxy or $C_{1-6}$alkylthio, $R^{3A}$ and $R^{4A}$ each independently represents hydrogen, fluorine, chlorine, $C_{1-6}$alkyl, $C_{1-6}$alkoxy, $C_{1-6}$alkylthio or $C_{1-6}$alkylsulfonyl, $R^{3A}$ represents hydroxy and $R^{4A}$ represents hydrogen or $C_{1-6}$alkyl, or $R^{3A}$ and $R^{4A}$ together may form C=O with the carbon atom to which they are bonded, $R^{6A}$ represents hydrogen, $C_{1-6}$alkyl, at least one hydrogen of which may be optionally halogen-substituted, $C_{1-6}$alkoxy-$C_{1-6}$alkyl, $C_{1-6}$alkoxy-carbonyl, $C_{1-6}$alkyl-carbonyl, $C_{3-7}$cycloalkyl-carbonyl, or group —$SO_2R^{5A}$, $R^{5A}$ represents $C_{1-6}$alkyl, $C_{1-6}$haloalkyl or cyano-substituted $C_{1-6}$alkyl, and $R^{7A}$ represents hydrogen or $C_{1-6}$alkyl, with the exception of the following cases (T-1)-(T-3) are excluded:

(T-1) the case in which $X^A$ represents $C_{1-6}$ alkyl, and n represents 0, (T-2) the case in which $X^A$ represents hydrogen, n represents 0, $Z^A$ represents CH, $R^{1A}$ and $R^{2A}$ represent methoxy, $R^{3A}$ represents hydroxy and $R^{4A}$ represents hydrogen, or $R^{3A}$ and $R^{4A}$ together form C=O with the carbon atom to which they are bonded, and $R^{6A}$ represents hydrogen, (T-3) the case in which $X^A$ represents fluorine or chlorine, n represents 0, $Z^A$ represents CH or N, $R^{1A}$ and $R^{2A}$ represent methoxy, $R^{3A}$ and $R^{4A}$ represent hydrogen, $R^{3A}$ represents hydroxy and $R^{4A}$ represents hydrogen, or $R^{3A}$ and $R^{4A}$ together form C=O with the carbon atom to which they are bonded, and $R^{6A}$ represents hydrogen.

In the compounds of the aforementioned formula (IA), particularly preferably $X^A$ represents hydrogen, fluorine, chlorine, $C_{1-4}$alkyl, $C_{1-4}$alkoxy-carbonyl, $C_{1-4}$alkyl-carbonyl, $C_{3-5}$-cycloalkyl-carbonyl, di($C_{1-4}$alkyl)aminocarbonyl, $C_{1-4}$alkoxy, $C_{1-4}$alkylsulfonyl, $C_{1-4}$alkylsulfonyloxy, di($C_{1-4}$alkyl)amino, $C_{1-4}$haloalkoxy, $C_{1-4}$haloalkylthio, $C_{1-4}$haloalkylsulfinyl, $C_{1-4}$haloalkylsulfonyl, $C_{1-4}$haloalkylsulfonyloxy, formyl, carboxy, cyano, nitro or phenoxy, $Y^A$ represents fluorine, chlorine, $C_{1-4}$alkyl, at least one hydrogen of which may be optionally fluoro-substituted, $C_{1-4}$alkoxy-$C_{1-4}$alkyl, $C_{1-4}$alkoxy-carbonyl, $C_{1-4}$alkyl-carbonyl, $C_{1-4}$alkoxy, $C_{1-4}$alkylsulfonyl, $C_{1-4}$haloalkoxy, $C_{1-4}$haloalkylthio, $C_{1-4}$haloalkylsulfinyl, $C_{1-4}$haloalkylsulfonyl, di($C_{1-4}$alkyl)amino, cyano or nitro, and 2 $Y^A$'s may be identical or different each other in case that n is 2, $Z^A$ represents C—$R^{7A}$ or N, n represents 0, 1 or 2, $R^{1A}$ and $R^{2A}$ each independently represents hydrogen, chlorine, $C_{1-4}$alkyl, at least one hydrogen of which may be optionally fluoro-substituted, $C_{3-5}$cycloalkyl, $C_{1-4}$alkoxy, $C_{1-4}$haloalkoxy or $C_{1-4}$alkylthio, $R^{3A}$ and $R^{4A}$ each independently represents hydrogen, fluorine, chlorine, $C_{1-4}$alkyl, $C_{1-4}$alkoxy, $C_{1-4}$alkylthio or $C_{1-4}$alkylsulfonyl, $R^{3A}$ represents hydroxy and $R^{4A}$ represents hydrogen or $C_{1-4}$alkyl, or $R^{3A}$ and $R^{4A}$ together may form C=O with the carbon atom to which they are bonded, $R^{6A}$ represents hydrogen, $C_{1-4}$alkyl, at least one hydrogen of which may be optionally fluoro-substituted, $C_{1-4}$alkoxy-$C_{1-4}$alkyl, $C_{1-4}$alkoxy-carbonyl, $C_{1-4}$alkyl-carbonyl, $C_{3-5}$cycloalkyl-carbonyl, or group —$SO_2R^{5A}$, $R^{5A}$ represents $C_{1-4}$alkyl, $C_{1-4}$haloalkyl or cyano-substituted $C_{1-4}$alkyl, and $R^{7A}$ represents hydrogen or $C_{1-4}$alkyl, with the exception of the following cases (T-1)-(T-3), (T-1) the case in which $X^A$ represents $C_{1-4}$alkyl, and n represents 0, (T-2) the case in which $X^A$ represents hydrogen, n represents 0, $Z^A$ represents CH, $R^{1A}$ and $R^{2A}$ represent methoxy, $R^{3A}$ represents hydroxy and $R^{4A}$ represents hydrogen, or $R^{3A}$ and $R^{4A}$ together form C=O with the carbon atom to which they are bonded, and $R^{6A}$ represents hydrogen, (T-3) the case in which $X^A$ represents fluorine or chlorine, n represents 0, $Z^A$ represents CH or N, $R^{1A}$ and $R^{2A}$ represent methoxy, $R^{3A}$ and $R^{4A}$ represent hydrogen, $R^{3A}$ represents hydroxy and $R^{4A}$ represents hydrogen, or $R^{3A}$ and $R^{4A}$ together form C=O with the carbon atom to which they are bonded, and $R^{6A}$ represents hydrogen.

The aforementioned preparation process (a) can be illustrated by the following reaction scheme in case that, for example, 2-chloro-6-[(4,6-dimethoxypyrimidin-2-yl)methyl]aniline and difluoromethanesulfonyl chloride are used as the starting materials.

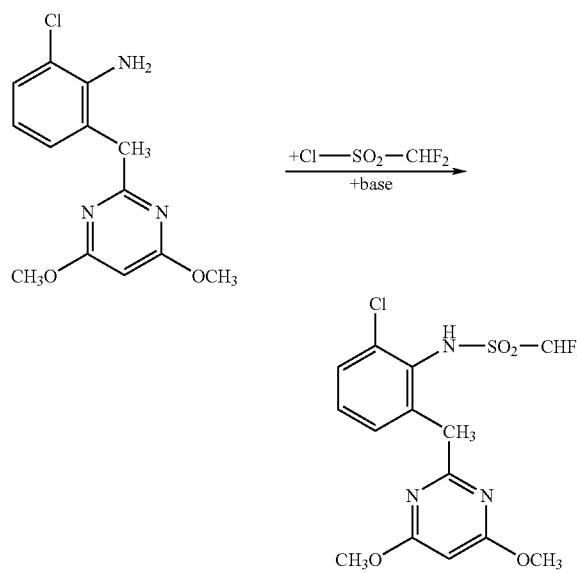

The aforementioned preparation process (b) can be illustrated by the following reaction scheme in case that, for example, 2-fluoro-6-[(4,6-dimethoxypyrimidin-2-yl)methyl]-N-difluoromethanesulfonanilide and methyl iodide are used as the starting materials.

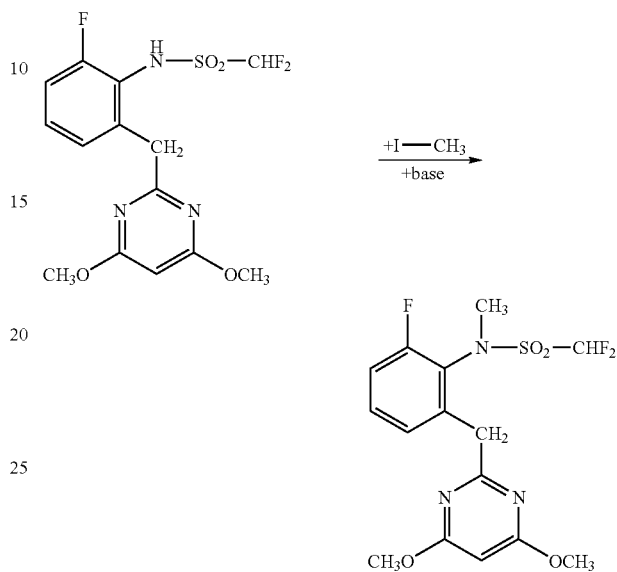

The aforementioned preparation process (c) can be illustrated by the following reaction scheme in case that, for example, 2-fluoro-6-[1-(4,6-dimethoxypyrimidin-2-yl)-1-methylthiomethyl]-N-difluoromethanesulfonanilide and, as reducing agent, for example, sodium borohydride and nickel (II) chloride hexahydrate, are used as the starting materials.

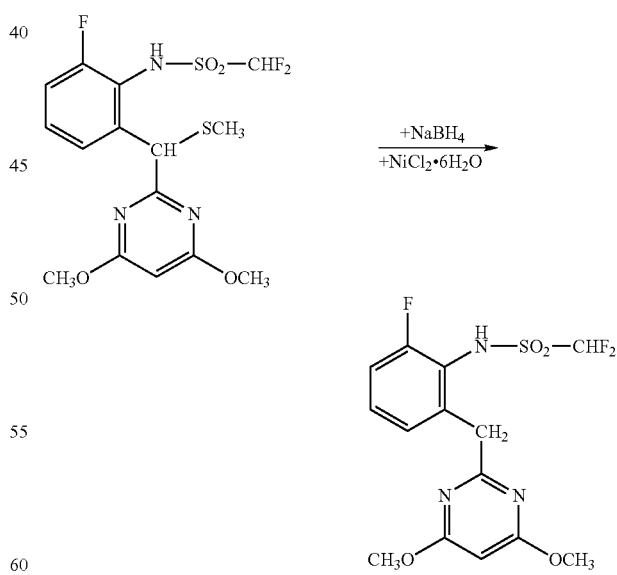

The aforementioned preparation process (d) can illustrated by the following reaction scheme in case that, for example, 2-chloro-6-[(4,6-dimethoxypyrimidin-2-yl)methyl]-N-difluoromethanesulfonanilide and chromium (VI) oxide are used as the starting materials.

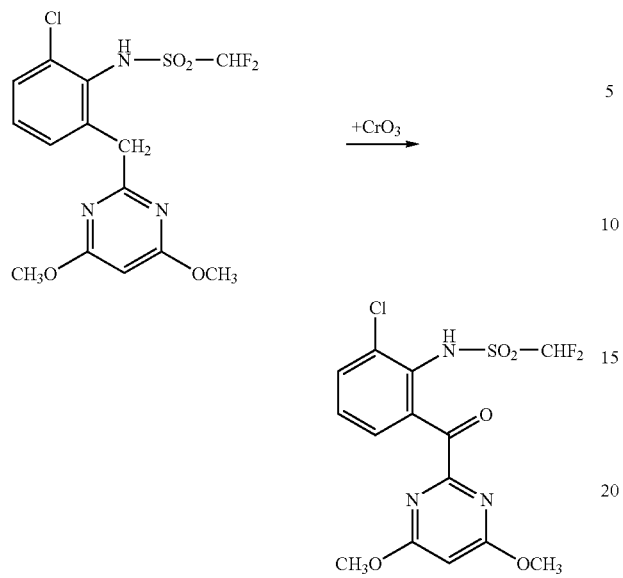

The aforementioned preparation process (e) can be illustrated by the following reaction scheme in case that, for example, 2-chloro-6-[(4,6-dimethoxypyrimidin-2-yl)carbonyl]aniline and methyl magnesium iodide are used as the starting materials.

The aforementioned preparation process (g) can be illustrated by the following reaction scheme in case that, for example, 2-chloro-6-[1-(4,6-dimethoxypyrimidin-2-yl)hydroxymethyl]-N-difluoromethanesulfonanilide and thionyl chloride are used as the starting materials.

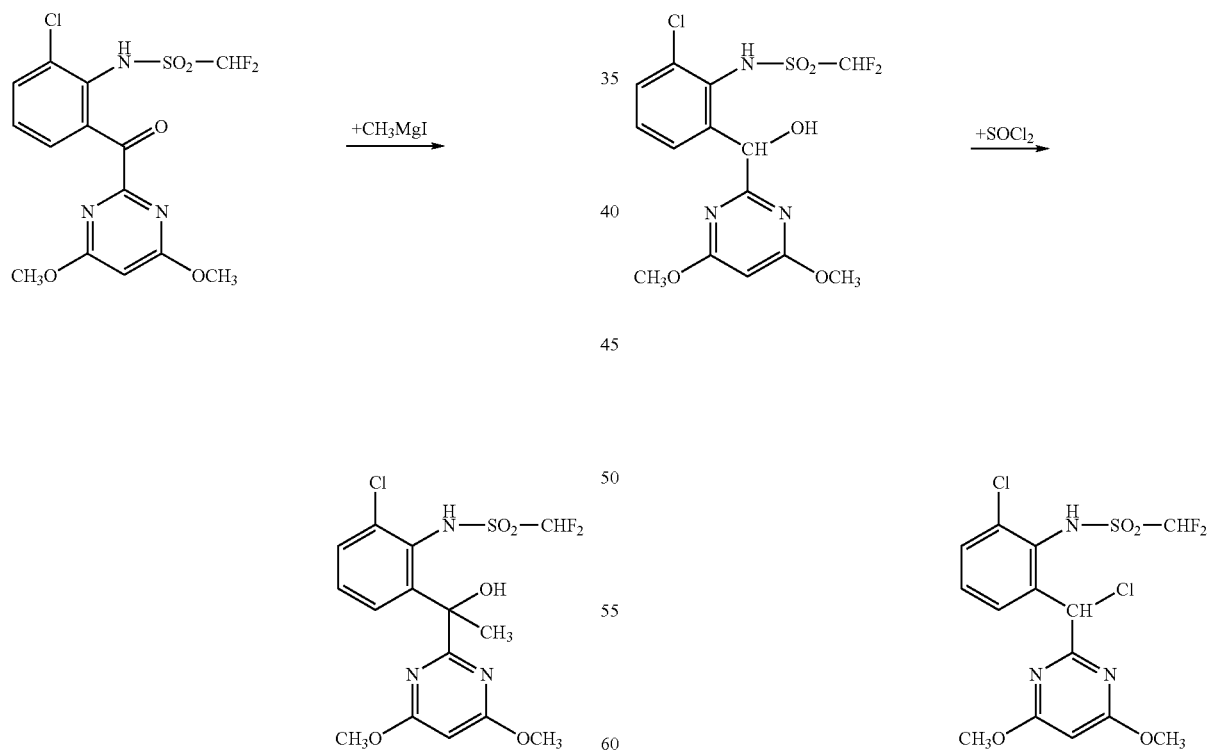

The aforementioned preparation process (f) can be illustrated by the following reaction scheme in case that, for example, 2-chloro-6-[(4,6-dimethoxypyrimidin-2-yl)carbonyl]aniline and, as reducing agent, for example, sodium borohydride, are used as the starting materials.

The aforementioned preparation process (h) can be illustrated by the following reaction scheme in case that, for example, 2-chloro-6-[1-(4,6-dimethoxypyrimidin-2-yl)-1-chloromethyl]-N-difluoromethanesulfonanilide and sodium methoxide are used as the starting materials.

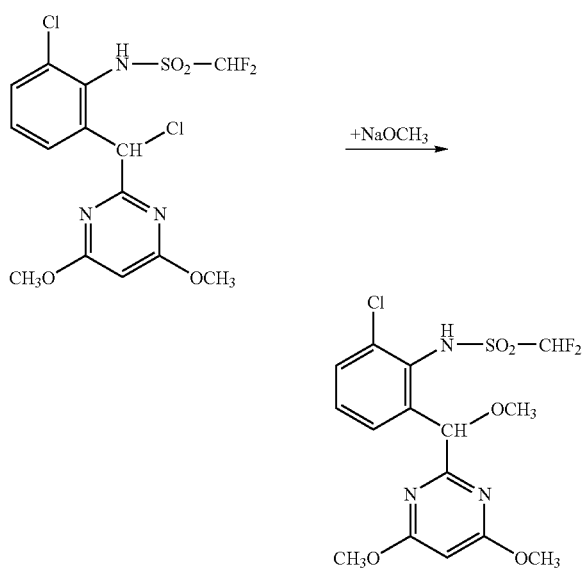

The compounds of the formula (II), used as the starting materials in the aforementioned preparation process (a), that include the known compounds described in the aforementioned patent literatures 1-3, a part of which are novel compounds that are not described in the existing literatures, can be prepared, for example, according to the processes described in any of the aforementioned patent literatures 1-3. As specific examples of the compounds of the formula (II) there can be mentioned as follows:

2-fluoro-6-[1-(4,6-dimethoxypyrimidin-2-yl)-1-methylthiomethyl]aniline,
2-chloro-6-[1-(4,6-dimethoxypyrimidin-2-yl)-1-methylthiomethyl]aniline,
2-bromo-6-[1-(4,6-dimethoxypyrimidin-2-yl)-1-methylthiomethyl]aniline,
2-iodo-6-[1-(4,6-dimethoxypyrimidin-2-yl)-1-methylthiomethyl]aniline,
2-trifluoromethoxy-6-[1-(4,6-dimethoxypyrimidin-2-yl)-1-methylthiomethyl]aniline,
3-fluoro-6-[1-(4,6-dimethoxypyrimidin-2-yl)-1-methylthiomethyl]aniline,
3-chloro-6-[1-(4,6-dimethoxypyrimidin-2-yl)-1-methylthiomethyl]aniline,
4-fluoro-6-[1-(4,6-dimethoxypyrimidin-2-yl)-1-methylthiomethyl]aniline,
4-chloro-6-[1-(4,6-dimethoxypyrimidin-2-yl)-1-methylthiomethyl]aniline,
5-fluoro-6-[1-(4,6-dimethoxypyrimidin-2-yl)-1-methylthiomethyl]aniline,
5-chloro-6-[1-(4,6-dimethoxypyrimidin-2-yl)-1-methylthiomethyl]aniline,
2,3-difluoro-6-[1-(4,6-dimethoxypyrimidin-2-yl)-1-methylthiomethyl]aniline,
2,3-dichloro-6-[1-(4,6-dimethoxypyrimidin-2-yl)-1-methylthiomethyl]aniline,
2-fluoro-3-chloro-6-[1-(4,6-dimethoxypyrimidin-2-yl)-1-methylthiomethyl]aniline,
3-fluoro-2-chloro-6-[1-(4,6-dimethoxypyrimidin-2-yl)-1-methylthiomethyl]aniline,
2,4-difluoro-6-[1-(4,6-dimethoxypyrimidin-2-yl)-1-methylthiomethyl]aniline,
2,4-dichloro-6-[1-(4,6-dimethoxypyrimidin-2-yl)-1-methylthiomethyl]aniline,
2-fluoro-4-chloro-6-[1-(4,6-dimethoxypyrimidin-2-yl)-1-methylthiomethyl]aniline,
4-fluoro-2-chloro-6-[1-(4,6-dimethoxypyrimidin-2-yl)-1-methylthiomethyl]aniline,
2,5-difluoro-6-[1-(4,6-dimethoxypyrimidin-2-yl)-1-methylthiomethyl]aniline,
2,5-dichloro-6-[1-(4,6-dimethoxypyrimidin-2-yl)-1-methylthiomethyl]aniline,
2-fluoro-5-chloro-6-[1-(4,6-dimethoxypyrimidin-2-yl)-1-methylthiomethyl]aniline,
5-fluoro-2-chloro-6-[1-(4,6-dimethoxypyrimidin-2-yl)-1-methylthiomethyl]aniline,
3,4-difluoro-6-[1-(4,6-dimethoxypyrimidin-2-yl)-1-methylthiomethyl]aniline,
3,4-dichloro-6-[1-(4,6-dimethoxypyrimidin-2-yl)-1-methylthiomethyl]aniline,
3,5-difluoro-6-[1-(4,6-dimethoxypyrimidin-2-yl)-1-methylthiomethyl]aniline,
3,5-dichloro-6-[1-(4,6-dimethoxypyrimidin-2-yl)-1-methylthiomethyl]aniline,
2-fluoro-6-[1-(4,6-dimethylpyrimidin-2-yl)-1-methylthiomethyl]aniline,
2-chloro-6-[1-(4,6-dimethylpyrimidin-2-yl)-1-methylthiomethyl]aniline,
2-fluoro-6-[1-(4-methoxy-6-methylpyrimidin-2-yl)-1-methylthiomethyl]aniline,
2-chloro-6-[1-(4-methoxy-6-methylpyrimidin-2-yl)-1-methylthiomethyl]aniline,
2-fluoro-6-[1-(4-methoxy-6-trifluoromethylpyrimidin-2-yl)-1-methylthiomethyl]aniline,
2-chloro-6-[1-(4-methoxy-6-trifluoromethylpyrimidin-2-yl)-1-methylthiomethyl]aniline,
3-fluoro-6-[1-(4-methoxy-6-methylpyrimidin-2-yl)-1-methylthiomethyl]aniline,
3-chloro-6-[1-(4-methoxy-6-methylpyrimidin-2-yl)-1-methylthiomethyl]aniline,
2-fluoro-6-[1-(4,6-dimethoxypyrimidin-2-yl)-1-methylthioethyl]aniline,
2-chloro-6-[1-(4,6-dimethoxypyrimidin-2-yl)-1-methylthioethyl]aniline,
2-fluoro-6-[1-(4,6-dimethylpyrimidin-2-yl)-1-methylthioethyl]aniline,
2-chloro-6-[1-(4,6-dimethylpyrimidin-2-yl)-1-methylthioethyl]aniline,
2-fluoro-6-[1-(4,6-dimethoxytriazin-2-yl)-1-methylthiomethyl]aniline,
2-chloro-6-[1-(4,6-dimethoxytriazin-2-yl)-1-methylthiomethyl]aniline,
2-bromo-6-[1-(4,6-dimethoxyrtiazin-2-yl)-1-methylthiomethyl]aniline,
2-iodo-6-[1-(4,6-dimethoxytriazin-2-yl)-1-methylthiomethyl]aniline,
3-fluoro-6-[1-(4,6-dimethoxytriazin-2-yl)-1-methylthiomethyl]aniline,
3-chloro-6-[1-(4,6-dimethoxytriazin-2-yl)-1-methylthiomethyl]aniline,
2,3-difluoro-6-[1-(4,6-dimethoxytriazin-2-yl)-1-methylthiomethyl]aniline,
2,3-dichloro-6-[1-(4,6-dimethoxytriazin-2-yl)-1-methylthiomethyl]aniline,
2-fluoro-6-[1-(4,6-dimethoxytriazin-2-yl)-1-methylthioethyl]aniline,
2-chloro-6-[1-(4,6-dimethoxytriazin-2-yl)-1-methylthioethyl]aniline,
2-fluoro-6-[1-(4,6-dimethyltriazin-2-yl)-1-methylthioethyl]aniline, 2-chloro-6-[1-(4,6-dimethyltriazin-2-yl)-1-methylthioethyl]aniline,
2-fluoro-6-[(4,6-dimethoxypyrimidin-2-yl)methyl]aniline,
2-chloro-6-[(4,6-dimethoxypyrimidin-2-yl)methyl]aniline,
2-fluoro-6-[(4,6-dimethylpyrimidin-2-yl)methyl]aniline,
2-chloro-6-[(4,6-dimethylpyrimidin-2-yl)methyl]aniline,
2,3-difluoro-6-[(4,6-dimethoxypyrimidin-2-yl)methyl]aniline,
2,3-dichloro-6-[(4,6-dimethoxypyrimidin-2-yl)methyl]aniline,
2-fluoro-3-chloro-6-[(4,6-dimethoxypyrimidin-2-yl)methyl]aniline,
3-fluoro-2-chloro-6-[(4,6-dimethoxypyrimidin-2-yl)methyl]aniline,
2,4-difluoro-6-[(4,6-dimethoxypyrimidin-2-yl)methyl]aniline,
2,4-dichloro-6-[(4,6-dimethoxypyrimidin-2-yl)methyl]aniline,
2-fluoro-4-chloro-6-[(4,6-dimethoxypyrimidin-2-yl)methyl]aniline,
4-fluoro-2-chloro-6-[(4,6-dimethoxypyrimidin-2-yl)methyl]aniline,
2,5-difluoro-6-[(4,6-dimethoxypyrimidin-2-yl)methyl]aniline,
2,5-dichloro-6-[(4,6-dimethoxypyrimidin-2-yl)methyl]aniline,
2-fluoro-5-chloro-6-[(4,6-dimethoxypyrimidin-2-yl)methyl]aniline,
5-fluoro-2-chloro-6-[(4,6-dimethoxypyrimidin-2-yl)methyl]aniline,
2-fluoro-6-[1-(4,6-dimethoxypyrimidin-2-yl)ethyl]aniline,
2-chloro-6-[1-(4,6-dimethoxypyrimidin-2-yl)ethyl]aniline,
2-fluoro-6-[1-(4,6-dimethylpyrimidin-2-yl)ethyl]aniline,
2-chloro-6-[1-(4,6-dimethylpyrimidin-2-yl)ethyl]aniline,
3-fluoro-6-[(4,6-dimethylpyrimidin-2-yl)methyl]aniline,
3-chloro-6-[(4,6-dimethylpyrimidin-2-yl)methyl]aniline,
2-fluoro-6-[(4-methoxy-6-methylpyrimidin-2-yl)methyl]aniline,
2-chloro-6-[(4-methoxy-6-methylpyrimidin-2-yl)methyl]aniline,
2-fluoro-6-[(4-methoxy-6-trifluoromethylpyrimidin-2-yl)methyl]aniline,
2-chloro-6-[(4-methoxy-6-trifluoromethylpyrimidin-2-yl)methyl]aniline,
3-fluoro-6-[(4-methoxy-6-methylpyrimidin-2-yl)methyl]aniline,
3-chloro-6-[(4-methoxy-6-methylpyrimidin-2-yl)methyl]aniline,
2-fluoro-6-[(4,6-dimethoxytriazin-2-yl)methyl]aniline,
2-chloro-6-[(4,6-dimethoxytriazin-2-yl)methyl]aniline,
2,3-difluoro-6-[(4,6-dimethoxytriazin-2-yl)methyl]aniline,
2,3-dichloro-6-[(4,6-dimethoxytriazin-2-yl)methyl]aniline,
2-fluoro-6-[1-(4,6-dimethoxytriazin-2-yl)ethyl]aniline,
2-chloro-6-[1-(4,6-dimethoxytriazin-2-yl)ethyl]aniline,
2-fluoro-6-[1-(4,6-dimethyltriazin-2-yl)ethyl]aniline,
2-chloro-6-[1-(4,6-dimethyltriazin-2-yl)ethyl]aniline,
2-fluoro-6-[(4,6-dimethoxypyrimidin-2-yl)carbonyl]aniline,
2-chloro-6-[(4,6-dimethoxypyrimidin-2-yl)carbonyl]aniline,
2,3-difluoro-6-[(4,6-dimethoxypyrimidin-2-yl)carbonyl]aniline,
2,3-dichloro-6-[(4,6-dimethoxypyrimidin-2-yl)carbonyl]aniline,
2-fluoro-3-chloro-6-[(4,6-dimethoxypyrimidin-2-yl)carbonyl]aniline,
3-fluoro-2-chloro-6-[(4,6-dimethoxypyrimidin-2-yl)carbonyl]aniline,
2,4-difluoro-6-[(4,6-dimethoxypyrimidin-2-yl)carbonyl]aniline,
2,4-dichloro-6-[(4,6-dimethoxypyrimidin-2-yl)carbonyl]aniline,
2-fluoro-4-chloro-6-[(4,6-dimethoxypyrimidin-2-yl)carbonyl]aniline,
4-fluoro-2-chloro-6-[(4,6-dimethoxypyrimidin-2-yl)carbonyl]aniline,
2,5-difluoro-6-[(4,6-dimethoxypyrimidin-2-yl)carbonyl]aniline,
2,5-dichloro-6-[(4,6-dimethoxypyrimidin-2-yl)carbonyl]aniline,
2-fluoro-5-chloro-6-[(4,6-dimethoxypyrimidin-2-yl)carbonyl]aniline,
5-fluoro-2-chloro-6-[(4,6-dimethoxypyrimidin-2-yl)carbonyl]aniline,
2-fluoro-6-[(4,6-dimethylpyrimidin-2-yl)carbonyl]aniline,
2-chloro-6-[(4,6-dimethylpyrimidin-2-yl)carbonyl]aniline,
2-fluoro-6-[(4-methoxy-6-methylpyrimidin-2-yl)carbonyl]aniline,
2-chloro-6-[(4-methoxy-6-methylpyrimidin-2-yl)carbonyl]aniline,
2-fluoro-6-[(4-methoxy-6-trifluoromethylpyrimidin-2-yl)carbonyl]aniline,
3-fluoro-6-[(4-methoxy-6-methylpyrimidin-2-yl)carbonyl]aniline,
3-chloro-6-[(4-methoxy-6-methylpyrimidin-2-yl)carbonyl]aniline,
2-fluoro-6-[(4,6-dimethoxytriazin-2-yl)carbonyl]aniline,
2-chloro-6-[(4,6-dimethoxytriazin-2-yl)carbonyl]aniline,
2-bromo-6-[(4,6-dimethoxytriazin-2-yl)carbonyl]aniline,
2-iodo-6-[(4,6-dimethoxytriazin-2-yl)carbonyl]aniline,
2,3-difluoro-6-[(4,6-dimethoxypyridin-2-yl)carbonyl]aniline,
2,3-dichloro-6-[(4,6-dimethoxypyridin-2-yl)carbonyl]aniline,
2-fluoro-6-[(4,6-dimethoxypyrimidin-2-yl)-1-hydroxymethyl]aniline,
2-chloro-6-[1-(4,6-dimethoxypyrimidin-2-yl)-1-hydroxymethyl]aniline,
2,3-difluoro-6-[1-(4,6-dimethoxypyrimidin-2-yl)-1-hydroxymethyl]aniline,
2,3-dichloro-6-[1-(4,6-dimethoxypyrimidin-2-yl)-1-hydroxymethyl]aniline,
2-fluoro-3-chloro-6-[1-(4,6-dimethoxypyrimidin-2-yl)-1-hydroxymethyl]aniline,
3-fluoro-2-chloro-6-[1-(4,6-dimethoxypyrimidin-2-yl)-1-hydroxymethyl]aniline,
2,4-difluoro-6-[1-(4,6-dimethoxypyrimidin-2-yl)-1-hydroxymethyl]aniline,
2,4-dichloro-6-[1-(4,6-dimethoxypyrimidin-2-yl)-1-hydroxymethyl]aniline,
2-fluoro-4-chloro-6-[1-(4,6-dimethoxypyrimidin-2-yl)-1-hydroxymethyl]aniline,
4-fluoro-2-chloro-6-[1-(4,6-dimethoxypyrimidin-2-yl)-1-hydroxymethyl]aniline,
2,5-difluoro-6-[1-(4,6-dimethoxypyrimidin-2-yl)-1-hydroxymethyl]aniline,
2,5-dichloro-6-[1-(4,6-dimethoxypyrimidin-2-yl)-1-hydroxymethyl]aniline,
2-fluoro-5-chloro-6-[1-(4,6-dimethoxypyrimidin-2-yl)-1-hydroxymethyl]aniline,
5-fluoro-2-chloro-6-[1-(4,6-dimethoxypyrimidin-2-yl)-1-hydroxymethyl]aniline,
2-fluoro-6-[(4,6-dimethoxypyrimidin-2-yl)-1-hydroxyethyl]aniline, 2-chloro-6-[(4,6-dimethoxypyrimidin-2-yl)-1-hydroxyethyl]aniline,
3-fluoro-6-[(4,6-dimethoxypyrimidin-2-yl)-1-hydroxyethyl]aniline,
2-chloro-6-[(4,6-dimethylpyrimidin-2-yl)-1-hydroxyethyl]aniline,
2-fluoro-6-[1-(4,6-dimethylpyrimidin-2-yl)-1-hydroxymethyl]aniline,
2-chloro-6-[1-(4,6-dimethylpyrimidin-2-yl)-1-hydroxymethyl]aniline,
2-fluoro-6-[1-(4-methoxy-6-methylpyrimidin-2-yl)-1-hydroxymethyl]aniline,
2-chloro-6-[1-(4-methoxy-6-methylpyrimidin-2-yl)-1-hydroxymethyl]aniline,
2-fluoro-6-[1-(4-methoxy-6-trifluoromethylpyrimidin-2-yl)-1-hydroxymethyl]aniline,
2-chloro-6-[1-(4-methoxy-6-trifluoromethylpyrimidin-2-yl)-1-hydroxymethyl]aniline,
3-fluoro-6-[1-(4-methoxy-6-methylpyrimidin-2-yl)-1-hydroxymethyl]aniline,
3-chloro-6-[1-(4-methoxy-6-methylpyrimidin-2-yl)-1-hydroxymethyl]aniline,
2-fluoro-6-[1-(4,6-dimethoxytriazin-2-yl)-1-hydroxymethyl]aniline,
2-chloro-6-[1-(4,6-dimethoxytriazin-2-yl)-1-hydroxymethyl]aniline,
2-bromo-6-[1-(4,6-dimethoxytriazin-2-yl)-1-hydroxymethyl]aniline,
2-iodo-6-[1-(4,6-dimethoxytriazin-2-yl)-1-hydroxymethyl]aniline,
2,3-difluoro-6-[1-(4,6-dimethoxytriazin-2-yl)-1-hydroxymethyl]aniline,
2,3-dichloro-6-[1-(4,6-dimethoxytriazin-2-yl)-1-hydroxymethyl]aniline,
2-fluoro-6-[1-(4,6-dimethoxytriazin-2-yl)-1-hydroxyethyl]aniline,
2-chloro-6-[1-(4,6-dimethoxytriazin-2-yl)-1-hydroxyethyl]aniline,
2-fluoro-6-[1-(4,6-dimethyltriazin-2-yl)-1-hydroxyethyl]aniline,
2-chloro-6-[1-(4,6-dimethyltriazin-2-yl)-1-hydroxyethyl]aniline,
2-fluoro-6-[1-(4,6-dimethoxypyrimidin-2-yl)-1-chloromethyl]aniline,
2-chloro-6-[1-(4,6-dimethoxypyrimidin-2-yl)-1-chloromethyl]aniline,
2-bromo-6-[1-(4,6-dimethoxypyrimidin-2-yl)-1-chloromethyl]aniline,
2-iodo-6-[1-(4,6-dimethoxypyrimidin-2-yl)-1-chloromethyl]aniline,
2-trifluoromethoxy-6-[1-(4,6-dimethoxypyrimidin-2-yl)-1-chloromethyl]aniline,
3-fluoro-6-[1-(4,6-dimethoxypyrimidin-2-yl)-1-chloromethyl]aniline,
3-chloro-6-[1-(4,6-dimethoxypyrimidin-2-yl)-1-chloromethyl]aniline,
4-fluoro-6-[1-(4,6-dimethoxypyrimidin-2-yl)-1-chloromethyl]aniline,
4-chloro-6-[1-(4,6-dimethoxypyrimidin-2-yl)-1-chloromethyl]aniline,
5-fluoro-6-[1-(4,6-dimethoxypyrimidin-2-yl)-1-chloromethyl]aniline,
5-chloro-6-[1-(4,6-dimethoxypyrimidin-2-yl)-1-chloromethyl]aniline,
2,3-difluoro-6-[1-(4,6-dimethoxypyrimidin-2-yl)-1-chloromethyl]aniline,
2,3-dichloro-6-[1-(4,6-dimethoxypyrimidin-2-yl)-1-chloromethyl]aniline,
2-fluoro-3-chloro-6-[1-(4,6-dimethoxypyrimidin-2-yl)-1-chloromethyl]aniline,
3-fluoro-2-chloro-6-[1-(4,6-dimethoxypyrimidin-2-yl)-1-chloromethyl]aniline,
2,4-difluoro-6-[1-(4,6-dimethoxypyrimidin-2-yl)-1-chloromethyl]aniline,
2,4-dichloro-6-[1-(4,6-dimethoxypyrimidin-2-yl)-1-chloromethyl]aniline,
2-fluoro-4-chloro-6-[1-(4,6-dimethoxypyrimidin-2-yl)-1-chloromethyl]aniline,
4-fluoro-2-chloro-6-[1-(4,6-dimethoxypyrimidin-2-yl)-1-chloromethyl]aniline,
2,5-difluoro-6-[1-(4,6-dimethoxypyrimidin-2-yl)-1-chloromethyl]aniline,
2,5-dichloro-6-[1-(4,6-dimethoxypyrimidin-2-yl)-1-chloromethyl]aniline,
2-fluoro-5-chloro-6-[1-(4,6-dimethoxypyrimidin-2-yl)-1-chloromethyl]aniline,
5-fluoro-2-chloro-6-[1-(4,6-dimethoxypyrimidin-2-yl)-1-chloromethyl]aniline,
3,4-difluoro-6-[1'-(4,6-dimethoxypyrimidin-2-yl)-1-chloromethyl]aniline,
3,4-dichloro-6-[1-(4,6-dimethoxypyrimidin-2-yl)-1-chloromethyl]aniline,
3,5-difluoro-6-[1-(4,6-dimethoxypyrimidin-2-yl)-1-chloromethyl]aniline,
3,5-dichloro-6-[1-(4,6-dimethoxypyrimidin-2-yl)-1-chloromethyl]aniline,
2-fluoro-6-[1-(4,6-dimethylpyrimidin-2-yl)-1-chloromethyl]aniline,
2-chloro-6-[1-(4,6-dimethylpyrimidin-2-yl)-1-chloromethyl]aniline,
2-fluoro-6-[1-(4-methoxy-6-methylpyrimidin-2-yl)-1-chloromethyl]aniline,
2-chloro-6-[1-(4-methoxy-6-methylpyrimidin-2-yl)-1-chloromethyl]aniline,
2-fluoro-6-[1-(4-methoxy-6-trifluoromethylpyrimidin-2-yl)-1-chloromethyl]aniline,
2-chloro-6-[1-(4-methoxy-6-trifluoromethylpyrimidin-2-yl)-1-chloromethyl]aniline,
3-fluoro-6-[1-(4-methoxy-6-methylpyrimidin-2-yl)-1-chloromethyl]aniline,
3-chloro-6-[1-(4-methoxy-6-methylpyrimidin-2-yl)-1-chloromethyl]aniline,
2-fluoro-6-[1-(4,6-dimethylpyrimidin-2-yl)-1-chloromethyl]aniline,
2-chloro-6-[1-(4,6-dimethylpyrimidin-2-yl)-1-chloromethyl]aniline,
2-fluoro-6-[1-(4,6-dimethoxypyrimidin-2-yl)-1-chloroethyl]aniline,
2-chloro-6-[1-(4,6-dimethoxypyrimidin-2-yl)-1-chloroethyl]aniline,
2-fluoro-6-[1-(4,6-dimethylpyrimidin-2-yl)-1-chloroethyl]aniline,
2-chloro-6-[1-(4,6-dimethylpyrimidin-2-yl)-1-chloroethyl]aniline,
2-fluoro-6-[1-(4,6-dimethoxytriazin-2-yl)-1-chloromethyl]aniline,
2-chloro-6-[1-(4,6-dimethoxytriazin-2-yl)-1-chloromethyl]aniline,
2-fluoro-6-[1-(4,6-dimethyltriazin-2-yl)-1-chloromethyl]aniline,
2-chloro-6-[1-(4,6-dimethyltriazin-2-yl)-1-chloromethyl]aniline, 2,3-difluoro-6-[1-(4,6-dimethoxytriazin-2-yl)-1-chloromethyl]aniline,
2,4-dichloro-6-[1-(4,6-dimethoxytriazin-2-yl)-1-chloromethyl]aniline,
2-fluoro-6-[1-(4,6-dimethoxytriazin-2-yl)-1-chloroethyl]aniline,
2-chloro-6-[1-(4,6-dimethoxytriazin-2-yl)-1-chloroethyl]aniline,
2-fluoro-6-[1-(4,6-dimethyltriazin-2-yl)-1-chloroethyl]aniline,
2-chloro-6-[1-(4,6-dimethyltriazin-2-yl)-1-chloroethyl]aniline,
2-fluoro-6-[1-(4,6-dimethoxypyrimidin-2-yl)-1-fluoromethyl]aniline,
2-chloro-6-[1-(4,6-dimethoxypyrimidin-2-yl)-1-fluoromethyl]aniline,
2,3-difluoro-6-[1-(4,6-dimethoxypyrimidin-2-yl)-1-fluoromethyl]aniline,
2,3-dichloro-6-[1-(4,6-dimethoxypyrimidin-2-yl)-1-fluoromethyl]aniline,
2-fluoro-3-chloro-6-[1-(4,6-dimethoxypyrimidin-2-yl)-1-fluoromethyl]aniline,
3-fluoro-2-chloro-6-[1-(4,6-dimethoxypyrimidin-2-yl)-1-fluoromethyl]aniline,
2,4-difluoro-6-[1-(4,6-dimethoxypyrimidin-2-yl)-1-fluoromethyl]aniline,
2,4-dichloro-6-[1-(4,6-dimethoxypyrimidin-2-yl)-1-fluoromethyl]aniline,
2-fluoro-4-chloro-6-[1-(4,6-dimethoxypyrimidin-2-yl)-1-fluoromethyl]aniline,
4-fluoro-2-chloro-6-[1-(4,6-dimethoxypyrimidin-2-yl)-1-fluoromethyl]aniline,
2,5-difluoro-6-[1-(4,6-dimethoxypyrimidin-2-yl)-1-fluoromethyl]aniline,
2,5-dichloro-6-[1-(4,6-dimethoxypyrimidin-2-yl)-1-fluoromethyl]aniline,
2-fluoro-5-chloro-6-[1-(4,6-dimethoxypyrimidin-2-yl)-1-fluoromethyl]aniline,
5-fluoro-2-chloro-6-[1-(4,6-dimethoxypyrimidin-2-yl)-1-fluoromethyl]aniline,
2-fluoro-6-[1-(4,6-dimethylpyrimidin-2-yl)-1-fluoromethyl]aniline,
2-chloro-6-[1-(4,6-dimethylpyrimidin-2-yl)-1-fluoromethyl]aniline,
2-fluoro-6-[1-(4-methoxy-6-methylpyrimidin-2-yl)-1-fluoromethyl]aniline,
2-chloro-6-[1-(4-methoxy-6-methylpyrimidin-2-yl)-1-fluoromethyl]aniline,
2-fluoro-6-[1-(4-methoxy-6-trifluoromethylpyrimidin-2-yl)-1-fluoromethyl]aniline,
2-chloro-6-[1-(4-methoxy-6-trifluoromethylpyrimidin-2-yl)-1-fluoromethyl]aniline,
3-fluoro-6-[1-(4-methoxy-6-methylpyrimidin-2-yl)-1-fluoromethyl]aniline,
3-chloro-6-[1-(4-methoxy-6-methylpyrimidin-2-yl)-1-fluoromethyl]aniline,
2-fluoro-6-[1-(4,6-dimethoxytriazin-2-yl)-1-fluoromethyl]aniline,
2-chloro-6-[1-(4,6-dimethoxytriazin-2-yl)-1-fluoromethyl]aniline,
2,3-difluoro-6-[1-(4,6-dimethoxypyridin-2-yl)-1-fluoromethyl]aniline,
2,3-dichloro-6-[1-(4,6-dimethoxypyridin-2-yl)-1-fluoromethyl]aniline, and so on Difluoromethanesulfonyl chloride, that reacts with the compounds of the above-mentioned formula (II) in the aforementioned preparation process (a), is a per se known substance.

The compounds of the formula (IAb), used as the starting materials in the aforementioned preparation process (b), correspond to a part of the compounds of the formula (IA) of the present invention, that can be prepared by the aforementioned preparation processes (a), (c), (d), (e), (f), (g) or (h). As their specific examples there can be mentioned as follows:
2-fluoro-6-[1-(4,6-dimethoxypyrimidin-2-yl)-1-methylthiomethyl]-N-difluoromethanesulfonanilide,
2-fluoro-6-[1-(4,6-dimethoxypyrimidin-2-yl)-1-methylthioethyl]-N-difluoromethanesulfonanilide,
2-fluoro-3-chloro-6-[1-(4,6-dimethoxypyrimidin-2-yl)-1-methylthiomethyl]-N-difluoromethanesulfonanilide,
2-chloro-6-[1-(4,6-dimethoxypyrimidin-2-yl)-1-methylthiomethyl]-N-difluoromethanesulfonanilide,
2-chloro-6-[1-(4,6-dimethoxypyrimidin-2-yl)ethyl]-N-difluoromethanesulfonanilide,
2,3-difluoro-6-[(4,6-dimethoxypyrimidin-2-yl)methyl]-N-difluoromethanesulfonanilide,
2-fluoro-5-chloro-6-[(4,6-dimethoxypyrimidin-2-yl)methyl]-N-difluoromethanesulfonanilide,
2,4-dichloro-6-[(4,6-dimethoxypyrimidin-2-yl)carbonyl]-N-difluoromethanesulfonanilide,
3,5-dichloro-6-[(4,6-dimethoxypyrimidin-2-yl)carbonyl]-N-difluoromethanesulfonanilide,
2-fluoro-6-[1-(4,6-dimethoxypyrimidin-2-yl)-1-methyl-1-hydroxyethyl]-N-difluoromethanesulfonanilide,
2-chloro-6-[1-(4,6-dimethoxytriazin-2-yl)-1-fluoromethyl]-N-difluoromethanesulfonanilide,
2-fluoro-6-[1-(4,6-dimethoxypyrimidin-2-yl)-1-fluoromethyl]-N-difluoromethanesulfonanilide,
2-[1-(4,6-dimethoxytriazin-2-yl)-1-fluoromethyl]-6-methyl-N-difluoromethanesulfonanilide, and so on.

The compounds of the formula (III), that react with the compounds of the above-mentioned formula (IAb) in the aforementioned preparation process (b), are per se known substances and as their specific examples there can be mentioned as follows:
methyl iodide, ethyl iodide, 1,1,1-trifluoro-2-iodoethane, chloromethyl methyl ether, chloromethyl ethyl ether, methyl bromoacetate, methyl bromopropionate, acetyl chloride, propionyl chloride, cyclopropanecarbonyl chloride, 2,2-dichloro-1-ethyl-3-methyl-cyclopropanecarbonyl chloride, methyl chloroformate, ethyl chloroformate, propyl chloroformate, isopropyl chloroformate, etc., methanesulfonyl chloride, chloromethanesulfonyl chloride, difluoromethanesulfonyl chloride, trifluoromethanesulfonyl chloride, 2,2,2-trifluoroethanesulfonyl chloride, cyanomethylsulfonyl chloride, N,N-dimethylsulfamoyl chloride, methyl 2,2-difluoro-2-(fluorosulfonyl)acetate, etc.; acetic anhydride, trifluoroacetic anhydride, methanesulfonic anhydride, trifluoromethanesulfonic anhydride, etc.; acetic acid, cyclohexane carboxylic acid, 2,2-dichloro-1-methylcyclopropane-carboxylic acid, etc.; methanol, ethanol, 2,2,2-trifluoroethanol, and so on.

The compounds of the formula (IAc), used as the starting materials in the aforementioned preparation process (c), correspond to a part of the compounds of the formula (IA) of the present invention, that can be prepared by the aforementioned preparation processes (a) or (b) and as their specific examples there can be mentioned as follows:
2-fluoro-6-[1-(4,6-dimethoxypyrimidin-2-yl)-1-methylthiomethyl]-N-difluoromethanesulfonanilide, 2-fluoro-6-[1-(4,6-dimethoxypyrimidin-2-yl)-1-methylthio-ethyl]-N-difluoromethanesulfonanilide,
2-fluoro-3-chloro-6-[1-(4,6-dimethoxypyrimidin-2-yl)-1-methylthiomethyl]-N-difluoromethanesulfonanilide,
2-chloro-6-[1-(4,6-dimethoxypyrimidin-2-yl)-1-methylthiomethyl]-N-difluoromethanesulfonanilide,
2-chloro-6-[1-(4,6-dimethoxypyrimidin-2-yl)-1-methylthiomethyl]-N-methyl-N-difluoromethanesulfonanilide,
2-chloro-6-[1-(4,6-dimethoxypyrimidin-2-yl)-1-methylthiomethyl]-N-acetyl-N-difluoromethanesulfonanilide,
2-fluoro-6-[1-(4,6-dimethoxypyrimidin-2-yl)-1-methylthiomethyl]-N-trifluoroacetyl-N-difluoromethanesulfonanilide,
2-fluoro-6-[1-(4,6-dimethoxypyrimidin-2-yl)-1-methylthiomethyl]-N-methylmethoxy-N-difluoromethanesulfonanilide,
2-fluoro-6-[1-(4,6-dimethoxytriazin-2-yl)-1-methylthiomethyl]-N-methyl-N-difluoromethanesulfonanilide,
2-fluoro-6-[1-(4,6-dimethoxytriazin-2-yl)-1-methylthiomethyl]-N-acetyl-N-difluoromethanesulfonanilide, and so on As the reducing agent used to substitute —SR$^8$ in the compounds of the above-mentioned formula (IAc) in the aforementioned preparation process (c) with hydrogen there can be mentioned, for example, combination of sodium borohydride and nickel (II) chloride, or Raney nickel, etc.

The compounds of the formula (IAd), used as the starting materials in the aforementioned preparation process (d), correspond to a part of the compounds of the formula (IA) of the present invention, that can be prepared by the aforementioned preparation processes (a), (b) or (c) and as their specific examples there can be mentioned as follows:
2,3-difluoro-6-[(4,6-dimethoxypyrimidin-2-yl)methyl]-N-difluoromethanesulfonanilide,
2-fluoro-5-chloro-6-[(4,6-dimethoxypyrimidin-2-yl)methyl]-N-difluoromethanesulfonanilide,
2-chloro-6-[(4,6-dimethoxypyrimidin-2-yl)methyl]-N-methyl-N-difluoromethanesulfonanilide,
2-chloro-6-[(4,6-dimethoxypyrimidin-2-yl)methyl]-N-acetyl-N-difluoromethanesulfonanilide,
2-fluoro-6-[(4,6-dimethoxypyrimidin-2-yl)methyl]-N-trifluoroacetyl-N-difluoromethanesulfonanilide,
2-fluoro-6-[(4,6-dimethoxypyrimidin-2-yl)methyl]-N-methylmethoxy-N-difluoromethanesulfonanilide,
2-fluoro-6-[(4,6-dimethoxytriazin-2-yl)methyl]-N-methyl-N-difluoromethanesulfonanilide,
2-fluoro-6-[(4,6-dimethoxytriazin-2-yl)methyl]-N-acetyl-N-difluoromethanesulfonanilide, and so on.

As the oxidizing agent used to convert methylene (—CH$_2$—) in the compounds of the above-mentioned formula (IAd) in the aforementioned preparation process (d) into carbonyl (═CO) through oxidation there can be mentioned, for example, chromium (VI) oxide, manganese dioxide, selenium dioxide, etc.

The compounds of the formula (IAe), used as the starting materials in the aforementioned preparation process (e) or the aforementioned preparation process (f), correspond to a part of the compounds of the formula (IA) of the present invention, that can be prepared by the aforementioned preparation processes (a), (b) or (d) and as their specific examples there can be mentioned as follows:
2,4-dichloro-6-[(4,6-dimethoxypyrimidin-2-yl)carbonyl]-N-difluoromethanesulfonanilide,
3,5-dichloro-6-[(4,6-dimethoxypyrimidin-2-yl)carbonyl]-N-difluoromethanesulfonanilide,
2-chloro-6-[(4,6-dimethoxypyrimidin-2-yl)carbonyl]-N-methyl-N-difluoromethanesulfonanilide,
2-chloro-6-[(4,6-dimethoxypyrimidin-2-yl)carbonyl]-N-acetyl-N-difluoromethanesulfonanilide,
2-fluoro-6-[(4,6-dimethoxypyrimidin-2-yl)carbonyl]-N-trifluoroacetyl-N-difluoromethanesulfonanilide,
2-fluoro-6-[(4,6-dimethoxypyrimidin-2-yl)carbonyl]-N-methylmethoxy-N-difluoromethanesulfonanilide,
2-fluoro-6-[(4,6-dimethoxytriazin-2-yl)carbonyl]-N-methyl-N-difluoromethanesulfonanilide,
2-fluoro-6-[(4,6-dimethoxytriazin-2-yl)carbonyl]-N-acetyl-N-difluoromethanesulfonanilide, and so The compounds of the formula (IV), that react with the compounds of the above-mentioned formula (IAe) in the aforementioned preparation process (e), are per se known substances and, for example, as their specific examples there can be mentioned the following:
methyl magnesium bromide, ethyl magnesium bromide, vinyl magnesium chloride, allyl magnesium bromide, etc.

As the alkaline metal hydride complex compound or borane complex used for the reduction of carbonyl (═CO) in the compounds of the above-mentioned formula (IAe) in the aforementioned preparation process (f) there can be mentioned, for example, sodium borohydride, lithium aluminium hydride, dimethyl sulfide borane, pyridine-borane, etc.

The compounds of the formula (IAg), used as the starting materials in the aforementioned preparation process (g), correspond to a part of the compounds of the formula (IA) of the present invention, that can be prepared by the aforementioned preparation processes (a), (b), (f) or (e) and as their specific examples there can be mentioned as follows:
2-fluoro-6-[1-(4,6-dimethoxypyrimidin-2-yl)-1-hydroxyethyl]-N-difluoromethanesulfonanilide,
2-chloro-6-[1-(4,6-dimethoxypyrimidin-2-yl)-1-hydroxymethyl]-N-methyl-N-difluoromethanesulfonanilide,
2-chloro-6-[1-(4,6-dimethoxypyrimidin-2-yl)-1-hydroxymethyl]-N-acetyl-N-difluoromethanesulfonanilide,
2-fluoro-6-[1-(4,6-dimethoxypyrimidin-2-yl)-1-hydroxymethyl]-N-trifluoroacetyl-N-difluoromethanesulfonanilide,
2-fluoro-6-[1-(4,6-dimethoxypyrimidin-2-yl)-1-hydroxymethyl]-N-methylmethoxy-N-difluoromethanesulfonanilide,
2-fluoro-6-[1-(4,6-dimethoxytriazin-2-yl)-1-hydroxymethyl]-N-methyl-N-difluoromethanesulfonanilide,
2-fluoro-6-[1-(4,6-dimethoxytriazin-2-yl)-1-hydroxymethyl]-N-acetyl-N-difluoromethanesulfonanilide, and so on.

As the halogenating agent used for the halogenation of the compounds of the above-mentioned formula (IAg) in the aforementioned preparation process (g) there can be mentioned, for example, diethylamine sulfur trifluoride, phosphorus oxychloride, thionyl chloride, etc.

The compounds of the formula (IAh), used as the starting materials in the aforementioned preparation process (h), correspond to a part of the compounds of the formula (IA) of the present invention, that can be prepared by the aforementioned preparation process (g) and as their specific examples there can be mentioned as follows:
2-fluoro-6-[1-(4,6-dimethoxypyrimidin-2-yl)-1-chloromethyl]-N-difluoromethanesulfonanilide,
2-fluoro-6-[1-(4,6-dimethoxypyrimidin-2-yl)-1-chloroethyl]-N-difluoromethanesulfonanilide,
2-[1-(4,6-dimethoxypyrimidin-2-yl)-1-chloromethyl]-6-methyl-N-difluoromethanesulfonanilide,
2-chloro-6-[1-(4,6-dimethoxypyrimidin-2-yl)-1-chloromethyl]-N-methyl-N-difluoromethanesulfonanilide,
2-chloro-6-[1-(4,6-dimethoxypyrimidin-2-yl)-1-chloromethyl]-N-acetyl-N-difluoromethanesulfonanilide, 2-fluoro-6-[1-(4,6-dimethoxypyrimidin-2-yl)-1-chloromethyl]-N-trifluoroacetyl-N-difluoromethanesulfonanilide,
2-fluoro-6-[1-(4,6-dimethoxypyrimidin-2-yl)-1-chloromethyl]-N-methylmethoxy-N-difluoromethanesulfonanilide,
2-fluoro-6-[1-(4,6-dimethoxytriazin-2-yl)-1-chloromethyl]-N-methyl-N-difluoromethanesulfonanilide,
2-fluoro-6-[1-(4,6-dimethoxytriazin-2-yl)-1-chloromethyl]-N-acetyl-N-difluoromethanesulfonanilide, and so on.

The compounds of the formula (V), that react with the compounds of the above-mentioned formula (IAh) in the aforementioned preparation process (h), are per se known substances and as their specific examples there can be mentioned as follows:
sodium methoxide, sodium ethoxide, sodium thiomethoxide, sodium thioethoxide, sodium thiopropanol, and so on.

The reaction of the above-mentioned preparation process (a) can be conducted in an appropriate diluent. As examples of the diluent used in that case there can be mentioned aliphatic, alicyclic and aromatic hydrocarbons (may be optionally chlorinated), for example, pentane, hexane, cyclohexane, petroleum ether, ligroine, benzene, toluene, xylene, dichloromethane, chloroform, carbon tetrachloride, 1,2-dichloroethane, chlorobenzene, dichlorobenzene, etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM), etc.; ketones, for example, acetone, methyl ethyl ketone (MEK), methyl-isopropyl ketone, methyl isobutyl ketone (MIBK), etc.; nitriles, for example, acetonitrile, propionitrile, etc.; esters, for example, ethyl acetate, amyl acetate, etc.; bases, for example, pyridine etc.

The preparation process (a) can be conducted in the presence of an acid binder, and as said acid binder there can be mentioned as inorganic bases, hydrides, hydroxides, carbonates, bicarbonates, etc. of alkali metals or alkaline earth metals, for example, sodium hydride, lithium hydride, sodium hydrogen carbonate, potassium hydrogen carbonate, sodium carbonate, potassium carbonate, lithium hydroxide, sodium hydroxide, potassium hydroxide, calcium hydroxide, etc.; inorganic alkali metal amides, for example, lithium amide, sodium amide, potassium amide, etc.; as organic bases, tertiary amines, dialkylaminoanilines and pyridines, for example, triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO) and 1,8-diazabicyclo[5,4,0]undec-7-ene (DBU), etc.

The preparation process (a) can be conducted in a substantially wide range of temperature. It is, however, preferable to conduct it at temperatures in the range of generally about −100 to about 60° C., particularly about −80 to about 40° C. Although said reaction is conducted desirably under normal pressure, it can be conducted optionally under elevated pressure or under reduced pressure.

In conducting the preparation process (a), the aimed compound can be obtained, for example, by reacting 1 to 5 moles of difluoromethanesulfonyl chloride to 1 mole of the compound of the formula (II) in a diluent, for example, dichloromethane in the presence of 1 to 5 moles of pyridine.

The reaction of the above-mentioned preparation process (b) can be conducted in an appropriate diluent. As examples of the diluent used in that case there can be mentioned aliphatic, alicyclic and aromatic hydrocarbons (may be optionally chlorinated), for example, hexane, cyclohexane, ligroine, toluene, xylene, dichloromethane, chloroform, carbon tetrachloride, 1,2-dichloroethane, chlorobenzene, etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM), etc.; ketones, for example, acetone, methyl ethyl ketone (MEK), methyl-isopropyl ketone, methyl isobutyl ketone (MIBK), etc.; nitriles, for example, acetonitrile, propionitrile, acrylonitrile, etc.; esters, for example, ethyl acetate, amyl acetate, etc.; acid amides, for example, dimethylformamide (DMF), dimethylacetamide (DMA), N-methylpyrrolidone, 1,3-dimethyl-2-imidazolidinone, hexamethylphosphoric triamide (HMPA), etc.; sulfones, sulfoxides, for example, dimethyl sulfoxide (DMSO), sulfolane, etc.; bases, for example, pyridine etc.

The preparation process (b) can be conducted in the presence of an acid binder, and as said acid binder there can be mentioned as inorganic bases, hydrides, hydroxides, carbonates, bicarbonates, etc. of alkali metals or alkaline earth metals, for example, sodium hydride, lithium hydride, sodium hydrogen carbonate, potassium hydrogen carbonate, sodium carbonate, potassium carbonate, lithium hydroxide, sodium hydroxide, potassium hydroxide, calcium hydroxide, etc.; inorganic alkali metal amides, for example, lithium amide, sodium amide, potassium amide, etc.; as organic bases, alcoholates, tertiary amines, dialkylaminoanilines and pyridines, for example, triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO) and 1,8-diazabicyclo[5,4,0]undec-7-ene (DBU), etc.; organic lithium compounds, for example, methyl lithium, n-butyl lithium, sec-butyl lithium, tert-butyl lithium, phenyl lithium, dimethyl copper lithium, lithium diisopropyl amide, lithium cyclohexyl isopropyl amide, lithium dicyclohexyl amide, n-butyl lithium.DABCO, n-butyl lithium.DBU, n-butyl lithium.TMEDA, etc.

The preparation process (b) can be conducted in a substantially wide range of temperature. It is, however, preferable to conduct it at temperatures in the range of generally about −100 to about 130° C., particularly about −80 to about 130° C. Although said reaction is conducted desirably under normal pressure, it can be conducted optionally under elevated pressure or under reduced pressure.

In conducting the preparation process (b), the aimed compound can be obtained, for example, by reacting 1 to 5 moles of the compound of the formula (III) to 1 mole of the compound of the formula (IAb) in a diluent, for example, acetonitrile, in the presence of 2 to 5 moles of potassium carbonate.

In case that $R^{6A}$ represents acyl or group $SO_2R^{5A}$ in the formula (III), acid anhydrides derived from the compounds of the corresponding formula (III) can be used, and in case that $R^{6A}$ represents acyl, carboxylic acids derived from the compounds of the corresponding formula (III) can be used in the presence of a condensing agent, for example, 1,1-carbonyldiimidazole (CDI), 1,3-dicyclohexylcarbodiimide, (DCC), 1-(3-dimethyldiaminopropyl)-3-ethylcarbodiimide hydrochloride (WSC), benzotriazol-1-yloxy-tris(dimethylamino) phosphonium hexafluorophosphate (BOP), etc., and further, in case that $R^{6A}$ represents alkoxycarbonyl, the corresponding alcohol and a condensing agent, for example, 1,1-carbonyldiimidazole (CDI) can be used, to obtain each objective compound.

The reaction of the above-mentioned preparation process (c) can be conducted in an appropriate diluent. As examples of the diluent used in that case there can be mentioned aliphatic, alicyclic and aromatic hydrocarbons (may be optionally chlorinated), for example, hexane, cyclohexane, ligroine, toluene, xylene, dichloromethane, chloroform, carbon tetrachloride, 1,2-dichloroethane, chlorobenzene, etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM), etc.; alcohols, for example, methanol, ethanol, isopropanol, butanol, ethylene glycol, etc.; acids, for example, acetic acid etc.

The preparation process (c) can be conducted in a substantially wide range of temperature. It is, however, preferable to conduct it at temperatures in the range of generally about −100 to about 80° C., particularly about −80 to about 80° C. Although said reaction is conducted desirably under normal pressure, it can be conducted optionally under elevated pressure or under reduced pressure.

In conducting the preparation process (c), the aimed compound can be obtained, for example, by reacting 1 to 8 moles of sodium borohydride to 1 mole of the compound of the formula (IAc) in a diluent, for example, methanol, in the presence of 1 to 8 moles of nickel (II) chloride hexahydrate.

The reaction of the above-mentioned preparation process (d) can be conducted in an appropriate diluent. As examples of the diluent used in that case there can be mentioned water; aliphatic, alicyclic and aromatic hydrocarbons (may be optionally chlorinated), for example, hexane, cyclohexane, ligroine, toluene, xylene, dichloromethane, chloroform, carbon tetrachloride, 1,2-dichloroethane, chlorobenzene, etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM), etc.; ketones, for example, acetone, methyl ethyl ketone (MEK), methyl-isopropyl ketone, methyl isobutyl ketone (MIBK), etc.; nitriles, for example, acetonitrile, propionitrile, acrylonitrile, etc.; esters, for example, ethyl acetate, amyl acetate, etc.; acid amides, for example, dimethylformamide (DMF), dimethylacetamide (DMA), N-methylpyrrolidone, 1,3-dimethyl-2-imidazolidinone, hexamethylphosphoric triamide (HMPA), etc.; sulfones, sulfoxides, for example, dimethyl sulfoxide (DMSO), sulfolane, etc.; bases, for example, pyridine etc.

The preparation process (d) can be conducted in the presence of an acid catalyst and as examples of said acid catalyst there can be mentioned mineral acids, for example, hydrochloric acid, sulfuric acid, nitric acid, hydrobromic acid, sodium hydrogen sulfite, etc.; organic acids, for example, formic acid, acetic acid, trifluoroacetic acid, propionic acid, methanesulfonic acid, benzenesulfonic acid, p-toluenesulfonic acid, etc.

The preparation process (d) can be conducted in a substantially wide range of temperature. It is, however, preferable to conduct it at temperatures in the range of generally about −100 to about 150° C., particularly about 20 to about 120° C. Although said reaction is conducted desirably under normal pressure, it can be conducted optionally under elevated pressure or under reduced pressure.

In conducting the preparation process (d), the aimed compound can be obtained, for example, by reacting 1 to 10 moles of chromium (VI) oxide to 1 mole of the compound of the formula (IAd) in a diluent, for example, acetic acid.

The reaction of the above-mentioned preparation process (e) can be conducted in an appropriate diluent. As examples of the diluent used in that case there can be mentioned ethers, for example, ethyl ether, methyl ethyl ether, isopropyl ether, butyl ether, dioxane, dimethoxyethane (DME), tetrahydrofuran (THF), diethylene glycol dimethyl ether (DGM), etc.;

The preparation process (e) can be conducted in a substantially wide range of temperature. It is, however, preferable to conduct it at temperatures in the range of generally about −100 to about 60° C., particularly about −80 to about 30° C. Although said reaction is conducted desirably under normal pressure, it can be conducted optionally under elevated pressure or under reduced pressure.

In conducting the preparation process (e), the aimed compound can be obtained, for example, by reacting 1 to 4 moles of the compound of the formula (IV) to 1 mole of a compound of the formula (IAe) in a diluent, for example, tetrahydrofuran.

The reaction of the above-mentioned preparation process (f) can be conducted in an appropriate diluent. As examples of the diluent used in that case there can be mentioned water; aliphatic, alicyclic and aromatic hydrocarbons (may be optionally chlorinated), for example, pentane, hexane, cyclohexane, petroleum ether, ligroine, benzene, toluene, xylene, dichloromethane, chloroform, carbon tetrachloride, 1,2-dichloroethane, chlorobenzene, dichlorobenzene, etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM), etc.; nitriles, for example, acetonitrile, propionitrile, etc.; alcohols, for example, methanol, ethanol, isopropanol, butanol, ethylene glycol, etc.; esters, for example, ethyl acetate, amyl acetate, etc.; acid amides, for example, dimethylformamide (DMF), dimethylacetamide (DMA), N-methylpyrrolidone, 1,3-dimethyl-2-imidazolidinone, hexamethylphosphoric triamide (HMPA), etc.; sulfones, sulfoxides, for example, dimethyl sulfoxide (DMSO), sulfolane, etc.; bases, for example, pyridine etc.

The preparation process (f) can be conducted in a substantially wide range of temperature. It is, however, preferable to conduct it at temperatures in the range of generally about −100 to about 60° C., particularly about −80 to about 40° C. Although said reaction is conducted desirably under normal pressure, it can be conducted optionally under elevated pressure or under reduced pressure.

In conducting the preparation process (f), the aimed compound can be obtained, for example, by reacting 0.25 to 2 moles of sodium borohydride to 1 mole of the compound of the formula (IAe) in a diluent, for example, methanol.

The reaction of the above-mentioned preparation process (g) can be conducted in an appropriate diluent. As examples of the diluent used in that case there can be mentioned aliphatic, alicyclic and aromatic hydrocarbons (may be optionally chlorinated), for example, hexane, cyclohexane, ligroine, toluene, xylene, dichloromethane, chloroform, carbon tetrachloride, 1,2-dichloroethane, chlorobenzene, etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM), etc. in case that a fluorinating agent, for example, the aforementioned diethylamine sulfur trifluoride etc. is used as a halogenating agent, and there can be mentioned aliphatic, alicyclic and aromatic hydrocarbons (may be optionally chlorinated), for example, hexane, cyclohexane, ligroine, benzene, toluene, xylene, dichloromethane, chloroform, carbon tetrachloride, 1,2-dichloroethane, chlorobenzene, etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM), etc.; acid amides, for example, dimethylformamide (DMF), dimethylacetamide (DMA), N-methylpyrrolidone, 1,3-dimethyl-2-imidazolidinone, hexamethylphosphoric triamide (HMPA), etc. in case that a chlorinating agent, for example, the aforementioned phosphorus oxychloride, thionyl chloride, etc. is used as a halogenating agent.

The preparation process (g) can be conducted in a substantially wide range of temperature. It is preferable to conduct it at temperatures, for example, in the range of generally about −100 to about 30° C., particularly about −80 to about 30° C. in case that the aforementioned fluorinating agents are used as halogenating agent. Although said reaction is conducted desirably under normal pressure, it can be conducted optionally under elevated pressure or under reduced pressure.

In case that the aforementioned chlorinating agents are used as halogenating agent, it is preferable to conduct it at temperatures in the range of generally about −100 to about 130° C., particularly about −80 to about 130° C. Although said reaction is conducted desirably under normal pressure, it can be conducted optionally under elevated pressure or under reduced pressure.

In conducting the preparation process (g), the aimed compound can be obtained, for example, by reacting 1 to 5 moles of diethylamine sulfur trifluoride to 1 mole of the compound of the formula (IAg) in a diluent, for example, dichloromethane.

Further, in conducting the preparation process (g), the aimed compound can be obtained, for example, by reacting 1 mole to such an amount as to be used itself as solvent of thionyl chloride to 1 mole of the compound of the formula (IAg) in a diluent, for example, dichloromethane.

The reaction of the above-mentioned preparation process (h) can be conducted in an appropriate diluent. As examples of the diluent used in that case there can be mentioned water; aliphatic, alicyclic and aromatic hydrocarbons (may be optionally chlorinated), for example, hexane, cyclohexane, ligroine, toluene, xylene, dichloromethane, chloroform, carbon tetrachloride, 1,2-dichloroethane, chlorobenzene, etc.; ethers, for example, ethyl ether, methyl ethyl ether, isopropyl ether, butyl ether, dioxane, dimethoxyethane (DME), tetrahydrofuran (THE), diethylene glycol dimethyl ether (DGM), etc.; nitriles, for example, acetonitrile, propionitrile, acrylonitrile, etc.; esters, for example, ethyl acetate, amyl acetate, etc.; acid amides, for example, dimethylformamide (DMF), dimethylacetamide (DMA), N-methylpyrrolidone, 1,3-dimethyl-2-imidazolidinone, hexamethylphosphoric triamide (HMPA), etc.; sulfones, sulfoxides, for example, dimethyl sulfoxide (DMSO), sulfolane, etc.; bases, for example, pyridine etc.

The preparation process (h) can be conducted in the presence of an acid binder, and as said acid binder there can be mentioned as inorganic bases, hydrides, hydroxides, carbonates, bicarbonates, etc. of alkali metals or alkaline earth metals, for example, sodium hydride, lithium hydride, sodium hydrogen carbonate, potassium hydrogen carbonate, sodium carbonate, potassium carbonate, lithium hydroxide, sodium hydroxide, potassium hydroxide, calcium hydroxide, etc.; inorganic alkali metal amides, for example, lithium amide, sodium amide, potassium amide, etc.; as organic bases, tertiary amines, dialkylaminoanilines and pyridines, for example, triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO) and 1,8-diazabicyclo[5,4,0]undec-7-ene (DBU), etc.; organic lithium compounds, for example, methyl lithium, n-butyl lithium, sec-butyl lithium, tert-butyl lithium, phenyl lithium, dimethyl copper lithium, lithium diisopropyl amide, lithium cyclohexyl isopropyl amide, lithium dicyclohexyl amide, n-butyl lithium.DABCO, n-butyl lithium.DBU, n-butyl lithium.TMEDA, etc.

The preparation process (h) can be conducted in a substantially wide range of temperature. It is, however, preferable to conduct it at temperatures in the range of generally of about −100 to about 130° C., preferably about −80 to about 130° C. Although said reaction is conducted desirably under normal pressure, it can be conducted optionally under elevated pressure or under reduced pressure.

In conducting the preparation process (h), the aimed compound can be obtained, for example, by reacting 1 to 3 moles of the compound of the formula (V) to 1 mole of a compound of the formula (IAh) in a diluent, for example, N,N-dimethylformamide.

The active component compounds of the formula (I), according to the present invention, show a strong germicidal action and in fact, they can be used to control undesirable plant pathogens.

The active component compounds of the formula (I), according to the present invention, can be used generally as germicidal agents against various plant diseases by Plasmodiophoromycetes, Oomycetes, Zygomycetes, Ascomycetes, Basidiomycetes or Deuteromycetes, and show excellent controlling effect particularly against such plant pathogens as *Pyricularia oryzae*, *Botrytis cinerea*, etc.

Some pathogens causing fungal diseases which come under the generic names listed above are mentioned as example but not by way of limitation:

Powdery Mildew Diseases such as
*Blumeria* diseases caused for example by *Blumeria graminis*
*Podosphaera* diseases caused for example by *Podosphaera leucotricha*
*Sphaerotheca* diseases caused for example by *Sphaerotheca fuliginea*
*Uncinula* diseases caused for example by *Uncinula necator*
Rust Diseases such as
*Gymnosporangium* diseases caused for example by *Gymnosporangium sabinae*
*Hemileia* diseases caused for example by *Hemileia vastatrix*
*Phakopsora* diseases caused for example by *Phakopsora pachyrhizi*
*Puccinia* diseases caused for example by *Puccinia recondita*;
*Uromyces* diseases caused for example by *Uromyces appendiculatus*;
Oomycete Diseases such as
*Bremia* diseases caused for example by *Bremia lactucae*
*Peronospora* diseases caused for example by *Peronospora brassicae*
*Phytophthora* diseases caused for example by *Phytophthora infestans*
*Plasmopara* diseases caused for example by *Plasmopara viticola*
*Pseudoperonospora* diseases caused for example by *Pseudoperonospora cubensis*
*Pythium* diseases caused for example by *Pythium ultimum*
Leafspot, Leaf blotch and Leaf Blight Diseases such as
*Alternaria* diseases caused for example by *Alternaria solani*
*Cercospora* diseases caused for example by *Cercospora beticola*
*Cladiosporium* diseases caused for example by *Cladiosporium cucumerinum*
*Cochliobolus* diseases caused for example by *Cochliobolus sativus*
*Colletotrichum* diseases caused for example by *Colletotrichum lindemuthianum*
*Cycloconium* diseases caused for example by *Cycloconium oleaginum*
*Diaporthe* diseases caused for example by *Diaporthe citri*
*Elsinoe* diseases caused for example by *Elsinoe fawcettii*
*Gloeosporium* diseases caused for example by *Gloeosporium laeticolor*
*Glomerella* diseases caused for example by *Glomerella cingulata*

*Guignardia* diseases caused for example by *Guignardia bidwellii*
*Leptosphaeria* diseases caused for example by *Leptosphaeria maculans*
*Magnaporthe* diseases caused for example by *Magnaporthe grisea*
*Mycosphaerella* diseases caused for example by *Mycosphaerella graminicola*
*Phaeosphaeria* diseases caused for example by *Phaeosphaeria nodorum*
*Pyrenophora* diseases caused for example by *Pyrenophora teres*
*Ramularia*-diseases caused for example by *Ramularia collocygni*
*Rhynchosporium* diseases caused for example by *Rhynchosporium secalis*
*Septoria* diseases caused for example by *Septoria apii*;
*Typhula* diseases caused for example by *Thyphula incarnata*
*Venturia* diseases caused for example by *Venturia inaequalis*
 Root- and Stem Diseases such as
*Corticium* diseases caused for example by *Corticium graminearum*
*Fusarium* diseases caused for example by *Fusarium oxysporum*
*Gaeumannomyces* diseases caused for example by *Gaeumannomyces graminis*
*Rhizoctonia* diseases caused for example by *Rhizoctonia solani*
*Tapesia* diseases caused for example by *Tapesia acuformis*
*Thielaviopsis* diseases caused for example by *Thielaviopsis basicola*
 Ear and Panicle Diseases such as
*Alternaria* diseases caused for example by *Alternaria* spp.
*Aspergillus* diseases caused for example by *Aspergillus flavus*
*Cladosporium* diseases caused for example by *Cladiosporium* spp.
*Claviceps* diseases caused for example by *Claviceps purpurea*
*Fusarium* diseases caused for example by *Fusarium culmorum*
*Gibberella* diseases caused for example by *Gibberella zeae*
*Monographella* diseases caused for example by *Monographella nivalis*
 Smut- and Bunt Diseases such as
*Sphacelotheca* diseases caused for example by *Sphacelotheca reiliana*
*Tilletia* diseases caused for example by *Tilletia caries*
*Urocystis* diseases caused for example by *Urocystis occulta*
*Ustilago* diseases caused for example by *Ustilago nuda*;
 Fruit Rot and Mould Diseases such as
*Aspergillus* diseases caused for example by *Aspergillus flavus*
*Botrytis* diseases caused for example by *Botrytis cinerea*
*Penicillium* diseases caused for example by *Penicillium expansum*
*Sclerotinia* diseases caused for example by *Sclerotinia sclerotiorum*;
*Verticillium* diseases caused for example by *Verticillium alboatrum*
 Seed- and Soilborne Decay, Mould, Wilt, Rot and Damping-off diseases
*Fusarium* diseases caused for example by *Fusarium culmorum*
*Phytophthora* diseases caused for example by *Phytophthora cactorum*
*Pythium* diseases caused for example by *Pythium ultimum*
*Rhizoctonia* diseases caused for example by *Rhizoctonia solani*
*Sclerotium* diseases caused for example by *Sclerotium rolfsii*
 Canker, Broom and Dieback Diseases such as
*Nectria* diseases caused for example by *Nectria galligena*
 Blight Diseases such as
*Monilinia* diseases caused for example by *Monilinia laxa*
 Leaf Blister or Leaf Curl Diseases such as
*Taphrina* diseases caused for example by *Taphrina deformans*
 Decline Diseases of Wooden Plants such as
Esca diseases caused for example by *Phaeomoniella clamydospora*
 Diseases of Flowers and Seeds such as
*Botrytis* diseases caused for example by *Botrytis cinerea*
 Diseases of Tubers such as
*Rhizoctonia* diseases caused for example by *Rhizoctonia solani*

The active component compounds of the formula (I), according to the present invention, show good compatibility to plants at the concentration of the active compound necessary to control plant pathogens and, in case of using, chemical treatment of aboveground parts of plant, chemical treatment of stocks or seeds, and soil treatment are possible.

The active component compounds of the formula (I), according to the present invention, can be used further, in the protection of various materials, to protect them from infection and destruction by undesirable microorganisms.

In the present specification, the materials are understood to mean inanimate objects manufactured to be widely used.

As the various materials, that can be protected by the active compounds of the present invention from changes or destruction by attack of microorganisms, they can be, for example, adhesives, sizes, paper and cardboard, textiles, leather, wood, paints and synthetic paints, cooling lubricants and other materials that can be infected and destructed by microorganisms. In the scope of materials to be protected there can be included a part of a manufacturing plant, for example, a cooling water circuit that can be damaged by proliferation of microorganisms.

As examples of the microorganisms that cause deterioration or changes of materials there can be mentioned bacteria, molds, yeasts, algae, slime organisms, etc.

As controlling objects, microorganisms of the following genera can be mentioned as examples:
*Alternaria*, for example, *Alternaria tenuis*;
*Aspergillus*, for example, *Aspergillus niger*;
*Chaetomium*, for example, *Chaetomium globosum*;
*Coniophora*, for example, *Coniophora puetana*;
*Lentinus*, for example, *Lentinus tigrinus*;
*Penicillium*, for example, *Penicillium glaucum*;
*Polyporus*, for example, *Polyporus versicolor*;
*Aureobasidium*, for example, *Aureobasidium pullulans*;
*Sclerophoma*, for example, *Sclerophoma pityophila*;
*Trichoderma*, for example, *Trichoderma viride*;
*Escherichia*, for example, *Escherichia coli*;
*Pseudomonas*, for example, *Pseudomonas aeruginosa*;
*Staphylococcus*, for example, *Staphylococcus aureus*, etc.

Moreover, the active compounds of the formula (I), according to the present invention, are low toxic against warm-blooded animals and can be used safely.

The active compounds of the formula (I), according to the present invention, can be formulated into customary formulation forms, in case that they are used as agricultural chemicals. As the formulation forms there can be mentioned, for example, solutions, wettable powders, emulsions, suspensions, powders, foaming agents, pastes, tablets, granules, aerosols, active compound-impregnated natural and synthetic substances, microcapsules, seed coating agents, ULV [cold mist, warm mist], etc.

These formulations can be prepared by per se known methods, for example, by mixing the active compounds with extenders, namely liquid diluents, solid diluents or carriers, and optionally with surface-active agents, namely emulsifiers and/or dispersants and/or foam-forming agents As liquid diluents or carriers there can be generally mentioned aromatic hydrocarbons (for example, xylene, toluene, alkylnaphthalene, etc.), chlorinated aromatic or chlorinated aliphatic hydrocarbons (for example, chlorobenzenes, ethylene chlorides, methylene chloride, etc.), aliphatic hydrocarbons [for example, cyclohexane etc. or paraffins (for example, mineral oil fractions etc.)], alcohols (for example, butanol, glycols etc.) and their ethers, esters, etc., ketones (for example, acetone, methyl ethyl ketone, methyl isobutyl ketone or cyclohexanone, etc.), strongly polar solvents (for example, dimethylformamide, dimethyl sulfoxide, etc.), and water. In case of using water as extender, for example, organic solvents can be used as auxiliary solvents.

As solid diluents there can be mentioned, for example, ground natural minerals (for example, kaolin, clay, talc, chalk, quartz, attapulgite, montmorillonite or diatomaceous earth, etc.), ground synthetic minerals (for example, highly dispersed silicic acid, alumina, silicates, etc.).

As solid carriers for granules there can be mentioned, for example, crushed and fractionated rocks (for example, calcite, marble, pumice, sepiolite, dolomite, etc.) synthetic granules of inorganic or organic meals, particles of organic materials (for example, saw dust, coconut shells, maize cobs, tobacco stalks, etc.), etc As emulsifiers and/or foam-forming agents there can be mentioned, for example, nonionic and anionic emulsifiers [for example, polyoxyethylene fatty acid esters, polyoxyethylene fatty acid alcohol ethers (for example, alkylaryl polyglycol ethers, alkylsulfonates, alkylsulfates, arylsulfonates, etc.)], albumin hydrolysis products, etc.

Dispersants include, for example, lignin sulfite waste liquor, methyl cellulose, etc.

Tackifiers can also be used in preparations (powders, granules, emulsifiable concentrates). As the tackifiers usable in that case there can be mentioned, for example, carboxymethyl cellulose, natural and synthetic polymers (for example, gum Arabic, polyvinyl alcohol, polyvinyl acetate, etc.).

Colorants can also be used. As said colorants there can be mentioned inorganic pigments (for example, iron oxide, titanium oxide, Prussian Blue, etc,), organic dyestuffs such as alizarin dyestuffs, azo dyestuffs or metal phthalocyanine dyestuffs, and further traces nutrients such as iron, manganese, boron, copper, cobalt, molybdenum, zinc or salts of such metals.

Said formulations can contain the active compounds of the formula (I) of the present invention at the ratios in the range of generally 0.1 to 95% by weight, preferably 0.5 to 90% by weight.

The active compounds of the formula (I), according to the present invention, can exist, in the above-mentioned formulations or various application forms, together with other known active compounds, for example, germicides (fungicides, bactericides), insecticides, miticides, nematicides, herbicides, bird repellents, growth regulators, fertilizers and/or soil improvement agents.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

In many cases, synergistic effects are achieved, i.e. the activity of the mixture exceeds the activity of the individual components.

Examples of co-components in mixtures are the following compounds:

Fungicides:
1. Inhibition of Nucleic acid synthesis
1.1 benalaxyl, benalaxyl-M, bupirimate, chiralaxyl, clozylacon, dimethirimol, ethirimol, furalaxyl, hymexazol, metalaxyl-M, ofurace, oxadixyl, oxolinic acid
2. Inhibition of mitosis and cell division:
2.1 benomyl, carbendazim, diethofencarb, fuberidazole, pencycuron, thiabendazole thiophanate-methyl, zoxamide
3. Inhibition of respiration
3.1 CI: diflumetorim
3.2 CII: boscalid, carboxin, fenfuram, flutolanil, furametpyr, mepronil, oxycarboxine, penthiopyrad, thifluzamide
3.3 CIII: azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin,
3.4 Uncouplers: dinocap, fluazinam
3.5 Inhibition of ATP production: fentin acetate, fentin chloride, fentin hydroxide, silthiofam
4. Inhibition of AA and protein biosynthesis
4.1 andoprim, blasticidin-S, cyprodinil, kasugamycin, kasugamycin hydrochloride hydrate, mepanipyrim, pyrimethanil,
5. Inhibition of signal transduction
5.1 fenpiclonil, fludioxonil, quinoxyfen
6. Inhibition of lipids and membranes synthesis
6.1 chlozolinate, iprodione, procymidone, vinclozolin
6.2 pyrazophos, edifenphos, iprobenfos (IBP), isoprothiolane
6.3 tolclofos-methyl, biphenyl
6.4 iodocarb, propamocarb, propamocarb hydrochloride
7. Inhibition of ergosterol Biosynthesis
7.1 fenhexamid,
7.2 azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazol, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole,
7.3 aldimorph, dodemorph, dodemorph acetate, fenpropimorph, tridemorph, fenpropidin, spiroxamine
7.4 naftifine, pyributicarb, terbinafine,
8. Inhibition of cell wall synthesis
8.1 benthiavalicarb, bialaphos, dimethomorph, flumorph, iprovalicarb, polyoxins, polyoxorim, validamycin A
9. Inhibition of melanine biosynthesis
9.1 carpropamid, diclocymet, fenoxanil, phtalide, pyroquilon, tricyclazole,
10. Host defence inducer
10.1 acibenzolar-5-methyl, probenazole, tiadinil
11. Multisite
11.1 captafol, captan, chlorothalonil, copper preparations such as: copper hydroxide, copper naphthenate, copper oxychloride, copper sulphate, copper oxide, oxine-copper and Bordeaux mixture, dichlofluanid, dithianon, dodine, dodine free base, ferbam, fluorofolpet, folpet, guazatine, guazatien acetate, iminoctadine, iminoctadine albesilate, iminoctadine triacetate, mancopper, mancozeb, maneb, metiram, metiram zinc, propineb, sulphur and sulphur preparations including calcium polysulphide, thiram, tolylfluanid, zineb, ziram, 12. Unknown 12.1 amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulphate, diphenylamine, ethaboxam, ferimzone, flumetover, flusulfamide, fosetyl-aluminium, fosetyl-calcium, fosetyl-sodium, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, phosphorous acid and its salts, piperalin, propanosine-sodium, proquinazid, pyrrolnitrine, quintozene, tecloftalam, tecnazene, triazoxide, trichlamide, zarilamid and 2,3,5,6-tetrachloro-4-(methylsulfonyl)-pyridine, N-(4-Chloro-2-nitrophenyl)-N-ethyl-4-methyl-benzenesulfonamide, 2-amino-4-methyl-N-phenyl-5-thiazolecarboxamide, 2-chloro-N-(2,3-dihydro-1,1,3-trimethyl-1H-inden-4-yl)-3-pyridincarboxamide, 3-[5-(4-chlorophenyl)-2,3-dimethylisoxazolidin-3-yl]pyridine, cis-1-(4-chlorophenyl)-2-(1H-1,2,4-triazole-1-yl)-cycloheptanol, methyl 1-(2,3-dihydro-2,2-dimethyl-1H-inden-1-yl)-1H-imidazole-5-carboxylate, 3,4,5-trichloro-2,6-pyridinedicarbonitrile, Methyl 2-[[[cyclopropyl[(4-methoxyphenyl)imino]methyl]thio]methyl]-.alpha.-(methoxy-methylene)-benzeneacetate, 4-Chloro-alpha-propynyloxy-N-[2-[3-methoxy-4-(2-propynyloxy)phenyl]ethyl]-benzeneacetamide, (2S)—N-[2-[4-[[3-(4-chlorophenyl)-2-propynyl]oxy]-3-methoxyphenyl]ethyl]-3-methyl-2-[(methylsulfonyl)amino]-butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propyl-benzopyranon-4-one, N-{(Z)-[(cyclopropylmethoxy)imino][6-(difluoromethoxy)-2,3-difluorophenyl]methyl}-2-phenyl-acetamide, N-(3-ethyl-3,5,5-trimethyl-cyclohexyl)-3-formylamino-2-hydroxy-benzamide, 2-[[[[1-[3(1Fluoro-2-phenylethyl)oxy]phenyl]ethylidene]amino]oxy]methyl]-alpha-(methoxyimino)-N-methyl-alphaE-benzeneacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-m ethylacetamide Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

1. Acetylcholinesterase (AChE) inhibitors 1.1 carbamates (for example alanycarb, aldicarb, aldoxycarb, allyxycarb, aminocarb, azamethiphos, bendiocarb, benfuracarb, bufencarb, butacarb, butocarboxim, butoxycarboxim, carbaryl, carbofuran, carbosulfan, chloethocarb, coumaphos, cyanofenphos, cyanophos, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, triazamate, trimethacarb, XMC, xylylcarb)

1.2 organophosphates (for example acephate, azamethiphos, azinphos (-methyl, -ethyl), bromophos-ethyl, bromfenvinfos (-methyl), butathiofos, cadusafos, carbophenothion, chloroethoxyfos, chlorfenvinphos, chloromephos, chlorpyrifos (-methyl/-ethyl), coumaphos, cyanofenphos, cyanophos, chlorfenvinphos, demeton-s-methyl, demeton-s-methylsulphon, dialifos, diazinon, dichlofenthion, dichlorovos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl o-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion)

2. Sodium channel modulators/blockers of voltage-dependent sodium channels 2.1 pyrethroids (for example acrinathrin, allethrin (d-cis-trans, d-trans), beta-cyfluthrin, bifenthrin, bioallethrin, bioallethrin-5-cyclopentyl-isomer, bioethanomethrin, biopermetlirin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, DDT, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R-isomer), tralomethrin, transfluthrin, ZXI 8901, pyrethrins (pyrethrum))

2.2 oxadiazines (for example indoxacarb)

3. Acetylcholine receptor agonists/antagonists 3.1 chloronicotinyls/neonicotinoids (for example acetamiprid, clothianidin, dinotefuran, imidacloprid, nitenpyram, nithiazine, thiacloprid, thiamethoxam)

3.2 nicotine, bensultap, cartap

4. Acetylcholine receptor modulators 4.1 spinosyns (for example spinosad)

5. Antagonists of GABA-controlled chloride channels 5.1 cyclodiene organochlorines (for example camphechloro, chlorodane, endosulfan, gamma-HCH, HCH, heptachloro, lindane, methoxychloro 5.2 fiproles (for example acetoprole, ethiprole, fipronil, vaniliprole)

6. chloride channel activators 6.1 mectins (for example abamectin, avermectin, emamectin, emamectin-benzoate, ivermectin, milbemectin, milbemycin)

7. Juvenile hormone mimetics (for example diofenolan, epofenonane, fenoxycarb, hydroprene, kinoprene, methoprene, pyriproxifen, triprene)

8. Ecdyson agonists/disruptors
8.1 diacylhydrazines (for example chromafenozide, halofenozide, methoxyfenozide, tebufenozide)
9. Chitin Biosynthesis Inhibitors
9.1 benzoylureas (for example bistrifluron, chlofluazuron, diflubenzuron, fluazuron, flucycloxuron, flufenoxuron, hexaflumuron, lufenuron, novaluron, noviflumuron, penfluron, teflubenzuron, triflumuron)
9.2 buprofezin
9.3 cyromazine
10. Inhibitors of oxidative phosphorylation, ATP disruptors
10.1 diafenthiuron
10.2 organotins (for example azocyclotin, cyhexatin, fenbutatin-oxide)
11. Decouplers of oxidative phosphorylation acting by interrupting the H-proton gradient
11.1 pyrroles (for example chlorofenapyr)
11.2 dinitrophenols (for example binapacryl, dinobuton, dinocap, DNOC)
12. Site-I electron transport inhibitors
12.1 METIs (for example fenazaquin, fenpyroximate, pyrimidifen, pyridaben, tebufenpyrad, tolfenpyrad)
12.2 hydramethylnone
12.3 dicofol
13. Site-II electron transport inhibitors
13.1 rotenone
14. Site-III electron transport inhibitors
14.1 acequinocyl, fluacrypyrim
15. Microbial disruptors of the insect gut membrane
*Bacillus thuringiensis* strains
16. Inhibitors of fat synthesis
16.1 tetronic acids (for example spirodiclofen, spiromesifen)
16.2 tetramic acids [for example 3-(2,5-dimethylphenyl)-8-methoxy-2-oxo-1-azaspiro-[4.5]dec-3-en-4-yl ethyl carbonate (alias: carbonic acid, 3-(2,5-dimethylphenyl)-8-methoxy-2-oxo-1-azaspiro[4,5]dec-3-en-4-yl ethyl ester, CAS Reg. No.: 382608-10-8) and carbonic acid, cis-3-(2,5-dimethylphenyl)-8-methoxy-2-oxo-1-azaspiro[4,5]dec-3-en-4-yl ethyl ester (CAS Reg. No.: 203313-25-1)]
17. Carboxamides
(for example flonicamid)
18. Octopaminergic agonists
(for example amitraz)
19. Inhibitors of magnesium-stimulated ATPase
(for example propargite)
20. Phthalamides
(for example $N^2$-[1,1-dimethyl-2-(methylsulphonyl)ethyl]-3-iodo-N'-[2-methyl-4-[1,2,2,2-tetra-fluoro-1-(trifluoromethyl)ethyl]phenyl]-1,2-benzenedicarboxamide (CAS Reg. No.: 272451-65-7), flubendiamide)
21. Nereistoxin analogues
(for example thiocyclam hydrogen oxalate, thiosultap-sodium)
22. Biologicals, hormones or pheromones
(for example azadirachtin, *Bacillus* spec., *Beauveria* spec., Codlemone, *Metarrhizium* spec., *Paecilomyces* spec., Thuringiensin, *Verticillium* spec.)
23. Active compounds with unknown or unspecific mechanisms of action
23.1 fumigants (for example aluminium phosphide, methyl bromide, sulphuryl fluoroide)
23.2 selective antifeedants (for example cryolite, flonicamid, pymetrozine)
23.3 mite growth inhibitors (for example clofentezine, etoxazole, hexythiazox)
23.4 amidoflumet, benclothiaz, benzoximate, bifenazate, bromopropylate, buprofezin, chinomethionat, chlorodimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulfluramid, tetradifon, tetrasul, triarathene, verbutin,
furthermore the compound 3-methylphenyl propylcarbamate (Tsumacide Z), the compound 3-(5-chloro-3-pyridinyl)-8-(2,2,2-trifluoroethyl)-8-azabicyclo[3.2.1]octane-3-carbonitrile (CAS Reg. No. 185982-80-3) and the corresponding 3-endo-isomer (CAS Reg. No. 185984-60-5) (cf. WO 96/37494, WO 98/25923), and preparations which comprise insecticidally active plant extracts, nematodes, fungi or viruses.

A mixture with other known active compounds, such as herbicides, or with fertilizers and growth regulators, safeners and/or semiochemicals is also possible.

The active compounds can be used as such or in the form of their formulations or the use forms prepared therefrom by further dilution, such as ready-to-use solutions, emulsions, suspensions, powders, tablets, pastes, microcapsules and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compounds concentration in the use forms can be varied within a substantial range. They are, in general, from 1 to 0.0001% by weight, preferably from 0.5 and 0.001%.

For the treatment of seed, amounts of active compound of 0.1 to 10 g, especially 1 to 5 g, are generally employed per 1 kilogram of seed.

For the treatment of soil, active compound concentrations, at the point of action, of 0.00001 to 0.1% by weight, especially of 0.0001 to 0.02%, are generally employed.

As already mentioned above, all plants and parts of plants can be treated according to the invention.

In a preferred embodiment naturally occurring plant species and plant varieties or those obtained by conventional biological breeding methods, such as crossbreeding or protoplast fusion as well as parts of such plants are treated. In an additional preferred embodiment transgenic plants and plant varieties which have been obtained by genetic engineering methods, possibly in combination with conventional methods (genetically modified organisms) and parts of such plants are treated. The term "parts" or "parts of plants" or "plant parts" is explained above.

According to the invention plants of the plant varieties commercially available or used at any particular time are very preferably treated. Plant varieties are understood to be plants with specific properties ("traits") which have been obtained both by conventional breeding, by mutagenesis or by recombinant DNA techniques. They can be varieties, biotypes or genotypes.

Depending on the species or varieties of plants, their location and growth conditions (the types of soil, climate, vegetation period and feed concerned), superadditive ("synergistic") effects can occur as a result of the treatment according to the invention. Effects such as for example reduced application rates and/or broadening of the activity spectra and/or increased activity of the compounds and compositions usable according to the invention, improved plant growth, increased tolerance of high or low temperatures, increased tolerance of dry conditions or water or ground salt contents, increased flowering capacity, facilitated harvesting, acceleration of maturity, increased crop yields, higher quality and/or increased nutritional value of the harvested crops and increased storing quality and/or processability of the harvested crops are possible, which are greater than those actually expected.

Preferred transgenic plants or plant varieties (obtained by genetic engineering) to be treated according to the invention include all plants which as a result of the genetic modification concerned have received genetic material which provides them with particularly advantageous valuable properties ("traits"). Examples of such properties are improved plant growth, increased tolerance of high or low temperatures, increased tolerance of dry conditions or water or ground salt contents, increased flowering capacity, facilitated harvesting, acceleration of maturity, increased crop yields, higher quality and/or increased nutritional value of the harvested crops and increased storing quality and/or processability of the harvested crops. Additional and particularly noteworthy examples of such properties are increased resistance of the plants to animal and microbial pests, such as to insects, mites, phytopathogenic fungi, bacteria and/or viruses as well as increased tolerance by the plants of certain herbicidal active compounds. Examples which may be mentioned of transgenic plants are the important crop plants such as cereals (wheat and rice), corn, soybeans, potatoes, cotton, rape and fruit plants (producing apples, pears, citrus fruits and grapes), the crop plants corn, soybeans, potatoes, cotton and rape being particularly noteworthy. Particularly significant properties ("traits") are increased resistance of the plants to insects due to the toxins forming in the plants, and in particular those which are produced in the plants (hereinafter referred to as "Bt plants") by the genetic material obtained from *Bacillus Thuringiensis* (e.g. by the genes Cry1A(a), Cry1A(b), Cry1A (c), Cry11A, CryIIIB2, Cry9c Cry2Ab, Cry3Bb and CryIF and combinations thereof). Particularly significant properties ("traits") are the increased resistance of plants to fungi, bacteria and viruses due to systemically acquired resistance (SAR), systemin, phytoalexins, elicitors and resistance genes and correspondingly expressed proteins and toxins. Particularly significant properties ("traits") are also increased tolerance by the plants of certain herbicidal active compounds, such as for example imidazolinones, sulphonylureas, glyphosate or phosphinotricine (e.g. the "PAT" gene). The corresponding genes imparting the required properties ("traits") can also occur in the transgenic plants in combination with each other. Examples which may be mentioned of "Bt plants" are varieties of corn, cotton, soybeans and potatoes which are sold under the trade names YIELD GARD® (e.g. corn, cotton, soybeans), KnockOut® (e.g. corn), StarLink® (e.g. corn), Bollgard® (cotton), Nucotn® (cotton) and NewLeaf® (potatoes). Examples which may be mentioned of herbicide-tolerant plants are varieties of corn, cotton and soybeans which are sold under the trade names Roundup Ready® (tolerance of glyphosate, e.g. corn, cotton, soybeans), Liberty Link® (tolerance of phosphinotricine, e.g. rape), IMI® (tolerance of imidazolinones) and STS® (tolerance of sulphonylureas, e.g. corn). Herbicide-resistant plants (bred for herbicide tolerance in the conventional manner) which may be mentioned are also the varieties (e.g. corn) sold under the name Clearfield®. The above statements do of course also apply to any plant varieties which may be developed in the future or launched onto the market in the future and which have the genetic properties ("traits") described above or developed in the future.

According to the invention the above-mentioned plants can be particularly advantageously treated with the compounds of the general formula I or the active compound mixtures according to the invention. The preferred ranges mentioned above for the active compounds or mixtures also apply to the treatment of these plants. Particularly advantageous is the treatment of plants with the compounds or mixtures specifically listed in the present text.

Then the preparation and use of the compounds of the present invention will be described more specifically by the following Examples. The present invention, however, should not be restricted to them in any way.

SYNTHESIS EXAMPLE 1

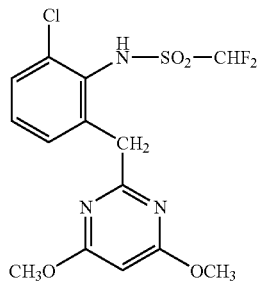

2-Chloro-6-[(4,6-dimethoxypyrimidin-2-yl)methyl] aniline 1.54 g (5.51 mmol) was dissolved in dichloromethane (12 ml), to which then pyridine 0.87 g (11.01 mmol) was added. The solution was cooled to −5° C. and a solution of difluoromethanesulfonyl chloride 1.66 g (11.01 mmol) in dichloromethane (2 ml) was added thereto. The reaction solution was stirred at room temperature for 4 days, then water was added thereto and extracted three times with dichloromethane. After the organic layer had been washed with water and dried, dichloromethane was distilled off under reduced pressure. The obtained oily substance was treated with column chromatography using a 1:6 mixed solvent of ethyl acetate and hexane as eluent to obtain the objective 2-chloro-6-[(4,6-dimethoxypyrimidin-2-yl)methyl]-N-difluoromethanesulfonanilide 1.2 g (yield 55%) as white crystals.

$^1$H-NMR (300 MHz, CDCl$_3$) δ3.94 (6H, s), 4.30 (2H, s), 5.92 (1H, s), 6.74 (1H, t), 7.18-7.21 (1H, m), 7.33-7.38 (2H, m), 1.09 (1H, br).

SYNTHESIS EXAMPLE 2

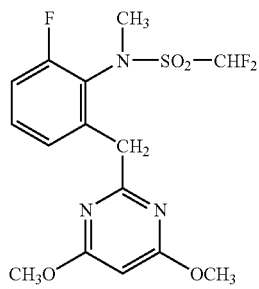

To a solution of 2-fluoro-6-[(4,6-dimethoxypyrimidin-2-yl)methyl]-N-difluoromethanesulfonanilide 0.1 g (0.27 mmol) in acetonitrile (3 ml), potassium carbonate 0.06 g (0.40 mmol) and methyl iodide 0.08 g were added and the mixture was stirred at room temperature for 24 hours. The obtained reaction solution was filtered and the crude crystals, obtained through distillation of the filtrate under reduced pressure, were washed with a 1:6 mixed solvent of ether and hexane to obtain the objective 2-fluoro-6-[(4,6-dimethoxypyrimidin-2-yl)methyl]-N-methyl-N-difluoromethanesulfonanilide 0.1 g (yield 93%) as white crystals.

$^1$H-NMR (300 MHz, CDCl$_3$) δ3.97 (6H, s), 4.26 (2H, s), 5.94 (1H, s), 6.59 (1H, t), 7.05-7.13 (1H, m), 7.16-7.23 (2H, m), 11.14 (1H, br).

SYNTHESIS EXAMPLE 3

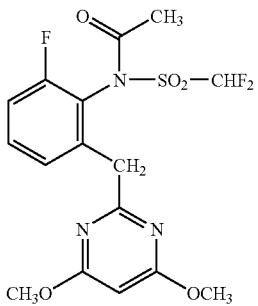

A solution of 2-fluoro-6-[(4,6-dimethoxypyrimidin-2-yl)methyl]-N-difluoromethanesulfonanilide 0.1 g (0.27 mmol) and triethylamine 0.04 g (0.40 mmol) in dichloromethane (3 ml) was cooled with ice. To the solution, acetyl chloride 0.03 g (0.32 mmol) was added and the mixed solution was stirred at room temperature for 24 hours. Water was added to the obtained reaction solution and the organic layer was separated. The aqueous layer was further extracted three times with dichloromethane. After the organic layer had been washed with water and dried, dichloromethane was distilled off under reduced pressure, and the obtained crude crystals were washed with a 1:6 mixed solvent of ether and hexane to obtain the objective 2-fluoro-6-[(4,6-dimethoxypyrimidin-2-yl)methyl]-N-acetyl-N-difluoromethanesulfonanilide 0.1 g (yield 89%) as white crystals.

$^1$H-NMR (300 MHz, CDCl$_3$) δ1.94 (3H, s), 3.87 (6H, s), 4.10 (1H, d, J=15 Hz), 4.30 (1H, d, J=15 Hz), 5.89 (1H, s), 6.97 (1H, t), 7.14-7.17 (1H, m), 7.33-7.45 (2H, m).

SYNTHESIS EXAMPLE 4

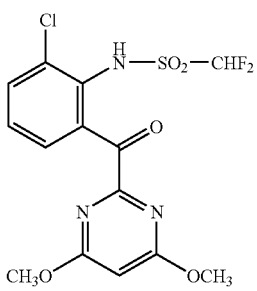

2-Chloro-6-[(4,6-dimethoxypyrimidin-2-yl)methyl]-N-difluoromethanesulfonanilide 0.4 g (1.02 mmol) was dissolved in acetic acid (6 ml), to which then chromium (VI) oxide 0.31 g (3.05 mmol) was added, and the solution was heated to 30° C. The solution was stirred for 6 hours and further stirred at room temperature for 12 hours. The reaction solution was diluted with water and extracted three times with diethyl ether. The organic layer washed with water and dried, and diethyl ether was distilled off under reduced pressure. The obtained oily substance was treated with column chromatography using a 1:3 mixed solvent of ethyl acetate and hexane as eluent to obtain the objective 2-chloro-6-[(4,6-dimethoxypyrimidin-2-yl)carbonyl]-N-difluoromethanesulfonanilide 0.28 g (yield 67%) as white crystals.

$^1$H-NMR (300 MHz, CDCl$_3$) δ 3.93 (6H, s), 6.19 (1H, s), 6.34 (1H, t), 7.37-7.43 (1H, m), 7.63-7.69 (2H, m).

SYNTHESIS EXAMPLE 5

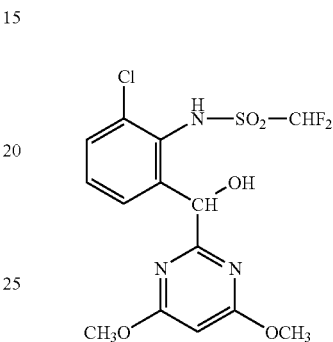

2-Chloro-6-[(4,6-dimethoxypyrimidin-2-yl)carbonyl]-N-difluoromethanesulfonanilide 0.14 g (0.34 mmol) was dissolved in methanol 5 ml and the solution was cooled to 5° C., and sodium borohydride 0.026 g (0.69 m mol) was added thereto while stirring. The reaction solution was stirred at room temperature for 2 hours and then distilled under reduced pressure. The obtained crystals were dissolved in water and dichloromethane and neutralized with citric acid. The organic layer was separated and the aqueous layer was further extracted three times with dichloromethane. After the organic layer had been washed with water and dried, dichloromethane was distilled off under reduced pressure to obtain the objective 2-chloro-6-[(4,6-dimethoxypyrimidin-2-yl)hydroxymethyl]-N-difluoromethanesulfonanilide 0.11 g (yield 78%) as white crystals.

$^1$H NMR-(300 MHz, CDCl$_3$) δ3.99 (6H, s), 4.99 (1H, br), 5.99 (1H, s), 6.24 (1H, s), 6.76 (1H, t), 7.27-7.30 (1H, m), 7.39-7.42 (1H, m), 7.64-7.67 (1H, m), 10.62 (1H, br).

Examples of the compounds obtained in the same manner to the above-mentioned Synthesis Examples 1 to 5 and obtained easily according to the general preparation processes of the aforementioned preparation processes (a) to (h) are shown, together with the compounds of the above-mentioned Synthesis Examples 1 to 5, in the following Tables 1 to 7, and their physical and chemical properties are shown in Table 8.

In the tables Me represents methyl, Et represents ethyl, iPr represents isopropyl, CH$_2$Ph represents benzyl, cycloPr represents cyclopropyl, cyclohexyl represents cyclohexyl, OMe represents methoxy, OEt represents ethoxy, OPh represents phenoxy, SMe represents methylthio, SOMe represents methylsulfinyl, SO$_2$Me represents methylsulfonyl, COMe represents acetyl, COcPr represents cyclopropylcarbonyl, CO$_2$Me or COOMe represents methoxycarbonyl, vinyl represents vinyl, allyl represents allyl, propargyl represents propargyl, MOM represents methoxymethyl, and CH$_2$OEt represents ethoxymethyl.

TABLE 1

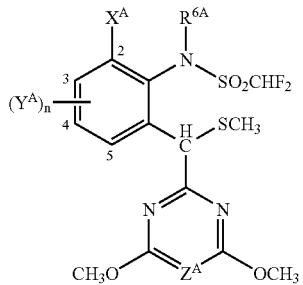

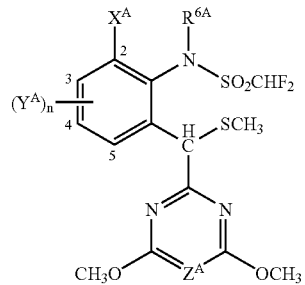

| Compound No. | $X^A$ | $(Y^A)_n$ | $R^{6A}$ | $Z^A$ |
|---|---|---|---|---|
| 1-1 | H | H | H | CH |
| 1-2 | H | H | CH₃ | CH |
| 1-3 | H | H | CH₂OCH₃ | CH |
| 1-4 | H | H | CH₂OCH₂CH₃ | CH |
| 1-5 | H | H | COCH₃ | CH |
| 1-6 | H | H | CO₂CH₃ | CH |
| 1-7 | H | H | CO₂CH₂CH₃ | CH |
| 1-8 | H | H | SO₂CH₃ | CH |
| 1-9 | H | H | SO₂CHF₂ | CH |
| 1-10 | H | H | SO₂CF₃ | CH |
| 1-11 | H | H | SO₂CH₂Cl | CH |
| 1-12 | H | H | SO₂CH₂CF₃ | CH |
| 1-13 | H | H | SO₂CH₂CN | CH |
| 1-14 | F | H | H | CH |
| 1-15 | F | H | CH₃ | CH |
| 1-16 | F | H | CH₂OCH₃ | CH |
| 1-17 | F | H | CH₂OCH₂CH₃ | CH |
| 1-18 | F | H | COCH₃ | CH |
| 1-19 | F | H | CO₂CH₃ | CH |
| 1-20 | F | H | CO₂CH₂CH₃ | CH |
| 1-21 | F | H | SO₂CH₃ | CH |
| 1-22 | F | H | SO₂CHF₂ | CH |
| 1-23 | F | H | SO₂CF₃ | CH |
| 1-24 | F | H | SO₂CH₂Cl | CH |
| 1-25 | F | H | SO₂CH₂CF₃ | CH |
| 1-26 | F | H | SO₂CH₂CN | CH |
| 1-27 | Cl | H | H | CH |
| 1-28 | Cl | H | CH₃ | CH |
| 1-29 | Cl | H | CH₂OCH₃ | CH |
| 1-30 | Cl | H | CH₂OCH₂CH₃ | CH |
| 1-31 | Cl | H | COCH₃ | CH |
| 1-32 | Cl | H | CO₂CH₃ | CH |
| 1-33 | Cl | H | CO₂CH₂CH₃ | CH |
| 1-34 | Cl | H | SO₂CH₃ | CH |
| 1-35 | Cl | H | SO₂CHF₂ | CH |
| 1-36 | Cl | H | SO₂CH₃ | CH |
| 1-37 | Cl | H | SO₂CH₂Cl | CH |
| 1-38 | Cl | H | SO₂CH₂CF₃ | CH |
| 1-39 | Cl | H | SO₂CH₂CN | CH |
| 1-40 | H | H | H | N |
| 1-41 | H | H | CH₃ | N |
| 1-42 | H | H | CH₂OCH₂CH₃ | N |
| 1-43 | H | H | COCH₃ | N |
| 1-44 | H | H | CO₂CH₃ | N |
| 1-45 | H | H | CO₂CH₂CH₃ | N |
| 1-46 | F | H | H | N |
| 1-47 | F | H | CH₃ | N |
| 1-48 | F | H | CH₂OCH₂CH₃ | N |
| 1-49 | F | H | COCH₃ | N |
| 1-50 | F | H | CO₂CH₃ | N |
| 1-51 | F | H | CO₂CH₂CH₃ | N |
| 1-52 | Cl | H | H | N |
| 1-53 | Cl | H | CH₃ | N |
| 1-54 | Cl | H | CH₂OCH₂CH₃ | N |
| 1-55 | Cl | H | COCH₃ | N |
| 1-56 | Cl | H | CO₂CH₃ | N |
| 1-57 | Cl | H | CO₂CH₂CH₃ | N |
| 1-58 | H | H | H | C—CH₃ |
| 1-59 | F | H | H | C—CH₃ |
| 1-60 | Cl | H | H | C—CH₃ |
| 1-61 | H | 3-F | H | CH |
| 1-62 | H | 4-F | H | CH |
| 1-63 | H | 5-F | H | CH |
| 1-64 | H | 3-Cl | H | CH |
| 1-65 | H | 4-Cl | H | CH |
| 1-66 | H | 5-Cl | H | GH |
| 1-67 | H | 3,5-F₂ | H | CH |
| 1-68 | H | 3,5-Cl₂ | H | CH |
| 1-69 | H | 4,5-F₂ | H | CH |
| 1-70 | H | 4,5-Cl₂ | H | CH |
| 1-71 | H | 3-CH₃ | H | CH |
| 1-72 | H | 4-CH₃ | H | CH |
| 1-73 | H | 5-CH₃ | H | CH |
| 1-74 | H | 3-CH₃ | H | CH |
| 1-75 | H | 4-CH₃ | H | CH |
| 1-76 | H | 5-CH₃ | H | CH |
| 1-77 | H | 3-CH₂OCH₃ | H | CH |
| 1-78 | H | 4-CH₂OCH₃ | H | CH |
| 1-79 | H | 5-CH₂OCH₃ | H | CH |
| 1-80 | H | 3-OCH₃ | H | CH |
| 1-81 | H | 4-OCH₃ | H | CH |
| 1-82 | H | 5-OCH₃ | H | CH |
| 1-83 | H | 3-CO₂CH₃ | H | CH |
| 1-84 | H | 4-CO₂CH₃ | H | CH |
| 1-85 | H | 5-CO₂CH₃ | H | CH |
| 1-86 | H | 3-SO₂CH₃ | H | CH |
| 1-87 | H | 4-SO₂CH₃ | H | CH |
| 1-88 | H | 5-SO₂CH₃ | H | CH |
| 1-89 | H | 3-SCF₃ | H | CH |
| 1-90 | H | 4-SCF₃ | H | CH |
| 1-91 | H | 5-SCF₃ | H | CH |
| 1-92 | H | 3-SOCH₃ | H | CH |
| 1-93 | H | 4-SOCH₃ | H | CH |
| 1-94 | H | 5-SOCH₃ | H | CH |
| 1-95 | H | 3-SO₂CF₃ | H | CH |
| 1-96 | H | 4-SO₂CH₃ | H | CH |
| 1-97 | H | 5-SO₂CH₃ | H | CH |
| 1-98 | H | 3-N(CH₃)₂ | H | CH |
| 1-99 | H | 4-N(CH₃)₂ | H | CH |
| 1-100 | H | 5-N(CH₃)₂ | H | CH |
| 1-101 | H | 3-NO₂ | H | CH |
| 1-102 | H | 4-NO₂ | H | CH |
| 1-103 | H | 5-NO₂ | H | CH |
| 1-104 | H | 3-CN | H | CH |
| 1-105 | H | 4-CN | H | CH |
| 1-106 | H | 5-CN | H | CH |
| 1-107 | H | 3-COCH₃ | H | CH |
| 1-108 | H | 4-COCH₃ | H | CH |
| 1-109 | H | 5-COCH₃ | H | CH |
| 1-110 | F | 3-F | H | CH |
| 1-111 | F | 4-F | H | CH |
| 1-112 | F | 5-F | H | CH |
| 1-113 | F | 3-Cl | H | CH |
| 1-114 | F | 4-Cl | H | CH |
| 1-115 | F | 5-Cl | H | CH |
| 1-116 | F | 3-CH₃ | H | CH |
| 1-117 | F | 4-CH₃ | H | CH |
| 1-118 | F | 5-CH₃ | H | CH |
| 1-119 | F | 3-OCH₃ | H | CH |
| 1-120 | F | 4-OCH₃ | H | CH |

TABLE 1-continued

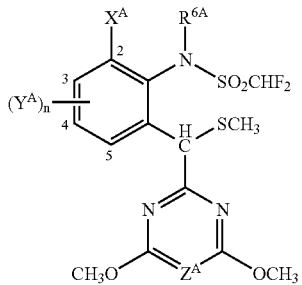

| Compound No. | $X^A$ | $(Y^A)_n$ | $R^{6A}$ | $Z^A$ |
|---|---|---|---|---|
| 1-121 | F | 5-OCH₃ | H | CH |
| 1-122 | F | 4-CN | H | CH |
| 1-123 | F | 3,4-F₂ | H | CH |
| 1-124 | F | 4,5-F₂ | H | CH |
| 1-125 | F | 4-F-3-Cl | H | CH |
| 1-126 | F | 3-F-5-Cl | H | CH |
| 1-127 | F | 5-F-4-CN | H | CH |
| 1-128 | F | 3-F-4-CH₃ | H | CH |
| 1-129 | F | 3-CF₃ | H | CH |
| 1-130 | F | 5-CF₃ | H | CH |
| 1-131 | F | 4-Br | H | CH |
| 1-132 | F | 5-OCH₃-4-F | H | CH |
| 1-133 | Cl | 3-F | H | CH |
| 1-134 | Cl | 4-F | H | CH |
| 1-135 | Cl | 5-F | H | CH |
| 1-136 | Cl | 3-Cl | H | CH |
| 1-137 | Cl | 4-Cl | H | CH |
| 1-138 | Cl | 5-Cl | H | CH |
| 1-139 | Cl | 3-CH₃ | H | CH |
| 1-140 | Cl | 4-CH₃ | H | CH |
| 1-141 | Cl | 5-CH₃ | H | CH |
| 1-142 | Cl | 3-OCH₃ | H | CH |
| 1-143 | Cl | 4-OCH₃ | H | CH |
| 1-144 | Cl | 5-OCH₃ | H | CH |
| 1-145 | Cl | 4-SO₂CH₃ | H | CH |
| 1-146 | Cl | 3-SCH₃ | H | CH |
| 1-147 | Cl | 4-SCH₃ | H | CH |
| 1-148 | Cl | 5-SCF₃ | H | CH |
| 1-149 | Cl | 3-SOCH₃ | H | CH |
| 1-150 | Cl | 4-SOCH₃ | H | CH |
| 1-151 | Cl | 5-SOCH₃ | H | CH |
| 1-152 | Cl | 3-SO₂CH₃ | H | CH |
| 1-153 | Cl | 4-SO₂CH₃ | H | CH |
| 1-154 | Cl | 5-SO₂CH₃ | H | CH |
| 1-155 | Cl | 4-CN | H | CH |
| 1-156 | Cl | 3,4-Cl₂ | H | CH |
| 1-157 | Cl | 4,5-Cl₂ | H | CH |
| 1-158 | Cl | 3-Cl-4-CH₃ | H | CH |
| 1-159 | Cl | 4-Cl-3-CH₃ | H | CH |
| 1-160 | Cl | 5-OCH₃-4-F | H | CH |
| 1-161 | Cl | 4-SO₂CH₃ | H | CH |
| 1-162 | Cl | 4-CF₃ | H | CH |
| 1-163 | Cl | 5-CF₃ | H | CH |
| 1-164 | CHO | H | H | CH |
| 1-165 | COCH₃ | H | H | CH |
| 1-166 | COcPr | H | H | CH |
| 1-167 | CO₂CH₃ | H | H | CH |
| 1-168 | CO₂CH₂CH₃ | H | H | CH |
| 1-169 | CON(CH₃)₂ | H | H | CH |
| 1-170 | N(CH₃)₂ | H | H | CH |
| 1-171 | OCH₃ | H | H | CH |
| 1-172 | OCF₃ | H | H | CH |
| 1-173 | OCHF₂ | H | H | CH |
| 1-174 | OPh | H | H | CH |
| 1-175 | SO₂CH₃ | H | H | CH |
| 1-176 | SCF₃ | H | H | CH |
| 1-177 | SOCF₃ | H | H | CH |
| 1-178 | SO₂CF₃ | H | H | CH |
| 1-179 | CN | H | H | CH |
| 1-180 | NO₂ | H | H | CH |

TABLE 1-continued

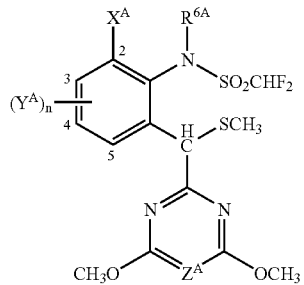

| Compound No. | $X^A$ | $(Y^A)_n$ | $R^{6A}$ | $Z^A$ |
|---|---|---|---|---|
| 1-181 | OSO₂CH₃ | H | H | CH |
| 1-182 | OSO₂CF₃ | H | H | CH |
| 1-183 | OSO₂CHF₂ | H | H | CH |
| 1-184 | OSO₂CH₂Cl | H | H | CH |
| 1-185 | OSO₂CH₂CF₃ | H | H | CH |
| 1-186 | OSO₂CH₂CN | H | H | CH |
| 1-187 | COCH₃ | H | H | N |
| 1-188 | COoPr | H | H | N |
| 1-189 | CO₂CH₃ | H | H | N |
| 1-190 | CO₂CH₂CH₃ | H | H | N |

TABLE 2

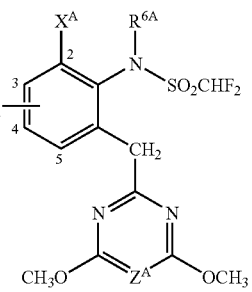

| Compound No. | $X^A$ | $(Y^A)_n$ | $R^{6A}$ | $Z^A$ |
|---|---|---|---|---|
| 2-1 | H | H | H | CH |
| 2-2 | H | H | CH₃ | CH |
| 2-3 | H | H | CH₂OCH₃ | CH |
| 2-4 | H | H | CH₂OCH₂CH₃ | CH |
| 2-5 | H | H | COCH₃ | CH |
| 2-6 | H | H | CO₂CH₃ | CH |
| 2-7 | H | H | CO₂CH₂CH₃ | CH |
| 2-8 | H | H | SO₂CH₃ | CH |
| 2-9 | H | H | SO₂CHF₂ | CH |
| 2-10 | H | H | SO₂CH₃ | CH |
| 2-11 | H | H | SO₂CH₂Cl | CH |
| 2-12 | H | H | SO₂CH₂CH₃ | CH |
| 2-13 | H | H | SO₂CH₂CN | CH |
| 2-14 | F | H | CH₃ | CH |
| 2-15 | F | H | CH₂CH₃ | CH |
| 2-16 | F | H | CH₂OCH₃ | CH |
| 2-17 | F | H | CH₂OCH₂CH₃ | CH |
| 2-18 | F | H | COCH₃ | CH |
| 2-19 | F | H | CO₂CH₃ | CH |
| 2-20 | F | H | CO₂CH₂CH₃ | CH |
| 2-21 | F | H | SO₂CH₃ | CH |
| 2-22 | F | H | SO₂CHF₂ | CH |
| 2-23 | F | H | SO₂CH₃ | CH |
| 2-24 | F | H | SO₂CH₂Cl | CH |
| 2-25 | F | H | SO₂CH₂CH₃ | CH |
| 2-26 | F | H | SO₂CH₂CN | CH |

TABLE 2-continued

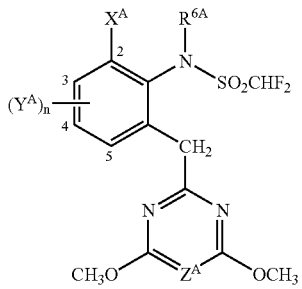

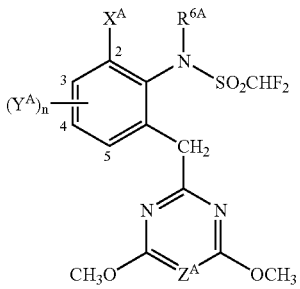

| Compound No. | $X^A$ | $(Y^A)_n$ | $R^{6A}$ | $Z^A$ |
|---|---|---|---|---|
| 2-27 | Cl | H | CH₃ | CH |
| 2-28 | Cl | H | CH₂CH₃ | CH |
| 2-29 | Cl | H | CH₂OCH₃ | CH |
| 2-30 | Cl | H | CH₂OCH₂CH₃ | CH |
| 2-31 | Cl | H | COCH₃ | CH |
| 2-32 | Cl | H | CO₂CH₃ | CH |
| 2-33 | Cl | H | CO₂CH₂CH₃ | CH |
| 2-34 | Cl | H | SO₂CH₃ | CH |
| 2-35 | Cl | H | SO₂CHF₂ | CH |
| 2-36 | Cl | H | SO₂CF₃ | CH |
| 2-37 | Cl | H | SO₂CH₂Cl | CH |
| 2-38 | Cl | H | SO₂CH₂CF₃ | CH |
| 2-39 | Cl | H | SO₂CH₂CN | CH |
| 2-40 | H | H | H | N |
| 2-41 | H | H | CH₃ | N |
| 2-42 | H | H | CH₂OCH₂CH₃ | N |
| 2-43 | H | H | COCH₃ | N |
| 2-44 | H | H | CO₂CH₃ | N |
| 2-45 | H | H | CO₂CH₂CH₃ | N |
| 2-46 | F | H | CH₃ | N |
| 2-47 | F | H | CH₂CF₃ | N |
| 2-48 | F | H | CH₂OCH₂CH₃ | N |
| 2-49 | F | H | COCH₃ | N |
| 2-50 | F | H | CO₂CH₃ | N |
| 2-51 | F | H | CO₂CH₂CH₃ | N |
| 2-52 | Cl | H | CH₃ | N |
| 2-53 | Cl | H | CH₂CF₃ | N |
| 2-54 | Cl | H | CH₂OCH₂CH₃ | N |
| 2-55 | Cl | H | COCH₃ | N |
| 2-56 | Cl | H | CO₂CH₃ | N |
| 2-57 | Cl | H | CO₂CH₂CH₃ | N |
| 2-58 | H | H | H | C—CH₃ |
| 2-59 | F | H | H | C—CH₃ |
| 2-60 | Cl | H | H | C—CH₃ |
| 2-61 | H | 3-F | H | CH |
| 2-62 | H | 4-F | H | CH |
| 2-63 | H | 5-F | H | CH |
| 2-64 | H | 3-Cl | H | CH |
| 2-65 | H | 4-Cl | H | CH |
| 2-66 | H | 5-Cl | H | CH |
| 2-67 | H | 3,5-F₂ | H | CH |
| 2-68 | H | 3,5-Cl₂ | H | CH |
| 2-69 | H | 4,5-F₂ | H | CH |
| 2-70 | H | 4,5-Cl₂ | H | CH |
| 2-71 | H | 3-CH₃ | H | CH |
| 2-72 | H | 4-CH₃ | H | CH |
| 2-73 | H | 5-CH₃ | H | CH |
| 2-74 | H | 3-CF₃ | H | CH |
| 2-75 | H | 4-CF₃ | H | CH |
| 2-76 | H | 5-CF₃ | H | CH |
| 2-77 | H | 3-CH₂OCH₃ | H | CH |
| 2-78 | H | 4-CH₂OCH₃ | H | CH |
| 2-79 | H | 5-CH₂OCH₃ | H | CH |
| 2-80 | H | 3-OCH₃ | H | CH |
| 2-81 | H | 4-OCH₃ | H | CH |
| 2-82 | H | 5-OCH₃ | H | CH |
| 2-83 | H | 3-CO₂CH₃ | H | CH |
| 2-84 | H | 4-CO₂CH₃ | H | CH |
| 2-85 | H | 5-CO₂CH₃ | H | CH |
| 2-86 | H | 3-SO₂CH₃ | H | CH |
| 2-87 | H | 4-SO₂CH₃ | H | CH |
| 2-88 | H | 5-SO₂CH₃ | H | CH |
| 2-89 | H | 3-SCF₃ | H | CH |
| 2-90 | H | 4-SCF₃ | H | CH |
| 2-91 | H | 5-SCF₃ | H | CH |
| 2-92 | H | 3-SOCF₃ | H | CH |
| 2-93 | H | 4-SOCF₃ | H | CH |
| 2-94 | H | 5-SOCF₃ | H | CH |
| 2-95 | H | 3-SO₂CF₃ | H | CH |
| 2-96 | H | 4-SO₂CF₃ | H | CH |
| 2-97 | H | 5-SO₂CF₃ | H | CH |
| 2-98 | H | 3-N(CH₃)₂ | H | CH |
| 2-99 | H | 4-N(CH₃)₂ | H | CH |
| 2-100 | H | 5-N(CH₃)₂ | H | CH |
| 2-101 | H | 3-NO₂ | H | CH |
| 2-102 | H | 4-NO₂ | H | CH |
| 2-103 | H | 5-NO₂ | H | CH |
| 2-104 | H | 3-CN | H | CH |
| 2-105 | H | 4-CN | H | CH |
| 2-106 | H | 5-CN | H | CH |
| 2-107 | H | 3-COCH₃ | H | CH |
| 2-108 | H | 4-COCH₃ | H | CH |
| 2-109 | H | 5-COCH₃ | H | CH |
| 2-110 | F | 3-F | H | CH |
| 2-111 | F | 4-F | H | CH |
| 2-112 | F | 5-F | H | CH |
| 2-113 | F | 3-Cl | H | CH |
| 2-114 | F | 4-Cl | H | CH |
| 2-115 | F | 5-Cl | H | CH |
| 2-116 | F | 3-CH₃ | H | CH |
| 2-117 | F | 4-CH₃ | H | CH |
| 2-118 | F | 5-CH₃ | H | CH |
| 2-119 | F | 3-OCH₃ | H | CH |
| 2-120 | F | 4-OCH₃ | H | CH |
| 2-121 | F | 5-OCH₃ | H | CH |
| 2-122 | F | 4-CN | H | CH |
| 2-123 | F | 3,4-F₂ | H | CH |
| 2-124 | F | 4,5-F₂ | H | CH |
| 2-125 | F | 4-F-3-Cl | H | CH |
| 2-126 | F | 3-F-5-Cl | H | CH |
| 2-127 | F | 5-F-4-CN | H | CH |
| 2-128 | F | 3-F-4-CF₃ | H | CH |
| 2-129 | F | 3-CF₃ | H | CH |
| 2-130 | F | 5-CF₃ | H | CH |
| 2-131 | F | 4-Br | H | CH |
| 2-132 | F | 5-OCF₃-4-F | H | CH |
| 2-133 | Cl | 3-F | H | CH |
| 2-134 | Cl | 4-F | H | CH |
| 2-135 | Cl | 5-F | H | CH |
| 2-136 | Cl | 3-Cl | H | CH |
| 2-137 | Cl | 4-Cl | H | CH |
| 2-138 | Cl | 5-Cl | H | CH |
| 2-139 | Cl | 3-CH₃ | H | CH |
| 2-140 | Cl | 4-CH₃ | H | CH |
| 2-141 | Cl | 5-CH₃ | H | CH |
| 2-142 | Cl | 3-OCH₃ | H | CH |
| 2-143 | Cl | 4-OCH₃ | H | CH |
| 2-144 | Cl | 5-OCH₃ | H | CH |
| 2-145 | Cl | 4-SO₂CH₃ | H | CH |
| 2-146 | Cl | 3-SCH₃ | H | CH |

TABLE 2-continued

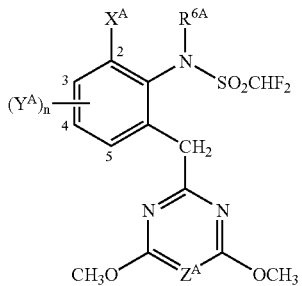

| Compound No. | $X^A$ | $(Y^A)_n$ | $R^{6A}$ | $Z^A$ |
|---|---|---|---|---|
| 2-147 | Cl | 4-SCF$_3$ | H | CH |
| 2-148 | Cl | 5-SCH$_3$ | H | CH |
| 2-149 | Cl | 3-SOCH$_3$ | H | CH |
| 2-150 | Cl | 4-SOCH$_3$ | H | CH |
| 2-151 | Cl | 5-SOCH$_3$ | H | CH |
| 2-152 | Cl | 3-SO$_2$CH$_3$ | H | CH |
| 2-153 | Cl | 4-SO$_2$CH$_3$ | H | CH |
| 2-154 | Cl | 5-SO$_2$CF$_3$ | H | CH |
| 2-155 | Cl | 4-CN | H | CH |
| 2-156 | Cl | 3,4-Cl$_2$ | H | CH |
| 2-157 | Cl | 4,5-Cl$_2$ | H | CH |
| 2-158 | Cl | 3-Cl-4-CF$_3$ | H | CH |
| 2-159 | Cl | 4-Cl-3-CH$_3$ | H | CH |
| 2-160 | Cl | 5-OCF$_3$-4-F | H | CH |
| 2-161 | Cl | 4-SO$_2$CH$_3$ | H | CH |
| 2-162 | Cl | 4-CF$_3$ | H | CH |
| 2-163 | Cl | 5-CF$_3$ | H | CH |
| 2-164 | CHO | H | H | CH |
| 2-165 | COCH$_3$ | H | H | CH |
| 2-166 | COcPr | H | H | CH |
| 2-167 | CO2H | H | H | CH |
| 2-168 | CO$_2$CH$_3$ | H | H | CH |
| 2-169 | CO$_2$CH$_2$CH$_3$ | H | H | CH |
| 2-170 | CON(CH$_3$)$_2$ | H | H | CH |
| 2-171 | N(CH$_3$)$_2$ | H | H | CH |
| 2-172 | OCH$_3$ | H | H | CH |
| 2-173 | OCH$_3$ | H | H | CH |
| 2-174 | OCHF$_2$ | H | H | CH |
| 2-175 | OPh | H | H | CH |
| 2-176 | SO$_2$CH$_3$ | H | H | CH |
| 2-177 | SCF$_3$ | H | H | CH |
| 2-178 | SOCF$_3$ | H | H | CH |
| 2-179 | OSO$_2$CH$_3$ | H | H | CH |
| 2-180 | OSO$_2$CF$_3$ | H | H | CH |
| 2-181 | OSO$_2$CHF$_2$ | H | H | CH |
| 2-182 | OSO$_2$CH$_2$Cl | H | H | CH |
| 2-183 | OSO$_2$CH$_2$CF$_3$ | H | H | CH |
| 2-184 | OSO$_2$CH$_2$CN | H | H | CH |
| 2-185 | COCH$_3$ | H | H | N |
| 2-186 | COcPr | H | H | N |
| 2-187 | CO$_2$CH$_3$ | H | H | N |
| 2-188 | CO$_2$CH$_2$CH$_3$ | H | H | N |
| 2-189 | H | 4-CO$_2$H | H | CH |
| 2-190 | H | 3-F-4-CH$_3$ | H | CH |
| 2-191 | Cl | H | CO$_c$Pr | CH |
| 2-192 | CH$_3$ | 4-CH$_3$ | H | CH |
| 2-193 | CH$_3$ | 3-F | H | CH |
| 2-194 | CH$_3$ | 4-CF(CH$_3$)$_2$ | H | CH |

TABLE 3

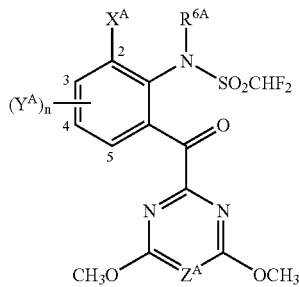

| Compound No. | $X^A$ | $(Y^A)_n$ | $R^{6A}$ | $Z^A$ |
|---|---|---|---|---|
| 3-1 | H | H | CH$_3$ | CH |
| 3-2 | H | H | CH$_2$OCH$_3$ | CH |
| 3-3 | H | H | CH$_2$OCH$_2$CH$_3$ | CH |
| 3-4 | H | H | COCH$_3$ | CH |
| 3-5 | H | H | CO$_2$CH$_3$ | CH |
| 3-6 | H | H | CO$_2$CH$_2$CH$_3$ | CH |
| 3-7 | F | H | CH$_3$ | CH |
| 3-8 | F | H | CH$_2$OCH$_3$ | CH |
| 3-9 | F | H | CH$_2$OCH$_2$CH$_3$ | CH |
| 3-10 | F | H | COCH$_3$ | CH |
| 3-11 | F | H | CO$_2$CH$_3$ | CH |
| 3-12 | F | H | CO$_2$CH$_2$CH$_3$ | CH |
| 3-13 | F | H | SO$_2$CH$_3$ | CH |
| 3-14 | F | H | SO$_2$CHF$_2$ | CH |
| 3-15 | F | H | SO$_2$CH$_3$ | CH |
| 3-16 | F | H | SO$_2$CH$_2$Cl | CH |
| 3-17 | F | H | SO$_2$CH$_2$CH$_3$ | CH |
| 3-18 | F | H | SO$_2$CH$_2$CN | CH |
| 3-19 | Cl | H | CH$_3$ | CH |
| 3-20 | Cl | H | CH$_2$OCH$_3$ | CH |
| 3-21 | Cl | H | CH$_2$OCH$_2$CH$_3$ | CH |
| 3-22 | Cl | H | COCH$_3$ | CH |
| 3-23 | Cl | H | CO$_2$CH$_3$ | CH |
| 3-24 | Cl | H | SO$_2$CH$_2$CH$_3$ | CH |
| 3-25 | Cl | H | SO$_2$CH$_3$ | CH |
| 3-26 | Cl | H | SO$_2$CHF$_2$ | CH |
| 3-27 | Cl | H | SO$_2$CH$_3$ | CH |
| 3-28 | Cl | H | SO$_2$CH$_2$Cl | CH |
| 3-29 | Cl | H | SO$_2$CH$_2$CH$_3$ | CH |
| 3-30 | Cl | H | SO$_2$CH$_2$CN | CH |
| 3-31 | H | H | H | N |
| 3-32 | H | H | CH$_3$ | N |
| 3-33 | H | H | CH$_2$OCH$_2$CH$_3$ | N |
| 3-34 | H | H | COCH$_3$ | N |
| 3-35 | H | H | CO$_2$CH$_3$ | N |
| 3-36 | H | H | CO$_2$CH$_2$CH$_3$ | N |
| 3-37 | F | H | CH$_3$ | N |
| 3-38 | F | H | CH$_2$OCH$_2$CH$_3$ | N |
| 3-39 | F | H | COCH$_3$ | N |
| 3-40 | F | H | CO$_2$CH$_3$ | N |
| 3-41 | F | H | CO$_2$CH$_2$CH$_3$ | N |
| 3-42 | Cl | H | CH$_3$ | N |
| 3-43 | Cl | H | CH$_2$OCH$_2$CH$_3$ | N |
| 3-44 | Cl | H | COCH$_3$ | N |
| 3-45 | Cl | H | CO$_2$CH$_3$ | N |
| 3-46 | Cl | H | CO$_2$CH$_2$CH$_3$ | N |
| 3-47 | H | H | H | C—CH$_3$ |
| 3-48 | F | H | H | C—CH$_3$ |
| 3-49 | Cl | H | H | C—CH$_3$ |
| 3-50 | H | 4-F | H | CH |
| 3-51 | H | 5-F | H | CH |
| 3-52 | H | 3-Cl | H | CH |
| 3-53 | H | 4-Cl | H | CH |
| 3-54 | H | 5-Cl | H | CH |
| 3-55 | H | 3,5-F$_2$ | H | CH |
| 3-56 | H | 3,5-Cl$_2$ | H | CH |
| 3-57 | H | 4,5-F$_2$ | H | CH |
| 3-58 | H | 4,5-Cl$_2$ | H | CH |
| 3-59 | H | 3-CH$_3$ | H | CH |
| 3-60 | H | 4-CH$_3$ | H | CH |

TABLE 3-continued

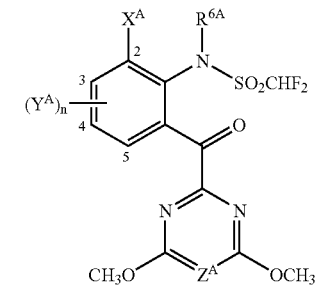

| Compound No. | $X^A$ | $(Y^A)_n$ | $R^{6A}$ | $Z^A$ |
|---|---|---|---|---|
| 3-61 | H | 5-CH$_3$ | H | CH |
| 3-62 | H | 3-CH$_3$ | H | CH |
| 3-63 | H | 4-CH$_3$ | H | CH |
| 3-64 | H | 5-CH$_3$ | H | CH |
| 3-65 | H | 3-CH$_2$OCH$_3$ | H | CH |
| 3-66 | H | 4-CH$_2$OCH$_3$ | H | CH |
| 3-67 | H | 5-CH$_2$OCH$_3$ | H | CH |
| 3-68 | H | 3-OCH$_3$ | H | CH |
| 3-69 | H | 4-OCH$_3$ | H | CH |
| 3-70 | H | 5-OCH$_3$ | H | CH |
| 3-71 | H | 3-CO$_2$CH$_3$ | H | CH |
| 3-72 | H | 4-CO$_2$CH$_3$ | H | CH |
| 3-73 | H | 5-CO$_2$CH$_3$ | H | CH |
| 3-74 | H | 4-SO$_2$CH$_3$ | H | CH |
| 3-75 | H | 5-SO$_2$CH$_3$ | H | CH |
| 3-76 | H | 3-SCH$_3$ | H | CH |
| 3-77 | H | 4-SCH$_3$ | H | CH |
| 3-78 | H | 5-SCH$_3$ | H | CH |
| 3-79 | H | 3-SOCH$_3$ | H | CH |
| 3-80 | H | 4-SOCH$_3$ | H | CH |
| 3-81 | H | 5-SOCH$_3$ | H | CH |
| 3-82 | H | 3-SO$_2$CH$_3$ | H | CH |
| 3-83 | H | 4-SO$_2$CF$_3$ | H | CH |
| 3-84 | H | 5-SO$_2$CF$_3$ | H | CH |
| 3-85 | H | 3-N(CH$_3$)$_2$ | H | CH |
| 3-86 | H | 4-N(CH$_3$)$_2$ | H | CH |
| 3-87 | H | 5-N(CH$_3$)$_2$ | H | CH |
| 3-88 | H | 3-NO$_2$ | H | CH |
| 3-89 | H | 4-NO$_2$ | H | CH |
| 3-90 | H | 5-NO$_2$ | H | CH |
| 3-91 | H | 3-CN | H | CH |
| 3-92 | H | 4-CN | H | CH |
| 3-93 | H | 5-CN | H | CH |
| 3-94 | H | 3-COCH$_3$ | H | CH |
| 3-95 | H | 4-COCH$_3$ | H | CH |
| 3-96 | H | 5-COCH$_3$ | H | CH |
| 3-97 | F | 3-F | H | CH |
| 3-98 | F | 4-F | H | CH |
| 3-99 | F | 5-F | H | CH |
| 3-100 | F | 3-Cl | H | CH |
| 3-101 | F | 4-Cl | H | CH |
| 3-102 | F | 5-Cl | H | CH |
| 3-103 | F | 3-CH$_3$ | H | CH |
| 3-104 | F | 4-CH$_3$ | H | CH |
| 3-105 | F | 5-CH$_3$ | H | CH |
| 3-106 | F | 3-OCH$_3$ | H | CH |
| 3-107 | F | 4-OCH$_3$ | H | CH |
| 3-108 | F | 5-OCH$_3$ | H | CH |
| 3-109 | F | 4-CN | H | CH |
| 3-110 | F | 3,4-F$_2$ | H | CH |
| 3-111 | F | 4,5-F$_2$ | H | CH |
| 3-112 | F | 4-F-3-Cl | H | CH |
| 3-113 | F | 3-F-5-Cl | H | CH |
| 3-114 | F | 5-F-4-CN | H | CH |
| 3-115 | F | 3-F-4-CF$_3$ | H | CH |
| 3-116 | F | 3-CF$_3$ | H | CH |
| 3-117 | F | 5-CF$_3$ | H | CH |
| 3-118 | F | 4-Br | H | CH |
| 3-119 | F | 5-OCH$_3$-4-F | H | CH |
| 3-120 | Cl | 3-F | H | CH |

TABLE 3-continued

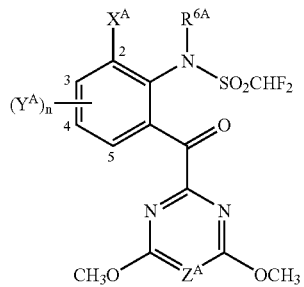

| Compound No. | $X^A$ | $(Y^A)_n$ | $R^{6A}$ | $Z^A$ |
|---|---|---|---|---|
| 3-121 | Cl | 4-F | H | CH |
| 3-122 | Cl | 5-F | H | CH |
| 3-123 | Cl | 3-Cl | H | CH |
| 3-124 | Cl | 4-Cl | H | CH |
| 3-125 | Cl | 5-Cl | H | CH |
| 3-126 | Cl | 3-CH$_3$ | H | CH |
| 3-127 | Cl | 4-CH$_3$ | H | CH |
| 3-128 | Cl | 5-CH$_3$ | H | CH |
| 3-129 | Cl | 3-OCH$_3$ | H | CH |
| 3-130 | Cl | 4-OCH$_3$ | H | CH |
| 3-131 | Cl | 5-OCH$_3$ | H | CH |
| 3-132 | Cl | 4-SO$_2$CH$_3$ | H | CH |
| 3-133 | Cl | 3-SCF$_3$ | H | CH |
| 3-134 | Cl | 4-SCF$_3$ | H | CH |
| 3-135 | Cl | 5-SCF$_3$ | H | CH |
| 3-136 | Cl | 3-SOCF$_3$ | H | CH |
| 3-137 | Cl | 4-SOCF$_3$ | H | CH |
| 3-138 | Cl | 5-SOCF$_3$ | H | CH |
| 3-139 | Cl | 3-SO$_2$CF$_3$ | H | CH |
| 3-140 | Cl | 4-SO$_2$CF$_3$ | H | CH |
| 3-141 | Cl | 5-SO$_2$CF$_3$ | H | CH |
| 3-142 | Cl | 4-CN | H | CH |
| 3-143 | Cl | 3,4-Cl$_2$ | H | CH |
| 3-144 | Cl | 4,5-Cl$_2$ | H | CH |
| 3-145 | Cl | 3-Cl-4-CF$_3$ | H | CH |
| 3-146 | Cl | 4-Cl-3-CH$_3$ | H | CH |
| 3-147 | Cl | 5-OCF$_3$-4-F | H | CH |
| 3-148 | Cl | 4-SO$_2$CH$_3$ | H | CH |
| 3-149 | Cl | 4-CF$_3$ | H | CH |
| 3-150 | Cl | 5-CF$_3$ | H | CH |
| 3-151 | CHO | H | H | CH |
| 3-152 | COCH$_3$ | H | H | CH |
| 3-153 | COcPr | H | H | CH |
| 3-154 | CO$_2$CH$_3$ | H | H | CH |
| 3-155 | CO$_2$CH$_2$CH$_3$ | H | H | CH |
| 3-156 | CON(CH$_3$)$_2$ | H | H | CH |
| 3-157 | N(CH$_3$)$_2$ | H | H | CH |
| 3-158 | OCH$_3$ | H | H | CH |
| 3-159 | OCF$_3$ | H | H | CH |
| 3-160 | OCHF$_2$ | H | H | CH |
| 3-161 | OPh | H | H | CH |
| 3-162 | SO$_2$CH$_3$ | H | H | CH |
| 3-163 | SCF$_3$ | H | H | CH |
| 3-164 | SOCF$_3$ | H | H | CH |
| 3-165 | SO$_2$CF$_3$ | H | H | CH |
| 3-166 | CN | H | H | CH |
| 3-167 | NO$_2$ | H | H | CH |
| 3-168 | OSO$_2$CH$_3$ | H | H | CH |
| 3-169 | OSO$_2$CF$_3$ | H | H | CH |
| 3-170 | OSO$_2$CHF$_2$ | H | H | CH |
| 3-171 | OSO$_2$CH$_2$Cl | H | H | CH |
| 3-172 | OSO$_2$CH$_2$CF$_3$ | H | H | CH |
| 3-173 | OSO$_2$CH$_2$CN | H | H | CH |
| 3-174 | COCH$_3$ | H | H | N |
| 3-175 | COcPr | H | H | N |
| 3-176 | CO$_2$CH$_3$ | H | H | N |
| 3-177 | CO$_2$CH$_2$CH$_3$ | H | H | N |

TABLE 4

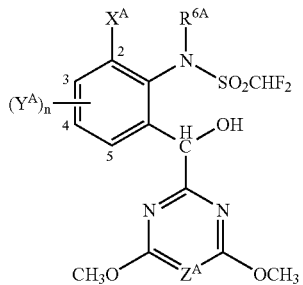

| Compound No. | $X^A$ | $(Y^A)_n$ | $R^{6A}$ | $Z^A$ |
|---|---|---|---|---|
| 4-1 | H | H | $CH_3$ | CH |
| 4-2 | H | H | $CH_2OCH_3$ | CH |
| 4-3 | H | H | $CH_2OCH_2CH_3$ | CH |
| 4-4 | H | H | $COCH_3$ | CH |
| 4-5 | H | H | $CO_2CH_3$ | CH |
| 4-6 | H | H | $CO_2CH_2CH_3$ | CH |
| 4-7 | H | H | $SO_2CH_3$ | CH |
| 4-8 | H | H | $SO_2CHF_2$ | CH |
| 4-9 | H | H | $SO_2CF_3$ | CH |
| 4-10 | H | H | $SO_2CH_2Cl$ | CH |
| 4-11 | H | H | $SO_2CH_2CH_3$ | CH |
| 4-12 | H | H | $SO_2CH_2CN$ | CH |
| 4-13 | F | H | $CH_3$ | CH |
| 4-14 | F | H | $CH_2OCH_3$ | CH |
| 4-15 | F | H | $CH_2OCH_2CH_3$ | CH |
| 4-16 | F | H | $COCH_3$ | CH |
| 4-17 | F | H | $CO_2CH_3$ | CH |
| 4-18 | F | H | $CO_2CH_2CH_3$ | CH |
| 4-19 | F | H | $SO_2CH_3$ | CH |
| 4-20 | F | H | $SO_2CHF_2$ | CH |
| 4-21 | F | H | $SO_2CF_3$ | CH |
| 4-22 | F | H | $SO_2CH_2Cl$ | CH |
| 4-23 | F | H | $SO_2CH_2CH_3$ | CH |
| 4-24 | F | H | $SO_2CH_2CN$ | CH |
| 4-25 | Cl | H | $CH_3$ | CH |
| 4-26 | Cl | H | $CH_2OCH_3$ | CH |
| 4-27 | Cl | H | $CH_2OCH_2CH_3$ | CH |
| 4-28 | Cl | H | $COCH_3$ | CH |
| 4-29 | Cl | H | $CO_2CH_3$ | CH |
| 4-30 | Cl | H | $CO_2CH_2CH_3$ | CH |
| 4-31 | Cl | H | $SO_2CH_3$ | CH |
| 4-32 | Cl | H | $SO_2CHF_2$ | CH |
| 4-33 | Cl | H | $SO_2CH_3$ | CH |
| 4-34 | Cl | H | $SO_2CH_2Cl$ | CH |
| 4-35 | Cl | H | $SO_2CH_2CF_3$ | CH |
| 4-36 | Cl | H | $SO_2CH_2CN$ | CH |
| 4-37 | H | H | H | N |
| 4-38 | H | H | $CH_3$ | N |
| 4-39 | H | H | $CH_2OCH_2CH_3$ | N |
| 4-40 | H | H | $COCH_3$ | N |
| 4-41 | H | H | $CO_2CH_3$ | N |
| 4-42 | H | H | $CO_2CH_2CH_3$ | N |
| 4-43 | F | H | $CH_3$ | N |
| 4-44 | F | H | $CH_2OCH_2CH_3$ | N |
| 4-45 | F | H | $COCH_3$ | N |
| 4-46 | F | H | $CO_2CH_3$ | N |
| 4-47 | F | H | $CO_2CH_2CH_3$ | N |
| 4-48 | Cl | H | $CH_3$ | N |
| 4-49 | Cl | H | $CH_2OCH_2CH_3$ | N |
| 4-50 | Cl | H | $COCH_3$ | N |
| 4-51 | Cl | H | $CO_2CH_3$ | N |
| 4-52 | Cl | H | $CO_2CH_2CH_3$ | N |
| 4-53 | H | H | H | $C-CH_3$ |
| 4-54 | F | H | H | $C-CH_3$ |
| 4-55 | Cl | H | H | $C-CH_3$ |
| 4-56 | H | 5-Cl | H | CH |
| 4-57 | H | 3,5-$F_2$ | H | CH |
| 4-58 | H | 3,5-$Cl_2$ | H | CH |
| 4-59 | H | 4,5-$F_2$ | H | CH |
| 4-60 | H | 4,5-$Cl_2$ | H | CH |
| 4-61 | H | 3-$CH_3$ | H | CH |
| 4-62 | H | 4-$CH_3$ | H | CH |
| 4-63 | H | 5-$CH_3$ | H | CH |
| 4-64 | H | 3-$CH_3$ | H | CH |
| 4-65 | H | 4-$CH_3$ | H | CH |
| 4-66 | H | 5-$CH_3$ | H | CH |
| 4-67 | H | 3-$CH_2OCH_3$ | H | CH |
| 4-68 | H | 4-$CH_2OCH_3$ | H | CH |
| 4-69 | H | 5-$CH_2OCH_3$ | H | CH |
| 4-70 | H | 3-$OCH_3$ | H | CH |
| 4-71 | H | 4-$OCH_3$ | H | CH |
| 4-72 | H | 5-$OCH_3$ | H | CH |
| 4-73 | H | 3-$CO_2CH_3$ | H | CH |
| 4-74 | H | 4-$CO_2CH_3$ | H | CH |
| 4-75 | H | 5-$CO_2CH_3$ | H | CH |
| 4-76 | H | 3-$SO_2CH_3$ | H | CH |
| 4-77 | H | 4-$SO_2CH_3$ | H | CH |
| 4-78 | H | 5-$SO_2CH_3$ | H | CH |
| 4-79 | H | 3-$SCH_3$ | H | CH |
| 4-80 | H | 4-$SCH_3$ | H | CH |
| 4-81 | H | 5-$SCH_3$ | H | CH |
| 4-82 | H | 3-$SOCF_3$ | H | CH |
| 4-83 | H | 4-$SOCF_3$ | H | CH |
| 4-84 | H | 5-$SOCF_3$ | H | CH |
| 4-85 | H | 3-$SO_2CF_3$ | H | CH |
| 4-86 | H | 4-$SO_2CF_3$ | H | CH |
| 4-87 | H | 5-$SO_2CF_3$ | H | CH |
| 4-88 | H | 3-$N(CH_3)_2$ | H | CH |
| 4-89 | H | 4-$N(CH_3)_2$ | H | CH |
| 4-90 | H | 5-$N(CH_3)_2$ | H | CH |
| 4-91 | H | 3-$NO_2$ | H | CH |
| 4-92 | H | 4-$NO_2$ | H | CH |
| 4-93 | H | 5-$NO_2$ | H | CH |
| 4-94 | H | 3-CN | H | CH |
| 4-95 | H | 4-CN | H | CH |
| 4-96 | H | 5-CN | H | CH |
| 4-97 | H | 3-$COCH_3$ | H | CH |
| 4-98 | H | 4-$COCH_3$ | H | CH |
| 4-99 | H | 5-$COCH_3$ | H | CH |
| 4-100 | F | 3-F | H | CH |
| 4-101 | F | 4-F | H | CH |
| 4-102 | F | 5-F | H | CH |
| 4-103 | F | 3-Cl | H | CH |
| 4-104 | F | 4-Cl | H | CH |
| 4-105 | F | 5-Cl | H | CH |
| 4-106 | F | 3-$CH_3$ | H | CH |
| 4-107 | F | 4-$CH_3$ | H | CH |
| 4-108 | F | 5-$CH_3$ | H | CH |
| 4-109 | F | 3-$OCH_3$ | H | CH |
| 4-110 | F | 4-$OCH_3$ | H | CH |
| 4-111 | F | 5-$OCH_3$ | H | CH |
| 4-112 | F | 4-CN | H | CH |
| 4-113 | F | 3,4-$F_2$ | H | CH |
| 4-114 | F | 4,5-$F_2$ | H | CH |
| 4-115 | F | 4-F-3-Cl | H | CH |
| 4-116 | F | 3-F-5-Cl | H | CH |
| 4-117 | F | 5-F-4-CN | H | CH |
| 4-118 | F | 3-F-4-$CF_3$ | H | CH |
| 4-119 | F | 3-$CF_3$ | H | CH |
| 4-120 | F | 5-$CF_3$ | H | CH |

TABLE 4-continued

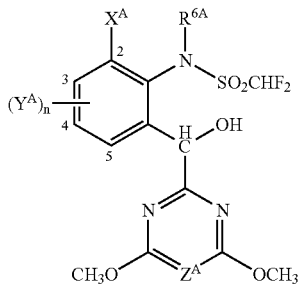

| Compound No. | $X^A$ | $(Y^A)_n$ | $R^{6A}$ | $Z^A$ |
|---|---|---|---|---|
| 4-121 | F | 4-Br | H | CH |
| 4-122 | F | 5-OCF$_3$-4-F | H | CH |
| 4-123 | Cl | 3-F | H | CH |
| 4-124 | Cl | 4-F | H | CH |
| 4-125 | Cl | 5-F | H | CH |
| 4-126 | Cl | 3-Cl | H | CH |
| 4-127 | Cl | 4-Cl | H | CH |
| 4-128 | Cl | 5-Cl | H | CH |
| 4-129 | Cl | 3-CH$_3$ | H | CH |
| 4-130 | Cl | 4-CH$_3$ | H | CH |
| 4-131 | Cl | 5-CH$_3$ | H | CH |
| 4-132 | Cl | 3-OCH$_3$ | H | CH |
| 4-133 | Cl | 4-OCH$_3$ | H | CH |
| 4-134 | Cl | 5-OCH$_3$ | H | CH |
| 4-135 | Cl | 4-SO$_2$CH$_3$ | H | CH |
| 4-136 | Cl | 3-SCF$_3$ | H | CH |
| 4-137 | Cl | 4-SCF$_3$ | H | CH |
| 4-138 | Cl | 5-SCF$_3$ | H | CH |
| 4-139 | Cl | 3-SOCF$_3$ | H | CH |
| 4-140 | Cl | 4-SOCF$_3$ | H | CH |
| 4-141 | Cl | 5-SOCF$_3$ | H | CH |
| 4-142 | Cl | 3-SO$_2$CF$_3$ | H | CH |
| 4-143 | Cl | 4-SO$_2$CF$_3$ | H | CH |
| 4-144 | Cl | 5-SO$_2$CF$_3$ | H | CH |
| 4-145 | Cl | 4-CN | H | CH |
| 4-146 | Cl | 3,4-Cl$_2$ | H | CH |
| 4-147 | Cl | 4,5-Cl$_2$ | H | CH |
| 4-148 | Cl | 3-Cl-4-CF$_3$ | H | CH |
| 4-149 | Cl | 4-Cl-3-CH$_3$ | H | CH |
| 4-150 | Cl | 5-OCF$_3$-4-F | H | CH |
| 4-151 | Cl | 4-SO$_2$CH$_3$ | H | CH |
| 4-152 | Cl | 4-CF$_3$ | H | CH |
| 4-153 | Cl | 5-CF$_3$ | H | CH |
| 4-154 | CHO | H | H | CH |
| 4-155 | COCH$_3$ | H | H | CH |
| 4-156 | COcPr | H | H | CH |
| 4-157 | CO$_2$CH$_3$ | H | H | CH |
| 4-158 | CO$_2$CH$_2$CH$_3$ | H | H | CH |
| 4-159 | CCN(CH$_3$)$_2$ | H | H | CH |
| 4-160 | N(CH$_3$)$_2$ | H | H | CH |
| 4-161 | OCH$_3$ | H | H | CH |
| 4-162 | OCF$_3$ | H | H | CH |
| 4-163 | OCHF$_2$ | H | H | CH |
| 4-164 | OPh | H | H | CH |
| 4-165 | SO$_2$CH$_3$ | H | H | CH |
| 4-166 | SCF$_3$ | H | H | CH |
| 4-167 | SOCF$_3$ | H | H | CH |
| 4-168 | SO$_2$CF$_3$ | H | H | CH |
| 4-169 | CN | H | H | CH |
| 4-170 | NO$_2$ | H | H | CH |
| 4-171 | OSO$_2$CH$_3$ | H | H | CH |
| 4-172 | OSO$_2$CF$_3$ | H | H | CH |
| 4-173 | OSO$_2$CHF$_2$ | H | H | CH |
| 4-174 | OSO$_2$CH$_2$Cl | H | H | CH |
| 4-175 | OSO$_2$CH$_2$CF$_3$ | H | H | CH |
| 4-176 | OSO$_2$CH$_2$CN | H | H | CH |
| 4-177 | COCH$_3$ | H | H | N |
| 4-178 | COcPr | H | H | N |
| 4-179 | CO$_2$CH$_3$ | H | H | N |
| 4-180 | CO$_2$CH$_2$CH$_3$ | H | H | N |
| 4-181 | H | 4-F | H | CH |
| 4-182 | H | 3-F-4-CH$_3$ | H | CH |
| 4-183 | H | 5-F-4-CH$_3$ | H | CH |
| 4-184 | CH$_3$ | 3-F | H | CH |
| 4-185 | H | 5-F | H | CH |
| 4-186 | H | 3-F | H | CH |
| 4-187 | CH$_3$ | 3-CH$_3$ | H | CH |

TABLE 5

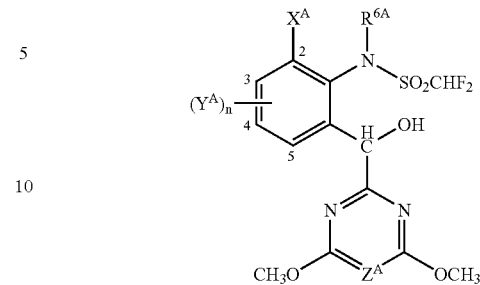

| Compound No. | $X^A$ | $(Y^A)_n$ | $R^{3A}$ | $R^{4A}$ | $R^{6A}$ | $Z^A$ |
|---|---|---|---|---|---|---|
| 5-1 | H | H | Cl | H | H | CH |
| 5-2 | F | H | Cl | H | H | CH |
| 5-3 | Cl | H | Cl | H | H | CH |
| 5-4 | COCH$_3$ | H | Cl | H | H | CH |
| 5-5 | H | H | Cl | H | H | N |
| 5-6 | F | H | Cl | H | H | N |
| 5-7 | Cl | H | Cl | H | H | N |
| 5-8 | H | H | F | H | H | CH |
| 5-9 | F | H | F | H | H | CH |
| 5-10 | Cl | H | F | H | H | CH |
| 5-11 | COCH$_3$ | H | F | H | H | CH |
| 5-12 | H | H | F | H | H | N |
| 5-13 | F | H | F | H | H | N |
| 5-14 | Cl | H | F | H | H | N |
| 5-15 | H | H | OCH$_3$ | H | H | CH |
| 5-16 | F | H | OCH$_3$ | H | H | CH |
| 5-17 | Cl | H | OCH$_3$ | H | H | CH |
| 5-18 | H | H | CH$_3$ | H | H | CH |
| 5-19 | F | H | CH$_3$ | H | H | CH |
| 5-20 | Cl | H | CH$_3$ | H | H | CH |
| 5-21 | H | H | CH | CH$_3$ | H | CH |
| 5-22 | H | H | CH | CH$_2$CH$_3$ | H | CH |
| 5-23 | H | H | CH | iPr | H | CH |
| 5-24 | F | H | CH | CH$_3$ | H | CH |
| 5-25 | F | H | CH | CH$_2$CH$_3$ | H | CH |
| 5-26 | F | H | CH | iPr | H | CH |
| 5-27 | Cl | H | CH | CH$_3$ | H | CH |
| 5-28 | Cl | H | CH | CH$_2$CH$_3$ | H | CH |
| 5-29 | Cl | H | CH | iPr | H | CH |
| 5-30 | H | H | SCH$_3$ | CH$_3$ | H | CH |

TABLE 5-continued

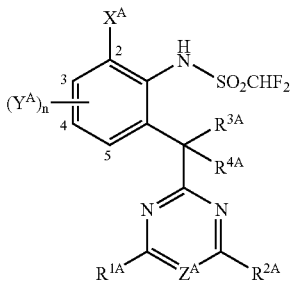

| Compound No. | $X^A$ | $(Y^A)_n$ | $R^{3A}$ | $R^{4A}$ | $R^{6A}$ | $Z^A$ |
|---|---|---|---|---|---|---|
| 5-31 | F | H | SCH$_3$ | CH$_3$ | H | CH |
| 5-32 | Cl | H | SCH$_3$ | CH$_3$ | H | CH |
| 5-33 | H | H | SO$_2$CH$_3$ | H | H | CH |
| 5-34 | F | H | SO$_2$CH$_3$ | H | H | CH |
| 5-35 | Cl | H | SO$_2$CH$_3$ | H | H | CH |
| 5-36 | H | H | SO$_2$CH$_3$ | H | H | N |
| 5-37 | F | H | SO$_2$CH$_3$ | H | H | N |
| 5-38 | Cl | H | SO$_2$CH$_3$ | H | H | N |

TABLE 6

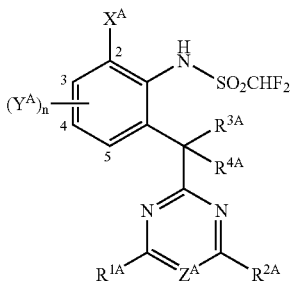

| Compound No. | $X^A$ | $(y^A)_n$ | $R^{1A}$ | $R^{2A}$ | $R^{3A}$ | $R^{4A}$ | $Z^A$ |
|---|---|---|---|---|---|---|---|
| 6-1 | H | H | H | H | H | H | CH |
| 6-2 | H | H | H | Cl | H | H | CH |
| 6-3 | H | H | H | CH$_3$ | H | H | CH |
| 6-4 | H | H | H | CF$_3$ | H | H | CH |
| 6-5 | H | H | H | OCH$_3$ | H | H | CH |
| 6-6 | H | H | H | OCH$_2$CH$_3$ | H | H | CH |
| 6-7 | H | H | H | OCH$_2$CF$_3$ | H | H | CH |
| 6-8 | H | H | H | SCH$_3$ | H | H | CH |
| 6-9 | H | H | CH$_3$ | Cl | H | H | CH |
| 6-10 | H | H | CH$_3$ | CH$_3$ | H | H | CH |
| 6-11 | H | H | CH$_3$ | iPr | H | H | CH |
| 6-12 | H | H | CH$_3$ | cycloPr | H | H | CH |
| 6-13 | H | H | CH$_3$ | CHF$_2$ | H | H | CH |
| 6-14 | H | H | CH$_3$ | CF$_3$ | H | H | CH |
| 6-15 | H | H | CH$_3$ | OCH$_3$ | H | H | CH |
| 6-16 | H | H | CH$_3$ | OCH$_2$CH$_3$ | H | H | CH |
| 6-17 | H | H | CH$_3$ | OCH$_2$CF$_3$ | H | H | CH |
| 6-18 | H | H | CH$_3$ | SCH$_3$ | H | H | CH |
| 6-19 | H | H | OCH$_3$ | Cl | H | H | CH |
| 6-20 | H | H | OCH$_3$ | CF$_3$ | H | H | CH |
| 6-21 | H | H | OCH$_3$ | OCH$_2$CH$_3$ | H | H | CH |
| 6-22 | H | H | OCH$_3$ | OCH$_2$CF$_3$ | H | H | CH |
| 6-23 | H | H | OCH$_3$ | SCH$_3$ | H | H | CH |
| 6-24 | H | H | CF$_3$ | Cl | H | H | CH |
| 6-25 | H | H | CF$_3$ | CF$_3$ | H | H | CH |
| 6-26 | H | H | CF$_3$ | OCH$_2$CH$_3$ | H | H | CH |
| 6-27 | H | H | CF$_3$ | OCH$_2$CF$_3$ | H | H | CH |
| 6-28 | H | H | CF$_3$ | SCH$_3$ | H | H | CH |
| 6-29 | H | H | OCH$_2$CH$_3$ | Cl | H | H | CH |

TABLE 6-continued

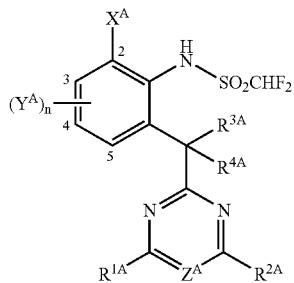

| Compound No. | $X^A$ | $(y^A)_n$ | $R^{1A}$ | $R^{2A}$ | $R^{3A}$ | $R^{4A}$ | $Z^A$ |
|---|---|---|---|---|---|---|---|
| 6-30 | H | H | OCH$_2$CH$_3$ | OCH$_2$CH$_3$ | H | H | CH |
| 6-31 | H | H | OCH$_2$CH$_3$ | SCH$_3$ | H | H | CH |
| 6-32 | H | H | SCH$_3$ | H | H | H | CH |
| 6-33 | H | H | SCH$_3$ | Cl | H | H | CH |
| 6-34 | F | H | CH$_3$ | Cl | H | H | CH |
| 6-35 | F | H | CH$_3$ | CH$_3$ | H | H | CH |
| 6-36 | F | H | CH$_3$ | CF$_3$ | H | H | CH |
| 6-37 | F | H | CH$_3$ | OCH$_3$ | H | H | CH |
| 6-38 | F | H | CH$_3$ | SCH$_3$ | H | H | CH |
| 6-39 | F | H | OCH$_3$ | Cl | H | H | CH |
| 6-40 | F | H | OCH$_3$ | CF$_3$ | H | H | CH |
| 6-41 | F | H | OCH$_3$ | SCH$_3$ | H | H | CH |
| 6-42 | F | H | CF$_3$ | Cl | H | H | CH |
| 6-43 | F | H | CF$_3$ | CF$_3$ | H | H | CH |
| 6-44 | F | H | CF$_3$ | SCH$_3$ | H | H | CH |
| 6-45 | F | H | OCH$_2$CH$_3$ | Cl | H | H | CH |
| 6-46 | F | H | OCH$_2$CH$_3$ | OCH$_2$CH$_3$ | H | H | CH |
| 6-47 | F | H | OCH$_2$CH$_3$ | SCH$_3$ | H | H | CH |
| 6-48 | F | H | SCH$_3$ | Cl | H | H | CH |
| 6-49 | F | H | N(CH$_3$)$_2$ | N(CH$_3$)$_2$ | H | H | CH |
| 6-50 | Cl | H | CH$_3$ | Cl | H | H | CH |
| 6-51 | Cl | H | CH$_3$ | CH$_3$ | H | H | CH |
| 6-52 | Cl | H | CH$_3$ | CF$_3$ | H | H | CH |
| 6-53 | Cl | H | CH$_3$ | OCH$_3$ | H | H | CH |
| 6-54 | Cl | H | CH$_3$ | SCH$_3$ | H | H | CH |
| 6-55 | Cl | H | OCH$_3$ | Cl | H | H | CH |
| 6-56 | Cl | H | OCH$_3$ | CF$_3$ | H | H | CH |
| 6-57 | Cl | H | OCH$_3$ | OCH$_2$CH$_3$ | H | H | CH |
| 6-58 | Cl | H | OCH$_3$ | OCH$_2$CF$_3$ | H | H | CH |
| 6-59 | Cl | H | OCH$_3$ | SCH$_3$ | H | H | CH |
| 6-60 | Cl | H | CF$_3$ | Cl | H | H | CH |
| 6-61 | Cl | H | CF$_3$ | CF$_3$ | H | H | CH |
| 6-62 | Cl | H | CF$_3$ | SCH$_3$ | H | H | CH |
| 6-63 | Cl | H | OCH$_2$CH$_3$ | Cl | H | H | CH |
| 6-64 | Cl | H | OCH$_2$CH$_3$ | OCH$_2$CH$_3$ | H | H | CH |
| 6-65 | Cl | H | OCH$_2$CH$_3$ | SCH$_3$ | H | H | CH |
| 6-66 | Cl | H | SCH$_3$ | Cl | H | H | CH |
| 6-67 | Cl | H | N(CH$_3$)$_2$ | N(CH$_3$)$_2$ | H | H | CH |
| 6-68 | F | H | CH$_3$ | Cl | C=O | | CH |
| 6-69 | F | H | CH$_3$ | CH$_3$ | C=O | | CH |
| 6-70 | F | H | CH$_3$ | CF$_3$ | C=O | | CH |
| 6-71 | F | H | CH$_3$ | OCH$_3$ | C=O | | CH |
| 6-72 | F | H | CH$_3$ | SCH$_3$ | C=O | | CH |
| 6-73 | F | H | OCH$_3$ | Cl | C=O | | CH |
| 6-74 | F | H | OCH$_3$ | CF$_3$ | C=O | | CH |
| 6-75 | F | H | OCH$_3$ | SCH$_3$ | C=O | | CH |
| 6-76 | F | H | CF$_3$ | Cl | C=O | | CH |
| 6-77 | F | H | CF$_3$ | CF$_3$ | C=O | | CH |
| 6-78 | F | H | CF$_3$ | SCH$_3$ | C=O | | CH |
| 6-79 | F | H | OCH$_2$CH$_3$ | Cl | C=O | | CH |
| 6-80 | F | H | OCH$_2$CH$_3$ | OCH$_2$CH$_3$ | C=O | | CH |
| 6-81 | F | H | OCH$_2$CH$_3$ | SCH$_3$ | C=O | | CH |
| 6-82 | F | H | SCH$_3$ | Cl | C=O | | CH |
| 6-83 | F | H | N(CH$_3$)$_2$ | N(CH$_3$)$_2$ | C=O | | CH |
| 6-84 | Cl | H | CH$_3$ | Cl | C=O | | CH |
| 6-85 | Cl | H | CH$_3$ | CH$_3$ | C=O | | CH |
| 6-86 | Cl | H | CH$_3$ | CF$_3$ | C=O | | CH |
| 6-87 | Cl | H | CH$_3$ | OCH$_3$ | C=O | | CH |
| 6-88 | Cl | H | CH$_3$ | SCH$_3$ | C=O | | CH |
| 6-89 | Cl | H | OCH$_3$ | Cl | C=O | | CH |

TABLE 6-continued

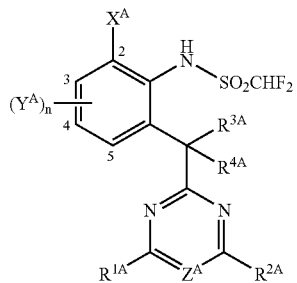

| Compound No. | $X^A$ | $(Y^A)_n$ | $R^{1A}$ | $R^{2A}$ | $R^{3A}$ | $R^{4A}$ | $Z^A$ |
|---|---|---|---|---|---|---|---|
| 6-90 | Cl | H | $OCH_3$ | $CF_3$ | | C=O | CH |
| 6-91 | Cl | H | $OCH_3$ | $OCH_2CH_3$ | | C=O | CH |
| 6-92 | Cl | H | $OCH_3$ | $OCH_2CF_3$ | | C=O | CH |
| 6-93 | Cl | H | $OCH_3$ | $SCH_3$ | | C=O | CH |
| 6-94 | Cl | H | $CF_3$ | Cl | | C=O | CH |
| 6-95 | Cl | H | $CF_3$ | $CF_3$ | | C=O | CH |
| 6-96 | Cl | H | $CF_3$ | $SCH_3$ | | C=O | CH |
| 6-97 | Cl | H | $OCH_2CH_3$ | Cl | | C=O | CH |
| 6-98 | Cl | H | $OCH_2CH_3$ | $OCH_2CH_3$ | | C=O | CH |
| 6-99 | Cl | H | $OCH_2CH_3$ | $SCH_3$ | | C=O | CH |
| 6-100 | Cl | H | $SCH_3$ | Cl | | C=O | CH |
| 6-101 | Cl | H | $N((CH_3)_2$ | $N(CH_3)_2$ | | C=O | CH |
| 6-102 | F | H | $CH_3$ | Cl | OH | H | CH |
| 6-103 | F | H | $CH_3$ | $CH_3$ | OH | H | CH |
| 6-104 | F | H | $CH_3$ | $CF_3$ | OH | H | CH |
| 6-105 | F | H | $CH_3$ | $OCH_3$ | OH | H | CH |
| 6-106 | F | H | $CH_3$ | $SCH_3$ | OH | H | CH |
| 6-107 | F | H | $OCH_3$ | Cl | OH | H | CH |
| 6-108 | F | H | $OCH_3$ | $CF_3$ | OH | H | CH |
| 6-109 | F | H | $OCH_3$ | $SCH_3$ | OH | H | CH |
| 6-110 | F | H | $CF_3$ | Cl | OH | H | CH |
| 6-111 | F | H | $CF_3$ | $CF_3$ | OH | H | CH |
| 6-112 | F | H | $CF_3$ | $SCH_3$ | OH | H | CH |
| 6-113 | F | H | $OCH_2CH_3$ | Cl | OH | H | CH |
| 6-114 | F | H | $OCH_2CH_3$ | $OCH_2CH_3$ | OH | H | CH |
| 6-115 | F | H | $OCH_2CH_3$ | $SCH_3$ | OH | H | CH |
| 6-116 | F | H | $SCH_3$ | Cl | OH | H | CH |
| 6-117 | F | H | $N(CH_3)_2$ | $N(CH_3)_2$ | OH | H | CH |
| 6-118 | Cl | H | $CH_3$ | Cl | OH | H | CH |
| 6-119 | Cl | H | $CH_3$ | $CH_3$ | OH | H | CH |
| 6-120 | Cl | H | $CH_3$ | $CF_3$ | OH | H | CH |
| 6-121 | Cl | H | $CH_3$ | $OCH_3$ | OH | H | CH |
| 6-122 | Cl | H | $CH_3$ | $SCH_3$ | OH | H | CH |
| 6-123 | Cl | H | $OCH_3$ | Cl | OH | H | CH |
| 6-124 | Cl | H | $OCH_3$ | $CF_3$ | OH | H | CH |
| 6-125 | Cl | H | $OCH_3$ | $OCH_2CH_3$ | OH | H | CH |
| 6-126 | Cl | H | $OCH_3$ | $OCH_2CF_3$ | OH | H | CH |
| 6-127 | Cl | H | $OCH_3$ | $SCH_3$ | OH | H | CH |
| 6-128 | Cl | H | $CF_3$ | Cl | OH | H | CH |
| 6-129 | Cl | H | $CF_3$ | $CF_3$ | OH | H | CH |
| 6-130 | Cl | H | $CF_3$ | $SCH_3$ | OH | H | CH |
| 6-131 | Cl | H | $OCH_2CH_3$ | Cl | OH | H | CH |
| 6-132 | Cl | H | $OCH_2CH_3$ | $OCH_2CH_3$ | OH | H | CH |
| 6-133 | Cl | H | $OCH_2CH_3$ | $SCH_3$ | OH | H | CH |
| 6-134 | Cl | H | $SCH_3$ | Cl | OH | H | CH |
| 6-135 | Cl | H | $N(CH_3)_2$ | $N(CH_3)_2$ | OH | H | CH |

TABLE 7

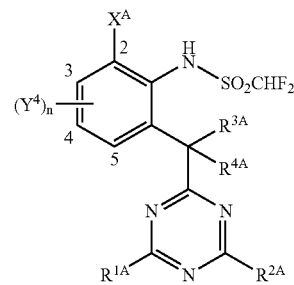

| Compound No. | $X^A$ | $(Y^A)_n$ | $R^{1A}$ | $R^{2A}$ | $R^{3A}$ | $R^{4A}$ |
|---|---|---|---|---|---|---|
| 7-1 | F | H | H | H | H | H |
| 7-2 | F | H | $CH_3$ | Cl | H | H |
| 7-3 | F | H | $CH_3$ | $CH_3$ | H | H |
| 7-4 | F | H | $CH_3$ | $OCH_3$ | H | H |
| 7-5 | F | H | $CH_3$ | $OCH_2CF_3$ | H | H |
| 7-6 | F | H | $OCH_3$ | Cl | H | H |
| 7-7 | F | H | $OCH_3$ | $OCH_2CF_3$ | H | H |
| 7-8 | F | H | $N(CH_3)_2$ | $N(CH_3)_2$ | H | H |
| 7-9 | F | H | H | H | | C=O |
| 7-10 | F | H | $CH_3$ | Cl | | C=O |
| 7-11 | F | H | $CH_3$ | $CH_3$ | | C=O |
| 7-12 | F | H | $CH_3$ | $OCH_3$ | | C=O |
| 7-13 | F | H | $CH_3$ | $OCH_2CF_3$ | | C=O |
| 7-14 | F | H | $OCH_3$ | Cl | | C=O |
| 7-15 | F | H | $OCH_3$ | $OCH_2CF_3$ | | C=O |
| 7-16 | F | H | $N(CH_3)_2$ | $N(CH_3)_2$ | | C=O |
| 7-17 | F | H | H | H | OH | H |
| 7-18 | F | H | $CH_3$ | Cl | OH | H |
| 7-19 | F | H | $CH_3$ | $CH_3$ | OH | H |
| 7-20 | F | H | $CH_3$ | $OCH_3$ | OH | H |
| 7-21 | F | H | $CH_3$ | $OCH_2CF_3$ | OH | H |
| 7-22 | F | H | $OCH_3$ | Cl | OH | H |
| 7-23 | F | H | $OCH_3$ | $OCH_2CF_3$ | OH | H |
| 7-24 | F | H | $N(CH_3)_2$ | $N(CH_3)_2$ | OH | H |
| 7-25 | Cl | H | H | H | H | H |
| 7-26 | Cl | H | $CH_3$ | Cl | H | H |
| 7-27 | Cl | H | $CH_3$ | $CH_3$ | H | H |
| 7-28 | Cl | H | $CH_3$ | $OCH_3$ | H | H |
| 7-29 | Cl | H | $CH_3$ | $OCH_2CF_3$ | H | H |
| 7-30 | Cl | H | $OCH_3$ | Cl | H | H |
| 7-31 | Cl | H | $OCH_3$ | $OCH_2CF_3$ | H | H |
| 7-32 | Cl | H | $N(CH_3)_2$ | $N(CH_3)_2$ | H | H |
| 7-33 | Cl | H | H | H | | C=O |
| 7-34 | Cl | H | $CH_3$ | Cl | | C=O |
| 7-35 | Cl | H | $CH_3$ | $CH_3$ | | C=O |
| 7-36 | Cl | H | $CH_3$ | $OCH_3$ | | C=O |
| 7-37 | Cl | H | $CH_3$ | $OCH_2CF_3$ | | C=O |
| 7-38 | Cl | H | $OCH_3$ | Cl | | C=O |
| 7-39 | Cl | H | $OCH_3$ | $OCH_2CF_3$ | | C=O |
| 7-40 | Cl | H | $N(CH_3)_2$ | $N(CH_3)_2$ | | C=O |
| 7-41 | Cl | H | H | H | OH | H |
| 7-42 | Cl | H | $CH_3$ | Cl | OH | H |
| 7-43 | Cl | H | $CH_3$ | $CH_3$ | OH | H |
| 7-44 | Cl | H | $CH_3$ | $OCH_3$ | OH | H |
| 7-45 | Cl | H | $CH_3$ | $OCH_2CF_3$ | OH | H |
| 7-46 | Cl | H | $OCH_3$ | Cl | OH | H |
| 7-47 | Cl | H | $OCH_3$ | $OCH_2CF_3$ | OH | H |
| 7-48 | Cl | H | $N(CH_3)_2$ | $N(CH_3)_2$ | OH | H |

TABLE 8

| Compound No. | Physical and Chemical Properties (mp (° C.), $n^D{}_{20}$ or $^1$H-NMR(300MHz, $CDCl_3$) δ) |
|---|---|
| 1-14 | 2.07(3H, s), 3.98(6H, s), 5.30(1H, s), 5.95(1H, s), 6.62(1H, t), 7.09-7.16(1H, m), 7.20-7.25(1H, m), 7.45-7.47(1H, m) |
| 1-27 | 2.07(3H, s), 3.94(6H, s), 5.63(1H, s), 5.90(1H, s), 6.76(1H, t), 7.26-7.31(1H, m), 7.38-7.41(1H, m), 7.90-7.93(1H, m), 9.97(1H, br) |
| 1-46 | 2.08(3H, s), 4.10(6H, s), 5.31(1H, s), 6.63(1H, t), 7.15-7.73(3H, m), 9.75(1H, br) |
| 1-64 | 2.04(3H, s), 3.98(6H, s), 5.25(1H, s), 5.94(1H, s), 6.45(1H, t), 7.24(1H, m), 7.64(2H, m), 11.04(1H, bs) |
| 1-65 | 2.04,(3H, s), 3.93(6H, s), 5.26(1H, s), 5.94(1H, s), 6.42(1H, t), 7.28(1H, m), 7.55(1H, m), 7.76(1H, m), 10.91(1H, bs) |

TABLE 8-continued

| Compound No. | Physical and Chemical Properties (mp (° C.), $n^D{}_{20}$ or $^1$H-NMR(300MHz, CDCl$_3$) δ) |
|---|---|
| 1-72 | 2.02(3H, s), 2.34(3H, s), 3.98(6H, s), 5.26(1H, br s), 5.92(1H, br s), 6.41(1H, t, J=54Hz), 7.10-7.30(1H, m), 7.50(2H, m), 10.8(1H, br s) |
| 1-112 | 2.17(3H, s), 4.00(6H, s), 5.60(1H, s), 6.00(1H, s), 6.62(1H, t), 6.95-7.03(1H, m), 7.07-7.15(1H, m), 11.73(1H, br) |
| 1-117 | 2.08(3H, s), 2.35(3H, s), 3.98(6H, s), 5.26(1H, s), 5.95(1H, s), 6.58(1H, t, J=54Hz), 6.94(1H, br d, J=11Hz), 7.26(1H, s), 10.7(1H, br s) |
| 2-1 | 100-104 |
| 2-14 | 3.34(3H, s), 3.88(6H, s), 4.09(1H, d, J=15Hz), 4.40(1H, d, J=15Hz), 5.88(1H, s), 6.40(1H, t), 7.03-7.09(1H, m), 7.27-7.34(2H, m) |
| 2-18 | 1.94(3H, s), 3.87(6H, s), 4.10(1H, d, J=15Hz), 4.30(1H, d, J=15Hz), 5.89(1H, s), 6.97(1H, t), 7.14-7.17(1H, m), 7.33-7.45(2H, m) |
| 2-31 | 1.91(3H, s), 3.86(6H, s), 4.33(2H, s), 5.90(1H, s), 7.05(1H, t), 7.35-7.48(3H, m) |
| 2-32 | 3.38(3H, m), 3.88(6H, s), 4.12(1H, d), 4.34(1H, d), 5.89(1H, s), 6.58(1H, t), 7.28-7.44(3H, m) |
| 2-40 | 4.06(6H, s), 4.14(2H, s), 6.33(1H, t), 7.20(1H), 7.31(1H), 7.36(1H), 7.60(1H), 10.75(1H, s) |
| 2-46 | 3.27(3H, s), 4.06-4.14(8H), 6.21(1H, t), 7.39(1H), 7.64(1H), 7.66(1H) |
| 2-61 | 76-80 |
| 2-62 | 78-81 |
| 2-63 | 98-100 |
| 2-64 | 4.11(6H, s), 4.47(2H, s), 6.43(1H, t), 6.82(1H, t), 7.25(1H, m), 7.52(2H, m) |
| 2-65 | 3.97(6H, s), 4.13(2H, s), 5.93(1H, s), 6.32(1H, t), 7.22-7.54(3H, m), 11.36(1H, bs) |
| 2-66 | 3.97(6H, m), 4.43(2H, s), 5.94(1H, s), 6.33(1H, t), 7.16-7.54(3H, m), 11.50(1H, bs) |
| 2-67 | 106-109 |
| 2-68 | 3.94(6H, s), 4.37(2H, s), 5.95(1H, s), 6.35(1H, t), 7.31(1H, s), 7.55(1H, s), 11.63(1H, bs) |
| 2-71 | 106-109 |
| 2-72 | 116-117 |
| 2-73 | 106-109 |
| 2-110 | 3.96(6H, s), 4.20(2H, s), 5.94(1H, s), 6.56(1H, t), 6.95-7.20(2H, m) |
| 2-111 | 3.96(6H, s), 4.23(2H, s), 5.95(1H, s), 6.51(1H, t), 6.85(1H, m), 6.98(1H, m) |
| 2-112 | 3.96(6H, s), 4.31(2H, s), 5.95(1H, s), 6.76(1H, t), 6.95-7.11(2H, m), 11.24(1H, br) |
| 2-114 | 3.96(6H, s), 4.21(2H, s), 5.95(1H, s), 6.53(1H, t), 7.10-7.23(2H, m), 11.1(1H, bs) |
| 2-115 | 3.96(6H), 4.48(2H, s), 5.95(1H, s), 7.03(1H), 7.30(1H), 11.25(1H, s) |
| 2-117 | 145-149 |
| 2-118 | 131-133 |
| 2-124 | 121-122 |
| 2-125 | 111-115 |
| 2-131 | 137-140 |
| 2-136 | 3.95(6H, s), 4.28(2H, s), 5.94(1H, s), 6.70(1H, t), 7.29(1H, d), 7.37(1H, d), 11.25(1H, br) |
| 2-137 | 3.95(6H, s), 4.26(2H, s), 5.95(1H, s), 6.67(1H, t), 7.35(1H, d), 7.40(1H, d), 11.03(1H, s) |
| 2-138 | 3.95(6H, s), 4.56(2H, s), 5.95(1H, s), 6.72(1H, t), 7.31-7.32(2H, m), 11.23(1H, br) |
| 2-140 | 132-136 |
| 2-164 | 3.99(6H, s), 4.33(2H, s), 5.97(1H, s), 6.46(1H, t), 7.41(1H, t), 7.67(1H, dd), 7.91(1H, dd), 10.31(1H, s) |
| 2-167 | 3.91(6H, s), 4.37(2H, s), 5.99(1H, s), 6.91(1H, t), 7.41(1H, t), 7.66(1H, dd), 7.87(1H, dd) |
| 2-168 | 3.92(3H, s), 3.96(6H, s), 4.28(2H, s), 5.93(1H, s), 6.46(1H, t), 7.26-7.31(1H, m), 7.54-7.56(1H, m), 7.75-7.78(1H, m), 11.27(1H, br) |
| 2-173 | 3.95(6H, s), 4.30(2H, s), 5.94(1H, s), 6.55(1H, t), 7.25-7.29(2H), 7.37(1H), 11.15(1H, s) |
| 2-190 | 120-124 |
| 2-191 | 0.48-0.55(1H, m), 0.78-0.86(1H, m), 0.99-1.08(3H, m), 3.85(6H, s), 4.14(1H, d), 4.39(1H, d), 5.87(1H, s), 7.05(1H, t), 7.36-7.52(3H, m) |
| 2-192 | 1.519 |
| 2-193 | 2.38(3H, br s), 3.95(6H, s), 4.22(2H, s), 5.91(1H, s), 6.36(1H, t, J=54Hz), 6.94(1H, dd, J=8.6, 8.6Hz), 7.20(1H, dd, J=8.6, 6.2Hz), 11.2(1H, br s) |
| 3-19 | 3.37(3H, s), 3.94(6H, s), 6.18(1H, t), 6.25(1H, t), 7.43(1H, t), 7.61(1H, dd), 7.67(1H, dd) |
| 3-22 | 2.91(3H, s), 3.93(6H, s), 6.20(1H, s), 6.77(1H, t), 7.53(1H, t), 7.62(1H, dd), 7.78(1H, dd) |
| 3-31 | 4.11(6H, s) 6.35(1H, t) 7.21(1H) 7.60-7.67(2H) 7.87(1H) 11.14(1H, s) |
| 3-37 | 3.27(3H, s), 4.12(6H, s), 6.20(1H, s), 7.27(1H), 7.53(1H), 7.65(1H) |
| 3-98 | 3.86(6H, s), 5.89(1H, t), 6.15(1H, s), 6.98-7.08(2H, m) (in CD$_3$CN) |
| 4-37 | 4.07(6H, s) 4.62(1H, s) 6.00(1H, s) 6.32(1H, t) 7.26-7.35(2H) 7.61(1H) 7.67(1H) 10.19(1H, s) |
| 4-57 | 3.95(6H, s), 6.01(1H, s), 6.11(1H, s), 6.29(1H, t, J=54Hz), 6.81-6.85(2H, m) |
| 4-59 | 4.01(6H, s), 5.95(1H, s), 6.02(1H, s), 6.32(1H, t, J=54Hz), 7.43-7.57(2H, m) |
| 4-61 | 100-103 |
| 4-63 | 2.57(3H, s), 3.92(6H, s), 5.95(1H, s), 6.20(1H, t, J=54Hz), 7.03(1H, d, J=7.0Hz), 7.17(1H, dd, J=7.7, 7.0Hz), 7.39(1H, d, J=7.7Hz) |
| 4-101 | 4.01(6H, s), 5.00(1H, s), 6.03(1H, s), 6.12(1H, bs), 6.53(1H, t), 6.87(1H, m), 7.30(1H, m) |
| 4-107 | 2.34(3H, s), 4.00(6H, s), 4.93(1H, br s), 5.99(1H, s), 6.10(1H, s), 6.57(1H, t, J=54Hz), 6.92(1H, br d, J=11Hz), 7.32(1H, br s), 10.4(1H, br s) |
| 4-130 | 182-183 |
| 4-184 | 2.39(3H, s), 3.97(6H, s), 4.90(1H, br s), 5.94(1H, s), 6.17(1H, br s), 6.39(1H, t, J=54Hz), 7.02(1H, dd, J=9.0, 9.0Hz), 7.54(1H, dd, J=9.0, 6.0Hz), 10.6(1H, br s) |
| 4-186 | 96-99 |
| 4-187 | 1.5543 |
| 5-2 | 4.01(6H, s), 6.01(1H, s), 6.04(1H, s), 6.63(1H, t), 7.16-7.37(3H, m), 11.09(1H, br) |
| 5-3 | 3.98(6H, s), 5.97(1H, s), 6.37(1H, t), 6.78(1H, t), 7.31(1H, t), 7.47(1H, dd), 7.75(1H, dd), 9.66(1H, br) |
| 5-31 | 1.73(3H, s), 2.09(3H, s), 3.84(6H, s), 5.96(1H, s), 6.49(1H, t), 7.14-7.32(3H, m), 8.26(1H, bs) |
| 5-33 | 3.13(3H, s) 3.97(6H, s) 5.92(1H, s) 6.08(1H, s) 6.41(1H, t) 7.30(1H) 7.43(1H) 7.69-7.75(2H) 8.65(1H, s) |
| 6-35 | 141-143 |
| 6-51 | 119-123 |
| 6-103 | 109-119 |

REFERENCE EXAMPLE 1

Preparation of an Intermediate

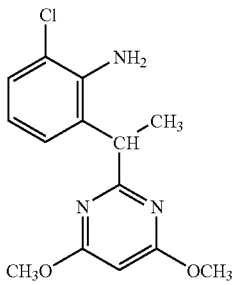

To a solution of 2-{1-methylthio-1-(2-amino-3-chlorophenyl)ethyl}-4,6-dimethoxypyrimidine 3 g (8.8 mmol) in 100 ml methanol, nickel (II) chloride hexahydrate 4.2 g (17.7 mmol) was added at 0° C. and the mixture was stirred for 30 minutes. Then, at the same temperature, sodium borohydride 1.35 g (35 mmol) was added little by little thereto. The solution was stirred at room temperature for 1 hour and then the solvent was distilled off. 2N-hydrochloric acid was added to the residue and then 28% aqueous ammonia was added and the mixture was extracted with ethyl acetate. The organic layer washed with an aqueous solution of sodium hydroxide and the solvent was distilled off. After washing with hexane, the deposited crystals were filtered to obtain 2-{1-(2-amino-3-chlorophenyl)ethyl}-4,6-dimethoxypyrimidine 2.12 g (82%).

$^1$H NMR (300 MHz, CDCl$_3$) δ 1.71 (3H, d) 3.90 (6H, s) 4.3 (1H, q) 5.09 (1H, bs) 5.85 (1H, s) 6.67 (1H, m) 7.25 (2H, m).

REFERENCE EXAMPLE 2

Preparation of an Intermediate

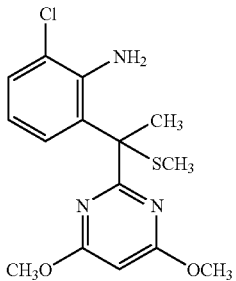

2-Chloroaniline 7 g (32.7 mmol) was dissolved in dichloromethane 100 ml and the solution was cooled to −65° C. To the solution a solution of t-butyl hypochlorite 3.55 g (32.7 mmol) in dichloromethane 10 ml was added dropwise and the solution was stirred at the same temperature for 10 minutes. Then a solution of 2-(1-methylthioethyl)-4,6-dimethoxypyrimidine in dichloromethane was added thereto dropwise and the solution was stirred at the same temperature for 1 hour. After a methanol solution of sodium methoxide 12.6 g (65.3 mmol) had been added dropwise and the mixed solution had been stirred at the same temperature for 10 minutes, the reaction solution was stirred until it came to room temperature. The reaction solution was poured into water and extracted with dichloromethane. The solvent was distilled off and the residue was purified with column chromatography (hexane/ethyl acetate=5/1) to obtain 2-{1-methylthio-1-(2-amino-3-chlorophenyl)ethyl}-4,6-dimethoxypyrimidine 10.0 g (90%).

$^1$H NMR (300 MHz, CDCl$_3$) δ 1.76 (3H, s) 2.07 (3H, s) 3.85 (6H, s) 4.76 (2H, bs) 5.88 (1H, s) 6.65 (1H, m) 7.25 (2H, m).

REFERENCE EXAMPLE 3

Preparation of an Intermediate

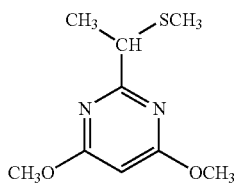

2-(1-Chloroethyl)-4,6-dimethoxypyrimidine 15.5 g (76.5 mmol) was dissolved in DMF 200 ml and sodium salt of methylmercaptan 5.4 g (76.5 mmol) was added thereto at room temperature. The solution was stirred at 50° C. for 1 hour. The reaction solution was poured into water and extracted with ethyl acetate. The solvent was distilled off and the residue was purified with column chromatography (hexane/ethyl acetate=5/1) to obtain 2-(1-methylthioethyl)-4,6-dimethoxypyrimidine 14.8 g (90%).

$^1$H NMR (300 MHz, CDCl$_3$) δ 1.66 (3H, d) 2.15 (3H, s) 3.9 (1H, q) 3.94 (6H, s) 5.9 (1H, s).

REFERENCE EXAMPLE 4

Preparation of an Intermediate

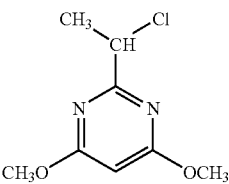

A mixed solution of an aqueous solution of potassium carbonate (potassium carbonate 109 g, 791 mmol, water 200 ml) and dichloromethane 400 ml was cooled to −15° C. and stirred with a mechanical stirrer. Diimidate of dimethyl malonate 25.7 g (198 mmol) was added thereto little by little and the mixture was stirred for 1 hour. To the solution at the same temperature a solution of chloropropionyl chloride 21.6 ml (218 mmol) in dichloromethane 40 ml was added dropwise. The solution was brought to room temperature and stirred for 3 hours. The reaction solution was poured into water and extracted with dichloromethane. The solvent was distilled off and the residue was purified with column chromatography (hexane/ethyl acetate=5/1) to obtain 2-(1-chloroethyl)-4,6-dimethoxypyrimidine 15.5 g (39%).

$^1$H NMR (300 MHz, CDCl$_3$) δ 1.87 (3H, d) 3.97 (6H, s) 4.98 (1H, q) 5.94 (1H, s).

Then examples of the compounds of the fungicidal sulfonanilides of the aforementioned formula (I), that include known compounds, are shown in the following Tables 9-21, and their physical and chemical properties are shown in Table 22. Abbreviations of each group in the tables are the same as described in the aforementioned Tables 1-7.

TABLE 9

|  | X | $(Y)_m$ | $R^5$ | $R^6$ | Z |
|---|---|---|---|---|---|
| 9-1 | H | H | $CH_3$ | H | CH |
| 9-2 | F | H | $CH_3$ | H | CH |
| 9-3 | Cl | H | $CH_3$ | H | CH |
| 9-4 | F | 4-F | $CH_3$ | H | CH |
| 9-5 | H | H | $CH_2Cl$ | H | CH |
| 9-6 | F | H | $CH_2Cl$ | H | CH |
| 9-7 | Cl | H | $CH_2Cl$ | H | CH |
| 9-8 | F | 4-F | $CH_2Cl$ | H | CH |
| 9-9 | H | H | $CH_2CF_3$ | H | CH |
| 9-10 | F | H | $CH_2CF_3$ | H | CH |
| 9-11 | Cl | H | $CH_2CF_3$ | H | CH |
| 9-12 | H | H | $CH_2CN$ | H | CH |
| 9-13 | F | H | $CH_2CN$ | H | CH |
| 9-14 | Cl | H | $CH_2CN$ | H | CH |
| 9-15 | F | 4-F | $CH_2CN$ | H | CH |
| 9-16 | H | H | $CH_2CO_2CH_3$ | H | CH |
| 9-17 | F | H | $CH_2CO_2CH_3$ | H | CH |
| 9-18 | Cl | H | $CH_2CO_2CH_3$ | H | CH |
| 9-19 | F | 4-F | $CH_2CO_2CH_3$ | H | CH |
| 9-20 | H | H | $CF_3$ | H | CH |
| 9-21 | F | H | $CF_3$ | H | CH |
| 9-22 | Cl | H | $CF_3$ | H | CH |
| 9-23 | F | 4-F | $CF_3$ | H | CH |
| 9-24 | H | H | $CHF_2$ | H | CH |
| 9-25 | F | H | $CHF_2$ | H | CH |
| 9-26 | Cl | H | $CHF_2$ | H | CH |
| 9-27 | H | H | $CH_2Ph$ | H | CH |
| 9-28 | F | H | $CH_2Ph$ | H | CH |
| 9-29 | Cl | H | $CH_2Ph$ | H | CH |
| 9-30 | H | H | $NHCO_2CH_3$ | H | CH |
| 9-31 | F | H | $NHCO_2CH_3$ | H | CH |
| 9-32 | Cl | H | $NHCO_2CH_3$ | H | CH |
| 9-33 | H | H | $CH_3$ | H | N |
| 9-34 | F | H | $CH_3$ | H | N |
| 9-35 | Cl | H | $CH_3$ | H | N |
| 9-36 | H | H | $CH_2Cl$ | H | N |
| 9-37 | F | H | $CH_2Cl$ | H | N |
| 9-38 | Cl | H | $CH_2Cl$ | H | N |
| 9-39 | H | H | $CH_2CF_3$ | H | N |
| 9-40 | F | H | $CH_2CF_3$ | H | N |
| 9-41 | Cl | H | $CH_2CF_3$ | H | N |
| 9-42 | H | H | $CH_2CN$ | H | N |
| 9-43 | F | H | $CH_2CN$ | H | N |
| 9-44 | Cl | H | $CH_2CN$ | H | N |
| 9-45 | H | H | $CH_2CO_2CH_3$ | H | N |
| 9-46 | F | H | $CH_2CO_2CH_3$ | H | N |
| 9-47 | Cl | H | $CH_2CO_2CH_3$ | H | N |
| 9-48 | H | H | $CHF_2$ | H | N |
| 9-49 | $CH_2OCH_3$ | H | $CHF_2$ | $CH_3$ | CH |

TABLE 10

|  | X | $(Y)_m$ | $R^5$ | $R^6$ |
|---|---|---|---|---|
| 10-1 | H | H | $CH_3$ | $CH_3$ |
| 10-2 | F | H | $CH_3$ | $CH_3$ |
| 10-3 | Cl | H | $CH_3$ | $CH_3$ |
| 10-4 | H | H | $CH_2CN$ | $CH_3$ |
| 10-5 | F | H | $CH_2CN$ | $CH_3$ |
| 10-6 | Cl | H | $CH_2CN$ | $CH_3$ |
| 10-7 | H | H | $CF_3$ | $CH_3$ |
| 10-8 | F | H | $CF_3$ | $CH_3$ |
| 10-9 | Cl | H | $CF_3$ | $CH_3$ |
| 10-10 | H | H | $CH_2Cl$ | $CH_3$ |
| 10-11 | F | H | $CH_2Cl$ | $CH_3$ |
| 10-12 | Cl | H | $CH_2Cl$ | $CH_3$ |

TABLE 11

|  | X | $(Y)_m$ | $R^5$ | $R^6$ | Z |
|---|---|---|---|---|---|
| 11-1 | H | H | $CH_3$ | H | CH |
| 11-2 | F | H | $CH_3$ | H | CH |
| 11-3 | F | H | $C_8H_{17}$ | H | CH |
| 11-4 | Cl | H | $CH_3$ | H | CH |
| 11-5 | F | 4-F | $CH_3$ | H | CH |
| 11-6 | H | H | $CH_2Cl$ | H | CH |
| 11-7 | F | H | $CH_2Cl$ | H | CH |
| 11-8 | Cl | H | $CH_2Cl$ | H | CH |
| 11-9 | F | 4-F | $CH_2Cl$ | H | CH |
| 11-10 | H | H | $CH_2CF_3$ | H | CH |
| 11-11 | F | H | $CH_2CF_3$ | H | CH |
| 11-12 | Cl | H | $CH_2CF_3$ | H | CH |
| 11-13 | H | H | $CH_2CN$ | H | CH |
| 11-14 | F | H | $CH_2CN$ | H | CH |
| 11-15 | Cl | H | $CH_2CN$ | H | CH |
| 11-16 | F | 4-F | $CH_2CN$ | H | CH |
| 11-17 | H | H | $CH_2CO_2CH_3$ | H | CH |
| 11-18 | F | H | $CH_2CO_2CH_3$ | H | CH |
| 11-19 | Cl | H | $CH_2CO_2CH_3$ | H | CH |
| 11-20 | F | 4-F | $CH_2CO_2CH_3$ | H | CH |
| 11-21 | H | H | $CF_3$ | H | CH |
| 11-22 | F | H | $CF_3$ | H | CH |
| 11-23 | Cl | H | $CF_3$ | H | CH |
| 11-24 | F | 4-F | $CF_3$ | H | CH |
| 11-25 | H | H | $CH_2Ph$ | H | CH |
| 11-26 | F | H | $CH_2Ph$ | H | CH |
| 11-27 | Cl | H | $CH_2Ph$ | H | CH |
| 11-28 | H | H | $NHCO_2CH_3$ | H | CH |
| 11-29 | F | H | $NHCO_2CH_3$ | H | CH |
| 11-30 | Cl | H | $NHCO_2CH_3$ | H | CH |

TABLE 11-continued

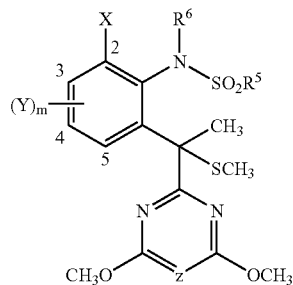

| | X | (Y)$_m$ | R$^5$ | R$^6$ | Z |
|---|---|---|---|---|---|
| 11-31 | H | H | CH$_3$ | H | N |
| 11-32 | F | H | CH$_3$ | H | N |
| 11-33 | Cl | H | CH$_3$ | H | N |
| 11-34 | H | H | CH$_2$Cl | H | N |
| 11-35 | F | H | CH$_2$Cl | H | N |
| 11-36 | Cl | H | CH$_2$Cl | H | N |
| 11-37 | H | H | CH$_2$CF$_3$ | H | N |
| 11-38 | F | H | CH$_2$CF$_3$ | H | N |
| 11-39 | Cl | H | CH$_2$CF$_3$ | H | N |
| 11-40 | H | H | CH$_2$CN | H | N |
| 11-41 | F | H | CH$_2$CN | H | N |
| 11-42 | Cl | H | CH$_2$CN | H | N |
| 11-43 | H | H | CH$_2$CO$_2$CH$_3$ | H | N |
| 11-44 | F | H | CH$_2$CO$_2$CH$_3$ | H | N |
| 11-45 | Cl | H | CH$_2$CO$_2$CH$_3$ | H | N |

TABLE 12

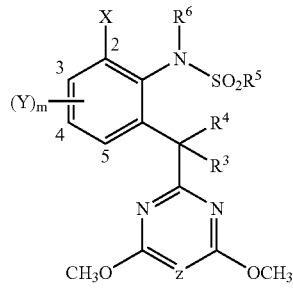

| | X | (Y)$_m$ | R$^3$ | R$^4$ | R$^5$ | R$^6$ | Z |
|---|---|---|---|---|---|---|---|
| 12-1 | F | 3-F | SCH$_3$ | H | CH$_3$ | H | CH |
| 12-2 | F | 3-F | SCH$_3$ | H | CH$_2$Cl | H | CH |
| 12-3 | F | 3-F | SCH$_3$ | H | CH$_2$CF$_3$ | H | CH |
| 12-4 | F | 3-F | SCH$_3$ | H | CH$_2$CN | H | CH |
| 12-5 | F | 3-F | SCH$_3$ | H | CF$_3$ | H | CH |
| 12-6 | F | 3-F | SCH$_3$ | H | CH$_2$CO$_2$CH$_3$ | H | CH |
| 12-7 | F | 3-F | SCH$_3$ | H | NHCO$_2$CH$_3$ | H | CH |
| 12-8 | F | 4-Cl | SCH$_3$ | H | CH$_3$ | H | CH |
| 12-9 | F | 4-Cl | SCH$_3$ | H | CH$_2$Cl | H | CH |
| 12-10 | F | 4-Cl | SCH$_3$ | H | CH$_2$CF$_3$ | H | CH |
| 12-11 | F | 4-Cl | SCH$_3$ | H | CH$_2$CN | H | CH |
| 12-12 | F | 4-Cl | SCH$_3$ | H | CF$_3$ | H | CH |
| 12-13 | F | 3,4-F$_2$ | SCH$_3$ | H | CH$_3$ | H | CH |
| 12-14 | F | 3,4-F$_2$ | SCH$_3$ | H | CH$_2$Cl | H | CH |
| 12-15 | F | 3,4-F$_2$ | SCH$_3$ | H | CH$_2$CF$_3$ | H | CH |
| 12-16 | F | 3,4-F$_2$ | SCH$_3$ | H | CH$_2$CN | H | CH |
| 12-17 | F | 3,4-F$_2$ | SCH$_3$ | H | CF$_3$ | H | CH |
| 12-18 | Cl | 4-F | SCH$_3$ | H | CH$_3$ | H | CH |
| 12-19 | Cl | 4-F | SCH$_3$ | H | CH$_2$Cl | H | CH |
| 12-20 | Cl | 4-F | SCH$_3$ | H | CH$_2$CF$_3$ | H | CH |
| 12-21 | Cl | 4-F | SCH$_3$ | H | CH$_2$CN | H | CH |
| 12-22 | Cl | 4-F | SCH$_3$ | H | CF$_3$ | H | CH |
| 12-23 | Cl | 4-CH$_3$ | SCH$_3$ | H | CH$_3$ | H | CH |
| 12-24 | Cl | 4-CH$_3$ | SCH$_3$ | H | CH$_2$Cl | H | CH |
| 12-25 | Cl | 4-CH$_3$ | SCH$_3$ | H | CH$_2$CF$_3$ | H | CH |
| 12-26 | Cl | 4-CH$_3$ | SCH$_3$ | H | CH$_2$CN | H | CH |
| 12-27 | Cl | 4-CH$_3$ | SCH$_3$ | H | CF$_3$ | H | CH |

TABLE 12-continued

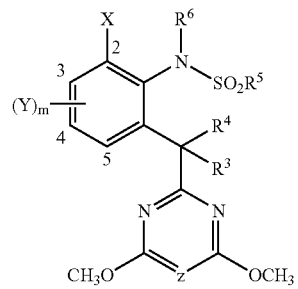

| | X | (Y)$_m$ | R$^3$ | R$^4$ | R$^5$ | R$^6$ | Z |
|---|---|---|---|---|---|---|---|
| 12-28 | Cl | 3-Cl | SCH$_3$ | H | CH$_3$ | H | CH |
| 12-29 | Cl | 3-Cl | SCH$_3$ | H | CH$_2$Cl | H | CH |
| 12-30 | Cl | 3-Cl | SCH$_3$ | H | CH$_2$CF$_3$ | H | CH |
| 12-31 | Cl | 3-Cl | SCH$_3$ | H | CH$_2$CN | H | CH |
| 12-32 | Cl | 3-Cl | SCH$_3$ | H | CF$_3$ | H | CH |
| 12-33 | Cl | 4-Cl | SCH$_3$ | H | CH$_3$ | H | CH |
| 12-34 | Cl | 4-Cl | SCH$_3$ | H | CH$_2$Cl | H | CH |
| 12-35 | Cl | 4-Cl | SCH$_3$ | H | CH$_2$CF$_3$ | H | CH |
| 12-36 | Cl | 4-Cl | SCH$_3$ | H | CH$_2$CN | H | CH |
| 12-37 | Cl | 4-Cl | SCH$_3$ | H | CF$_3$ | H | CH |
| 12-38 | F | H | H | H | CH$_2$CH=CH$_2$ | H | CH |
| 12-39 | F | H | H | H | propargyl | H | CH |
| 12-40 | F | H | H | H | cyclohexyl | H | CH |
| 12-41 | F | 3-F | H | H | CH$_3$ | H | CH |
| 12-42 | F | 3-F | H | H | CH$_2$Cl | H | CH |
| 12-43 | F | 3-F | H | H | CH$_2$CF$_3$ | H | CH |
| 12-44 | F | 3-F | H | H | CH$_2$CN | H | CH |
| 12-45 | F | 3-F | H | H | CF$_3$ | H | CH |
| 12-46 | F | 3-F | H | H | CH$_2$CO$_2$CH$_3$ | H | CH |
| 12-47 | F | 3-F | H | H | NHCO$_2$CH$_3$ | H | CH |
| 12-48 | F | 4-Cl | H | H | CH$_3$ | H | CH |
| 12-49 | F | 4-Cl | H | H | CH$_2$Cl | H | CH |
| 12-50 | F | 4-Cl | H | H | CH$_2$CF$_3$ | H | CH |
| 12-51 | F | 4-Cl | H | H | CH$_2$CN | H | CH |
| 12-52 | F | 4-Cl | H | H | CF$_3$ | H | CH |
| 12-53 | F | 5-Cl | H | H | CF$_3$ | H | CH |
| 12-54 | F | 5-Cl | H | H | CH$_2$CF$_3$ | H | CH |
| 12-55 | F | 3,4-F$_2$ | H | H | CH$_3$ | H | CH |
| 12-56 | F | 3,4-F$_2$ | H | H | CH$_2$Cl | H | CH |
| 12-57 | F | 3,4-F$_2$ | H | H | CH$_2$CF$_3$ | H | CH |
| 12-58 | F | 3,4-F$_2$ | H | H | CH$_2$CN | H | CH |
| 12-59 | F | 3,4-F$_2$ | H | H | CF$_3$ | H | CH |
| 12-60 | Cl | H | H | H | CH$_2$CH=CH$_2$ | H | CH |
| 12-61 | Cl | H | H | H | propargyl | H | CH |
| 12-62 | Cl | H | H | H | cyclohexyl | H | CH |
| 12-63 | Cl | 4-F | H | H | CH$_3$ | H | CH |
| 12-64 | Cl | 4-F | H | H | CH$_2$Cl | H | CH |
| 12-65 | Cl | 4-F | H | H | CH$_2$CF$_3$ | H | CH |
| 12-66 | Cl | 4-F | H | H | CH$_2$CN | H | CH |
| 12-67 | Cl | 4-F | H | H | CF$_3$ | H | CH |
| 12-68 | Cl | 4-CH$_3$ | H | H | CH$_3$ | H | CH |
| 12-69 | Cl | 4-CH$_3$ | H | H | CH$_2$Cl | H | CH |
| 12-70 | Cl | 4-CH$_3$ | H | H | CH$_2$CF$_3$ | H | CH |
| 12-71 | Cl | 4-CH$_3$ | H | H | CH$_2$CN | H | CH |
| 12-72 | Cl | 4-CH$_3$ | H | H | CF$_3$ | H | CH |
| 12-73 | Cl | 3-Cl | H | H | CH$_3$ | H | CH |
| 12-74 | Cl | 3-Cl | H | H | CH$_2$Cl | H | CH |
| 12-75 | Cl | 3-Cl | H | H | CH$_2$CF$_3$ | H | CH |
| 12-76 | Cl | 3-Cl | H | H | CH$_2$CN | H | CH |
| 12-77 | Cl | 3-Cl | H | H | CF$_3$ | H | CH |
| 12-78 | Cl | 4-Cl | H | H | CH$_3$ | H | CH |
| 12-79 | Cl | 4-Cl | H | H | CH$_2$Cl | H | CH |
| 12-80 | Cl | 4-Cl | H | H | CH$_2$CF$_3$ | H | CH |
| 12-81 | Cl | 4-Cl | H | H | CF$_3$ | H | CH |
| 12-82 | F | H | OH | H | CH$_2$CH=CH$_2$ | H | CH |
| 12-83 | F | H | OH | H | propargyl | H | CH |
| 12-84 | F | H | OH | H | cyclohexyl | H | CH |
| 12-85 | F | 3-F | OH | H | CH$_3$ | H | CH |
| 12-86 | F | 3-F | OH | H | CH$_2$Cl | H | CH |
| 12-87 | F | 3-F | OH | H | CH$_2$CF$_3$ | H | CH |
| 12-88 | F | 3-F | OH | H | CH$_2$CN | H | CH |
| 12-89 | F | 3-F | OH | H | CF$_3$ | H | CH |
| 12-90 | F | 3-F | OH | H | CH$_2$CO$_2$CH$_3$ | H | CH |

TABLE 12-continued

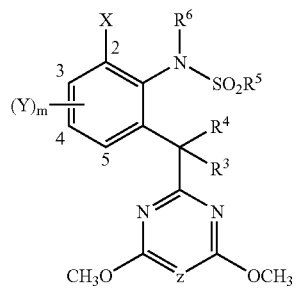

| | X | (Y)$_m$ | R$^3$ | R$^4$ | R$^5$ | R$^6$ | Z |
|---|---|---|---|---|---|---|---|
| 12-91 | F | 3-F | OH | H | NHCO$_2$CH$_3$ | H | CH |
| 12-92 | F | 4-Cl | OH | H | CH$_3$ | H | CH |
| 12-93 | F | 4-Cl | OH | H | CH$_2$Cl | H | CH |
| 12-94 | F | 4-Cl | OH | H | CH$_2$CF$_3$ | H | CH |
| 12-95 | F | 4-Cl | OH | H | CH$_2$CN | H | CH |
| 12-96 | F | 4-Cl | OH | H | CF$_3$ | H | CH |
| 12-97 | F | 3,4-F$_2$ | OH | H | CH$_3$ | H | CH |
| 12-98 | F | 3,4-F$_2$ | OH | H | CH$_2$Cl | H | CH |
| 12-99 | F | 3,4-F$_2$ | OH | H | CH$_2$CF$_3$ | H | CH |
| 12-100 | F | 3,4-F$_2$ | OH | H | CH$_2$CN | H | CH |
| 12-101 | F | 3,4-F$_2$ | OH | H | CF$_3$ | H | CH |
| 12-102 | Cl | H | OH | H | CH$_2$CH=CH$_2$ | H | CH |
| 12-103 | Cl | H | OH | H | propargyl | H | CH |
| 12-104 | Cl | H | OH | H | cyclohexyl | H | CH |
| 12-105 | Cl | 4-F | OH | H | CH$_3$ | H | CH |
| 12-106 | Cl | 4-F | OH | H | CH$_2$Cl | H | CH |
| 12-107 | Cl | 4-F | OH | H | CH$_2$CF$_3$ | H | CH |
| 12-108 | Cl | 4-F | OH | H | CH$_2$CN | H | CH |
| 12-109 | Cl | 4-F | OH | H | CF$_3$ | H | CH |
| 12-110 | Cl | 4-CH$_3$ | OH | H | CH$_3$ | H | CH |
| 12-111 | Cl | 4-CH$_3$ | OH | H | CH$_2$Cl | H | CH |
| 12-112 | Cl | 4-CH$_3$ | OH | H | CH$_2$CF$_3$ | H | CH |
| 12-113 | Cl | 4-CH$_3$ | OH | H | CH$_2$CN | H | CH |
| 12-114 | Cl | 4-CH$_3$ | OH | H | CF$_3$ | H | CH |
| 12-115 | Cl | 3-Cl | OH | H | CH$_3$ | H | CH |
| 12-116 | Cl | 3-Cl | OH | H | CH$_2$Cl | H | CH |
| 12-117 | Cl | 3-Cl | OH | H | CH$_2$CF$_3$ | H | CH |
| 12-118 | Cl | 3-Cl | OH | H | CH$_2$CN | H | CH |
| 12-119 | Cl | 3-Cl | OH | H | CF$_3$ | H | CH |
| 12-120 | Cl | 4-Cl | OH | H | CH$_3$ | H | CH |
| 12-121 | Cl | 4-Cl | OH | H | CH$_2$Cl | H | CH |
| 12-122 | Cl | 4-Cl | OH | H | CH$_2$CF$_3$ | H | CH |
| 12-123 | Cl | 4-Cl | OH | H | CH$_2$CN | H | CH |
| 12-124 | Cl | 4-Cl | OH | H | CF$_3$ | H | CH |
| 12-125 | Cl | H | CH$_3$ | H | CF$_3$ | H | CH |
| 12-126 | I | H | OH | H | CF$_3$ | H | CH |
| 12-127 | F | H | Cl | H | CF$_3$ | H | CH |
| 12-128 | CF$_3$ | H | OH | H | CF$_3$ | H | CH |
| 12-129 | F | 4-CH$_3$ | H | H | CH$_2$CF$_3$ | H | CH |
| 12-130 | Cl | 4-CF$_3$ | H | H | CH$_2$CF$_3$ | H | CH |
| 12-131 | F | 4-CH$_3$ | OH | H | CH$_2$CF$_3$ | H | CH |
| 12-132 | H | 4-CH$_3$ | H | H | CH$_2$CF$_3$ | H | CH |
| 12-133 | F | 3-F-4-CF$_3$ | H | H | CH$_2$CF$_3$ | H | CH |
| 12-134 | CL | 3-Cl | H | H | CH$_2$CF$_3$ | H | CH |
| 12-135 | F | 5-F | H | H | CH$_2$CF$_3$ | H | CH |
| 12-136 | F | H | H | H | CHCl$_2$ | H | CH |
| 12-137 | CH$_3$ | 3-F | OH | H | CH$_2$CF$_3$ | H | CH |

TABLE 13

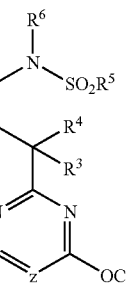

| | X | (Y)$_m$ | R$^1$ | R$^2$ | R$^5$ | Z |
|---|---|---|---|---|---|---|
| 13-1 | F | H | CH$_3$ | CH$_3$ | CH$_2$CF$_3$ | CH |
| 13-2 | Cl | H | CH$_3$ | CH$_3$ | CF$_3$ | CH |
| 13-3 | H | 4-Cl | OCH$_3$ | OCH$_3$ | CF$_3$ | CH |
| 13-4 | H | H | OCH$_3$ | OCH$_3$ | CH$_3$ | CH |
| 13-5 | H | H | OCH$_3$ | OCH$_3$ | CH$_2$CF$_3$ | CH |
| 13-6 | H | H | OCH$_3$ | OCH$_3$ | CH$_2$CF$_3$ | CH |
| 13-7 | CH$_3$ | 3-F | OCH$_3$ | OCH$_3$ | CF$_3$ | CH |
| 13-8 | CH$_3$ | 3-F | OCH$_3$ | OCH$_3$ | CH$_2$CF$_3$ | CH |
| 13-9 | CH$_3$ | 3-CH$_3$ | OCH$_3$ | OCH$_3$ | CH$_2$CF$_3$ | CH |

TABLE 14

| | X | (Y)$_m$ | R$^5$ | R$^6$ | Z |
|---|---|---|---|---|---|
| 14-1 | H | H | CH$_2$CN | H | CH |
| 14-2 | H | H | CF$_3$ | H | CH |
| 14-3 | H | 4-Cl | CH$_2$CN | H | CH |
| 14-4 | H | 4-F | CH$_3$$_{CN}$ | H | CH |
| 14-5 | H | 4-F | CF$_3$ | H | CH |
| 14-6 | H | 4-Br | CF$_3$ | H | CH |
| 14-7 | F | H | CF$_3$ | H | CH |
| 14-8 | F | H | CH$_2$Cl | H | CH |
| 14-9 | F | H | CH$_2$Br | H | CH |
| 14-10 | F | H | CH$_2$CF$_3$ | H | CH |
| 14-11 | F | H | CH$_2$CN | H | CH |
| 14-12 | F | 4-F | CH$_3$ | H | CH |
| 14-13 | F | 4-F | CF$_3$ | H | CH |
| 14-14 | F | 4-F | CH$_2$Cl | H | CH |
| 14-15 | F | 4-F | CH$_2$CN | H | CH |
| 14-16 | F | 4-CH$_3$ | CH$_3$$_{CN}$ | H | CH |
| 14-17 | F | 4-OCH$_3$ | CH$_2$CN | H | CH |
| 14-18 | F | 4-OC$_2$H$_5$ | CH$_2$CN | H | CH |
| 14-19 | Cl | H | CH$_2$CN | H | CH |
| 14-20 | Cl | H | CF$_3$ | H | CH |
| 14-21 | Cl | H | CH$_2$Cl | H | CH |
| 14-22 | Cl | H | CH$_2$CF$_3$ | H | CH |
| 14-23 | Cl | H | CH$_2$Cl | H | CH |
| 14-24 | Cl | 4-Cl | CH$_2$CN | H | CH |
| 14-25 | OCH$_3$ | 4-F | CH$_2$CN | H | CH |
| 14-26 | H | H | CF$_3$ | H | N |
| 14-27 | H | H | CH$_2$CN | H | N |
| 14-28 | F | H | CH$_3$CN | H | N |
| 14-29 | F | H | CF$_3$ | H | N |
| 14-30 | Cl | H | CF$_3$ | H | N |
| 14-31 | Cl | H | CH$_2$CN | H | N |
| 14-32 | Cl | 4-Cl | CH$_2$CN | H | N |
| 14-33 | F | H | CHF$_2$ | H | CH |

TABLE 14-continued

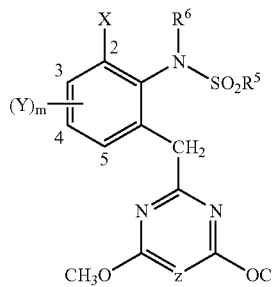

| | X | (Y)$_m$ | R$^5$ | R$^6$ | Z |
|---|---|---|---|---|---|
| 14-34 | F | H | CHF$_2$ | H | N |
| 14-35 | Cl | H | CHF$_2$ | H | CH |
| 14-36 | Cl | H | CHF$_2$ | H | N |
| 14-37 | CH$_3$ | H | CHF$_2$ | H | CH |
| 14-38 | CH$_2$OCH$_3$ | H | CHF$_2$ | H | CH |
| 14-39 | CH$_3$ | H | CHF$_2$ | CH$_2$CH=CH$_2$ | CH |
| 14-40 | CH$_2$OCH$_3$ | 3-F | CHF$_2$ | H | CH |

TABLE 15

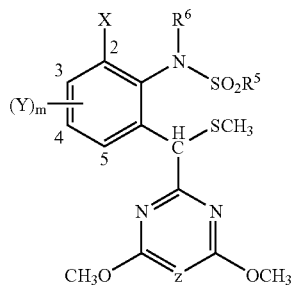

| | X | (Y)$_m$ | R$^5$ | R$^6$ | Z |
|---|---|---|---|---|---|
| 15-1 | H | H | CH$_3$ | H | CH |
| 15-2 | F | H | CH$_3$ | H | CH |
| 15-3 | Cl | H | CH$_3$ | H | CH |
| 15-4 | F | 4-F | CH$_3$ | H | CH |
| 15-5 | H | H | CH$_2$Cl | H | CH |
| 15-6 | F | H | CH$_2$Cl | H | CH |
| 15-7 | Cl | H | CH$_2$Cl | H | CH |
| 15-8 | F | 4-F | CH$_2$Cl | H | CH |
| 15-9 | H | H | CH$_2$CF$_3$ | H | CH |
| 15-10 | F | H | CH$_2$CF$_3$ | H | CH |
| 15-11 | Cl | H | CH$_2$CF$_3$ | H | CH |
| 15-12 | H | H | CH$_2$CN | H | CH |
| 15-13 | F | H | CH$_2$CN | H | CH |
| 15-14 | Cl | H | CH$_2$CN | H | CH |
| 15-15 | F | 4-F | CH$_2$CN | H | CH |
| 15-16 | H | H | CH$_2$CO$_2$CH$_3$ | H | CH |
| 15-17 | F | H | CH$_2$CO$_2$CH$_3$ | H | CH |
| 15-18 | Cl | H | CH$_2$CO$_2$CH$_3$ | H | CH |
| 15-19 | F | 4-F | CH$_2$CO$_2$CH$_3$ | H | CH |
| 15-20 | H | H | CF$_3$ | H | CH |
| 15-21 | F | H | CF$_3$ | H | CH |
| 15-22 | Cl | H | CF$_3$ | H | CH |
| 15-23 | F | 4-F | CF$_3$ | H | CH |
| 15-24 | H | H | CH$_2$Ph | H | CH |
| 15-25 | F | H | CH$_2$Ph | H | CH |
| 15-26 | Cl | H | CH$_2$Ph | H | CH |
| 15-27 | H | H | NHCO$_2$CH$_3$ | H | CH |
| 15-28 | F | H | NHCO$_2$CH$_3$ | H | CH |
| 15-29 | Cl | H | NHCO$_2$CH$_3$ | H | CH |
| 15-30 | H | H | CH$_3$ | H | N |
| 15-31 | F | H | CH$_3$ | H | N |
| 15-32 | Cl | H | CH$_3$ | H | N |
| 15-33 | H | H | CH$_2$Cl | H | N |
| 15-34 | F | H | CH$_2$Cl | H | N |
| 15-35 | Cl | H | CH$_2$Cl | H | N |

TABLE 15-continued

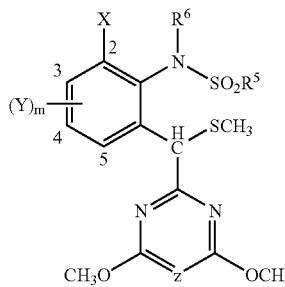

| | X | (Y)$_m$ | R$^5$ | R$^6$ | Z |
|---|---|---|---|---|---|
| 15-36 | H | H | CH$_2$CF$_3$ | H | N |
| 15-37 | F | H | CH$_2$CF$_3$ | H | N |
| 15-38 | Cl | H | CH$_2$CF$_3$ | H | N |
| 15-39 | H | H | CH$_2$CN | H | N |
| 15-40 | F | H | CH$_2$CN | H | N |
| 15-41 | Cl | H | CH$_2$CN | H | N |
| 15-42 | H | H | CH$_2$CO$_2$CH$_3$ | H | N |
| 15-43 | F | H | CH$_2$CO$_2$CH$_3$ | H | N |
| 15-44 | Cl | H | CH$_2$CO$_2$CH$_3$ | H | N |
| 15-45 | H | H | CF$_3$ | H | N |
| 15-46 | F | H | CF$_3$ | H | N |
| 15-47 | Cl | H | CF$_3$ | H | N |
| 15-48 | F | 4-F | CF$_3$ | H | N |
| 15-49 | C$_2$H$_5$ | H | CHF$_2$ | H | CH |
| 15-50 | CH$_2$OCH$_3$ | H | CHF$_2$ | H | CH |

TABLE 16

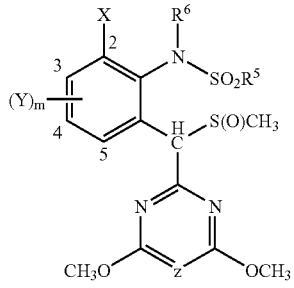

| | X | (Y)$_m$ | R$^5$ | R$^6$ | Z |
|---|---|---|---|---|---|
| 16-1 | H | H | CH$_3$ | H | CH |
| 16-2 | F | H | CH$_3$ | H | CH |
| 16-3 | Cl | H | CH$_3$ | H | CH |
| 16-4 | F | 4-F | CH$_3$ | H | CH |
| 16-5 | H | H | CH$_2$Cl | H | CH |
| 16-6 | F | H | CH$_2$Cl | H | CH |
| 16-7 | Cl | H | CH$_2$Cl | H | CH |
| 16-8 | F | 4-F | CH$_2$Cl | H | CH |
| 16-9 | H | H | CH$_2$CF$_3$ | H | CH |
| 16-10 | F | H | CH$_2$CF$_3$ | H | CH |
| 16-11 | Cl | H | CH$_2$CF$_3$ | H | CH |
| 16-12 | H | H | CH$_2$CN | H | CH |
| 16-13 | F | H | CH$_2$CN | H | CH |
| 16-14 | Cl | H | CH$_2$CN | H | CH |
| 16-15 | H | H | CH$_2$CO$_2$CH$_3$ | H | CH |
| 16-16 | F | H | CH$_2$CO$_2$CH$_3$ | H | CH |
| 16-17 | Cl | H | CH$_2$CO$_2$CH$_3$ | H | CH |
| 16-18 | H | H | CF$_3$ | H | CH |
| 16-19 | F | H | CF$_3$ | H | CH |
| 16-20 | Cl | H | CF$_3$ | H | CH |
| 16-21 | F | 4-F | CF$_3$ | H | CH |
| 16-22 | H | H | CH$_2$Ph | H | CH |
| 16-23 | F | H | CH$_2$Ph | H | CH |
| 16-24 | Cl | H | CH$_2$Ph | H | CH |
| 16-25 | H | H | NHCO$_2$CH$_3$ | H | CH |
| 16-26 | F | H | NHCO$_2$CH$_3$ | H | CH |
| 16-27 | Cl | H | NHCO$_2$CH$_3$ | H | CH |

TABLE 16-continued

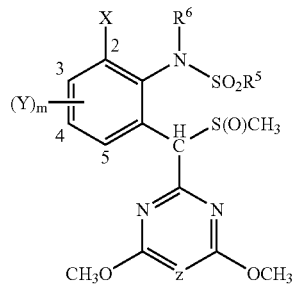

| | X | (Y)$_m$ | R$^5$ | R$^6$ | Z |
|---|---|---|---|---|---|
| 16-28 | CH$_2$OCH$_3$ | H | CHF$_2$ | H | CH |

TABLE 17

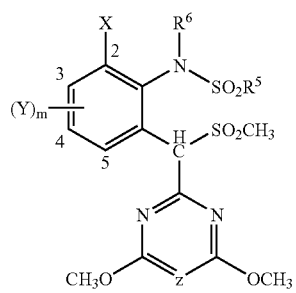

| | X | (Y)$_m$ | R$^5$ | R$^6$ | Z |
|---|---|---|---|---|---|
| 17-1 | H | H | CH$_3$ | H | CH |
| 17-2 | F | H | CH$_3$ | H | CH |
| 17-3 | Cl | H | CH$_3$ | H | CH |
| 17-4 | F | 4-F | CH$_3$ | H | CH |
| 17-5 | H | H | CH$_2$Cl | H | CH |
| 17-6 | F | H | CH$_2$Cl | H | CH |
| 17-7 | Cl | H | CH$_2$Cl | H | CH |
| 17-8 | F | 4-F | CH$_2$Cl | H | CH |
| 17-9 | H | H | CH$_2$CF$_3$ | H | CH |
| 17-10 | F | H | CH$_2$CF$_3$ | H | CH |
| 17-11 | Cl | H | CH$_2$CF$_3$ | H | CH |
| 17-12 | H | H | CH$_2$CN | H | CH |
| 17-13 | F | H | CH$_2$CN | H | CH |
| 17-14 | Cl | H | CH$_2$CN | H | CH |
| 17-15 | H | H | CH$_2$CO$_2$CH$_3$ | H | CH |
| 17-16 | F | H | CH$_2$CO$_2$CH$_3$ | H | CH |
| 17-17 | Cl | H | CH$_2$CO$_2$CH$_3$ | H | CH |
| 17-18 | H | H | CF$_3$ | H | CH |
| 17-19 | F | H | CF$_3$ | H | CH |
| 17-20 | Cl | H | CF$_3$ | H | CH |
| 17-21 | F | 4-F | CF$_3$ | H | CH |
| 17-22 | H | H | CH$_2$Ph | H | CH |
| 17-23 | F | H | CH$_2$Ph | H | CH |
| 17-24 | Cl | H | CH$_2$Ph | H | CH |
| 17-25 | H | H | NHCO$_2$CH$_3$ | H | CH |
| 17-26 | F | H | NHCO$_2$CH$_3$ | H | CH |
| 17-27 | Cl | H | NHCO$_2$CH$_3$ | H | CH |

TABLE 18

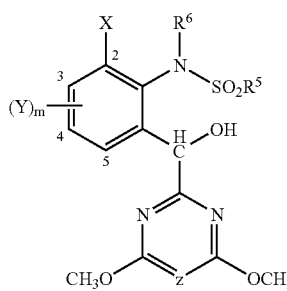

| | X | (Y)$_m$ | R$^5$ | R$^6$ | Z |
|---|---|---|---|---|---|
| 18-1 | H | H | CH$_3$ | H | CH |
| 18-2 | F | H | CH$_3$ | H | CH |
| 18-3 | Cl | H | CH$_3$ | H | CH |
| 18-4 | F | 4-F | CH$_3$ | H | CH |
| 18-5 | H | H | CH$_2$Cl | H | CH |
| 18-6 | F | H | CH$_2$Cl | H | CH |
| 18-7 | Cl | H | CH$_2$Cl | H | CH |
| 18-8 | F | 4-F | CH$_2$Cl | H | CH |
| 18-9 | H | H | CH$_2$CF$_3$ | H | CH |
| 18-10 | F | H | CH$_2$CF$_3$ | H | CH |
| 18-11 | Cl | H | CH$_2$CF$_3$ | H | CH |
| 18-12 | H | H | CH$_2$CN | H | CH |
| 18-13 | F | H | CH$_2$CN | H | CH |
| 18-14 | Cl | H | CH$_2$CN | H | CH |
| 18-15 | F | 4-F | CH$_2$CN | H | CH |
| 18-16 | H | H | CH$_2$CO$_2$CH$_3$ | H | CH |
| 18-17 | F | H | CH$_2$CO$_2$CH$_3$ | H | CH |
| 18-18 | Cl | H | CH$_2$CO$_2$CH$_3$ | H | CH |
| 18-19 | F | 4-F | CH$_2$CO$_2$CH$_3$ | H | CH |
| 18-20 | H | H | CF$_3$ | H | CH |
| 18-21 | F | H | CF$_3$ | H | CH |
| 18-22 | Cl | H | CF$_3$ | H | CH |
| 18-23 | F | 4-F | CF$_3$ | H | CH |
| 18-24 | H | H | CHF$_2$ | H | CH |
| 18-25 | F | H | CHF$_2$ | H | CH |
| 18-26 | Cl | H | CHF$_2$ | H | CH |
| 18-27 | H | H | CH$_2$Ph | H | CH |
| 18-28 | F | H | CH$_2$Ph | H | CH |
| 18-29 | Cl | H | CH$_2$Ph | H | CH |
| 18-30 | H | H | NHCO$_2$CH$_3$ | H | CH |
| 18-31 | F | H | NHCO$_2$CH$_3$ | H | CH |
| 18-32 | Cl | H | NHCO$_2$CH$_3$ | H | CH |
| 18-33 | H | H | CH$_3$ | H | N |
| 18-34 | F | H | CH$_3$ | H | N |
| 18-35 | Cl | H | CH$_3$ | H | N |
| 18-36 | H | H | CH$_2$Cl | H | N |
| 18-37 | F | H | CH$_2$Cl | H | N |
| 18-38 | Cl | H | CH$_2$Cl | H | N |
| 18-39 | H | H | CH$_2$CF$_3$ | H | N |
| 18-40 | F | H | CH$_2$CF$_3$ | H | N |
| 18-41 | Cl | H | CH$_2$CF$_3$ | H | N |
| 18-42 | H | H | CH$_2$CN | H | N |
| 18-43 | F | H | CH$_2$CN | H | N |
| 18-44 | Cl | H | CH$_2$CN | H | N |
| 18-45 | H | H | CH$_2$CO$_2$CH$_3$ | H | N |
| 18-46 | F | H | CH$_2$CO$_2$CH$_3$ | H | N |
| 18-47 | Cl | H | CH$_2$CO$_2$CH$_3$ | H | N |
| 18-48 | H | H | CF$_3$ | H | N |
| 18-49 | F | H | CF$_3$ | H | N |
| 18-50 | Cl | H | CF$_3$ | H | N |
| 18-51 | F | H | CHF$_2$ | H | N |
| 18-52 | Cl | H | CHF$_2$ | H | N |
| 18-53 | CH$_3$ | H | CHF$_2$ | H | N |

TABLE 19

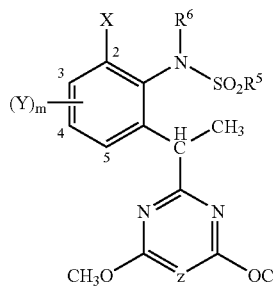

| | X | (Y)$_m$ | R$^5$ | R$^6$ | Z |
|---|---|---|---|---|---|
| 19-1 | H | H | CF$_3$ | H | CH |
| 19-2 | Cl | H | CH$_2$CN | H | CH |

TABLE 20

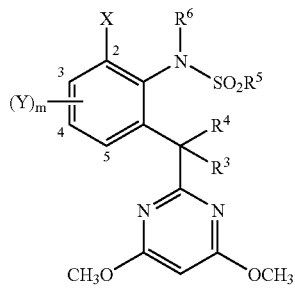

| | X | (Y)$_m$ | R$^3$ | R$^4$ | R$^5$ | R$^6$ |
|---|---|---|---|---|---|---|
| 20-1 | F | H | NHCH$_3$ | H | CH$_2$Cl | H |
| 20-2 | F | H | NHCH$_3$ | H | CH$_2$CN | H |
| 20-3 | F | H | NHCH$_3$ | H | CHF$_2$ | H |
| 20-4 | F | H | NHCH$_3$ | H | CF$_3$ | H |
| 20-5 | Cl | H | NHCH$_3$ | H | CH$_2$Cl | H |
| 20-6 | Cl | H | NHCH$_3$ | H | CH$_2$CN | H |
| 20-7 | Cl | H | NHCH$_3$ | H | CHF$_2$ | H |
| 20-8 | Cl | H | NHCH$_3$ | H | CF$_3$ | H |
| 20-9 | F | H | N(CH$_3$)$_2$ | H | CH$_2$Cl | H |
| 20-10 | F | H | N(CH$_3$)$_2$ | H | CH$_2$CN | H |
| 20-11 | F | H | N(CH$_3$)$_2$ | H | CHF$_2$ | H |
| 20-12 | F | H | N(CH$_3$)$_2$ | H | CF$_3$ | H |
| 20-13 | Cl | H | N(CH$_3$)$_2$ | H | CH$_2$Cl | H |
| 20-14 | Cl | H | N(CH$_3$)$_2$ | H | CH$_2$CN | H |
| 20-15 | Cl | H | N(CH$_3$)$_2$ | H | CHF$_2$ | H |
| 20-16 | Cl | H | N(CH$_3$)$_2$ | H | CF$_3$ | H |

TABLE 21

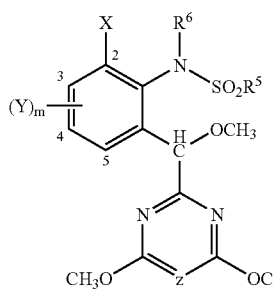

| | X | (Y)$_m$ | R$^5$ | R$^6$ | Z |
|---|---|---|---|---|---|
| 21-1 | H | H | CH$_3$ | H | CH |
| 21-2 | F | H | CH$_3$ | H | CH |
| 21-3 | Cl | H | CH$_3$ | H | CH |
| 21-4 | H | H | CH$_2$Cl | H | CH |
| 21-5 | F | H | CH$_2$Cl | H | CH |
| 21-6 | Cl | H | CH$_2$Cl | H | CH |
| 21-7 | H | H | CH$_2$CF$_3$ | H | CH |
| 21-8 | F | H | CH$_2$CF$_3$ | H | CH |
| 21-9 | Cl | H | CH$_2$CF$_3$ | H | CH |
| 21-10 | H | H | CH$_2$CN | H | CH |
| 21-11 | F | H | CH$_2$CN | H | CH |
| 21-12 | Cl | H | CH$_2$CN | H | CH |
| 21-13 | H | H | CH$_2$CO$_2$CH$_3$ | H | CH |
| 21-14 | F | H | CH$_2$CO$_2$CH$_3$ | H | CH |
| 21-15 | Cl | H | CH$_2$CO$_2$CH$_3$ | H | CH |
| 21-16 | H | H | CF$_3$ | H | CH |
| 21-17 | F | H | CF$_3$ | H | CH |
| 21-18 | Cl | H | CF$_3$ | H | CH |

TABLE 22

| Compound No. | Physical & Chemical Properties (mp (° C.), n$^D_{20}$ or $^1$H-NMR(300MHz, CDCl$_3$) δ?) |
|---|---|
| 9-25 | 3.97(6H, s), 6.20(1H, s), 6.51(1H, t), 7.29-7.34(1H, m), 7.39-7.46(1H, m), 7.55-7.58(1H, m), 11.14(1H, br) |
| 9-26 | 3.93(6H, s), 6.19(1H, s), 6.34(1H, t), 7.37-7.43(1H, m), 7.63-7.69(2H, m) |
| 9-48 | 4.10(6H, s), 6.48(1H, t), 7.34(1H), 7.45(1H), 7.55(1H), 9.08(1H, s) |
| 12-127 | 3.99(6H, s), 6.00(1H, s), 6.13(1H, s), 7.16-7.33(2H, m), 7.42-7.44(1H, m) |
| 12-131 | 141-145 |
| 12-136 | 3.98(6H, s), 4.27(2H, s), 5.92(1H, s), 6.73(1H, d), 7.04-7.23(2H, m) |
| 12-137 | 134-136 |
| 13-8 | 143-148 |
| 14-8 | 3.98(6H, s), 4.25(2H, s), 4.83(2H, s), 5.92(1H, s), 7.03-7.22(2H, m), 10.52(1H, br) |
| 14-33 | 3.97(6H, s), 4.26(2H, s), 5.94(1H, s), 6.59(1H, t), 7.05-7.13(1H, m), 7.16-7.23(2H, m), 11.14(1H, br) |
| 14-34 | 4.05(6H, s), 4.22(2H, s), 6.56(1H, t), 7.07-7.27(3H), 10.16(1H, s) |
| 14-35 | 3.94(6H, s), 4.30(2H, s), 5.92(1H, s), 6.74(1H, t), 7.18-7.21(1H, m), 7.33-7.38(2H, m), 11.09(1H, br) |
| 14-36 | 4.02(6H, s), 4.34(2H, s), 6.68(1H, t), 7.22(1H), 7.32(1H), 7.41(1H), 9.98(1H, br) |
| 14-37 | 2.48(3H, s), 3.95(6H, s), 4.26(2H, s), 5.90(1H, s), 6.37(1H, t), 7.15-7.26(4H), 10.97(1H, s). |
| 14-40 | 3.33(3H, s), 3.94(6H, s), 4.27(2H, s), 4.68(2H, s), 5.92(1H, s), 6.75(1H, t, J=54Hz), 7.02(1H, dd, J=9.0, 9.0Hz), 7.37(1H, dd, J=9.0, 6.0Hz). |

TABLE 22-continued

| Compound No. | Physical & Chemical Properties (mp (° C.), $n^D{}_{20}$ or $^1$H-NMR(300MHz, CDCl$_3$) δ?) |
|---|---|
| 18-20 | 4.00(6H, s), 5.97(1H, s), 6.00(1H, s), 7.28-7.35(2H, m), 7.57-7.60(1H, m), 7.71-7.74(1H, m), 11.28(1H, br) |
| 18-26 | 3.99(6H, s), 4.99(1H, br), 5.99(1H, s), 6.24(1H, s), 6.76(1H, t), 7.27-7.30(1H, m), 7.39-7.42(1H, m), 7.64-7.67(1H, m), 10.62(1H, br) |
| 18-53 | 2.49(3H, s) 3.98(6H, s) 4.97(1H, d) 5.40(1H, s) 5.97(1H, s) 6.42(1H, t) 7.20-7.27(2H) 7.54(1H) 10.33(1H, s) |

TEST EXAMPLE 1

Test for Effect of Foliage Application Against *Pyricularia oryzae*

Preparation of Testing Compound
Active compound: 5 parts by weight
Organic solvent: Acetone 142.5 parts by weight
Emulsifier: Polyoxyethylene alkyl phenyl ether 7.5 parts by weight The above-mentioned active compound, acetone and emulsifier were mixed, diluted to a prescribed concentration with water and used for test.

Test Method

Paddy rice (variety: KOSIHIKARI) was cultivated in a plastic pot of 4 cm diameter. At its 1.5 to 2 leaf stage a previously prepared diluted solution of an active compound of the prescribed concentration was sprayed in an amount of 6 ml per 3 pots. One day after spraying, a suspension of spores of artificially cultured *Pyricularia oryzae* was inoculated by spraying (once) and infected in keeping at 25° C. and 100% relative humidity. Seven days after the inoculation, the contraction rate per pot was classified and evaluated to obtain the controlling value (%). Phytotoxicity was also studied at the same time. This test is an average of the results of 1 section 3 pots.

Evaluation of contraction rate and calculation method of controlling value are as follows:

| Contraction rate | Lesion area ratio (%) |
|---|---|
| 0 | 0 |
| 0.5 | less than 2 |
| 1 | 2-less than 5 |
| 2 | 5-less than 10 |
| 3 | 10-less than 20 |
| 4 | 20-less than 40 |
| 5 | more than 40 |

Controlling value (%)=(1−{contraction rate of treated section÷contraction rate of untreated section})×100

Test Results

Compounds of the compound numbers 2-31, 2-32, 2-61, 2-62, 2-125, 2-190, 2-191, 2-193, 3-22, 4-130, 4-184, 5-2, 12-127, 12-131, 12-137, 14-37, 18-2, 18-6, 18-10, 18-21, 18-24 and 18-53 as specific examples showed controlling values of more than 80% at the active component concentration (500 ppm). No phytotoxicity was observed.

BIOLOGICAL TEST EXAMPLE 2

Test for Effect of Foliage Application Against *Botrytis cinerea*

Test Method

Cucumber (variety: SAGAMI HANPAKU) was cultivated in a plastic pot of 4 cm diameter. A diluted solution of an active compound of the prescribed concentration, prepared in a similar manner as in the above-mentioned Test Example 1, was sprayed to seedlings reached to cotyledon in an amount of 6 ml per 2 pots. One day after the spraying, an inoculant, prepared by mixing a suspension of artificially cultured spores of *Botrytis cinerea* and agar gel (2×10$^4$ spores/ml gel), was placed on cotyledons to inoculate and infected in a moisture box kept at 20° C. Four days after the inoculation, the contraction rate per cotyledon was classified and evaluated according to the following standard to obtain the controlling value (%). Phytotoxicity was also studied at the same time. This test is an average of the results of 2 sections 4 cotyledons.

Evaluation of contraction rate and calculation method of controlling value are as follows:

| Contraction rate | Lesion area ratio (%) |
|---|---|
| 0 | 0 |
| 0.5 | less than 2 |
| 1 | 2-less than 5 |
| 2 | 5-less than 10 |
| 3 | 10-less than 20 |
| 4 | 20-less than 40 |
| 5 | more than 40 |

Controlling value (%)=(1−{contraction rate of treated section÷contraction rate of untreated section})×100

Test Results

Compounds of the compound numbers 1-14, 2-1, 2-18, 2-31, 2-110, 2-138, 2-191, 2-192, 3-31, 4-107, 4-130, 4-186, 4-187, 9-25, 9-26, 9-48, 12-136, 13-8, 14-2, 14-8, 14-20, 14-22, 14-35, 14-37, 14-40, 18-6, 18-10, 18-20, 18-24, 18-25, 18-26 and 18-51 as specific examples showed controlling values of more than 80% at the active component concentration (500 ppm). No phytotoxicity was observed.

FORMULATION EXAMPLE 1

Granule

To a mixture of the compound of the present invention No. 14-33 (10 parts), bentonite (montmorillonite) (30 parts), talc (58 parts) and ligninsulfonate salt (2 parts), water (25 parts) is added, well kneaded, made into granules of 10-40 mesh by an extrusion granulator and dried at 40-50° C. to obtain granules.

FORMULATION EXAMPLE 2

Granules

Clay mineral particles having particle size distribution in the range of 0.2-2 mm (95 parts) are put in a rotary mixer. While rotating it, the compound of the present invention No. 18-24 (5 parts) are sprayed together with a liquid diluent, wetted uniformly and dried at 40-50° C. to obtain granules.

FORMULATION EXAMPLE 3

Emulsifiable Concentrate

The compound of the present invention No. 18-6 (30 parts), xylene (55 parts), polyoxyethylene alkyl phenyl ether (8 parts) and calcium alkylbenzenesulfonate (7 parts) are mixed and stirred to obtain an emulsifiable concentrate.

FORMULATION EXAMPLE 4

Wettable Powder

The compound of the present invention No. 14-35 (15 parts), a mixture of white carbon (hydrous amorphous silicon oxide fine powder) and powder clay (1:5) (80 parts), sodium alkylbenzenesulfonate (2 parts) and sodium alkylnaphthalenesulfonate-formalin-condensate (3 parts) are crushed and mixed to make a wettable powder.

FORMULATION EXAMPLE 5

Water Dispersible Granule

The compound of the present invention No. 18-51 (20 parts), sodium ligninsulfonate (30 parts), bentonite (15 parts) and calcined diatomaceous earth powder (35 parts) are well mixed, added with water, extruded with 0.3 mm screen and dried to obtain water dispersible granules.

The invention claimed is:

1. Sulfonanilides represented by the formula

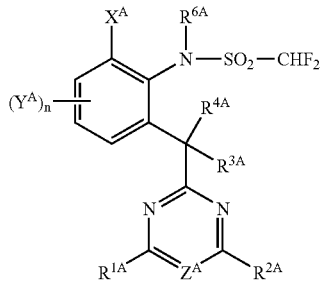

(IA)

wherein $X^A$ represents hydrogen, alkyl, halogen, alkoxycarbonyl, acyl, dialkylaminocarbonyl, alkoxy, alkylsulfonyl, alkylsulfonyloxy, dialkylamino, haloalkoxy, haloalkylthio, haloalkylsulfinyl, haloalkylsulfonyl, haloalkylsulfonyloxy, formyl, carboxy, cyano, nitro or phenoxy, $Y^A$ represents halogen, alkoxyalkyl, alkoxycarbonyl, acyl, alkoxy, alkylsulfonyl, haloalkoxy, haloalkylthio, haloalkylsulfinyl, haloalkylsulfonyl, dialkylamino, cyano, nitro, or alkyl that may be optionally substituted by one or more halogens and 2 or 3 $Y^A$'s may be identical or different each other in case that n is 2 or 3, $Z^A$ represents N, n represents an integer of 0 to 3, $R^{1A}$ and $R^{2A}$ each independently represents hydrogen, halogen, cycloalkyl, alkoxy, haloalkoxy, alkylthio, or alkyl that may be optionally substituted by one or more halogens, $R^{3A}$ and $R^{4A}$ each independently represents hydrogen, halogen, alkyl, alkoxy, alkylthio or alkylsulfonyl, or $R^{3A}$ represents hydroxy and $R^{4A}$ represents hydrogen or alkyl, or $R^{3A}$ and $R^{4A}$ together may form C=O with the carbon atom to which they are bonded, $R^{6A}$ represents hydrogen, alkoxyalkyl, alkoxycarbonyl, acyl, group —$SO_2R^{5A}$, or alkyl that may be optionally substituted by one or more halogens, $R^{5A}$ represents alkyl that may be optionally substituted by one or more halogens, and $R^{7A}$ represents hydrogen or alkyl, with the exception of the following cases (T-1) or (T-3);

(T-1) the case in which $X^A$ represents alkyl, and n represents 0, (T-3) the case in which $X^A$ represents halogen, n represents 0, $Z^A$ represents N, $R^{1A}$ and $R^{2A}$ represent methoxy, $R^{3A}$ and $R^{4A}$ represent hydrogen, $R^{3A}$ represents hydroxyl and $R^{4A}$ represents hydrogen, or $R^{3A}$ and $R^{4A}$ together form C=O with the carbon atom to which they are bonded, and $R^{6A}$ represents hydrogen.

2. Compounds set forth in claim 1, wherein $X^A$ represents hydrogen, fluorine, chlorine, $C_{1-6}$alkyl, $C_{1-6}$alkoxy-carbonyl, $C_{1-6}$alkyl-carbonyl, $C_{3-7}$cycloalkyl-carbonyl, di($C_{1-6}$alkyl)aminocarbonyl, $C_{1-6}$alkoxy, $C_{1-6}$ alkylsulfonyl, $C_{1-6}$alkylsulfonyloxy, di($C_{1-6}$alkyl)amino, $C_{1-6}$haloalkoxy, $C_{1-6}$haloalkylthio, $C_{1-6}$haloalkylsulfinyl, $C_{1-6}$haloalkylsulfonyl, $C_{1-6}$haloalkylsulfonyloxy, formyl, carboxy, cyano, nitro or phenoxy, $Y^A$ represents fluorine, chlorine, $C_{1-6}$alkyl, where at least one hydrogen of which may be optionally halogen-substituted, $C_{1-6}$alkoxy-$C_{1-6}$alkyl, $C_{1-6}$alkoxy-carbonyl, $C_{1-6}$alkyl-carbonyl, $C_{1-6}$alkoxy, $C_{1-6}$alkylsulfonyl, $C_{1-6}$haloalkoxy, $C_{1-6}$haloalkylthio, $C_{1-6}$ haloalkylsulfinyl, $C_{1-6}$haloalkylsulfonyl, di($C_{1-6}$alkyl)amino, cyano or nitro, and 2 $Y^A$'s may be identical or different each other in case that n is 2, $Z^A$ represents N, n represents 0, 1 or 2, $R^{1A}$ and $R^{2A}$ each independently represents hydrogen, chlorine, $C_{1-6}$alkyl, where at least one hydrogen of which may be optionally halogen-substituted, $C_{3-7}$cycloalkyl, $C_{1-6}$ alkoxy, $C_{1-6}$haloalkoxy or $C_{1-6}$alkylthio, $R^{3A}$ and $R^{4A}$ each independently represents hydrogen, fluorine, chlorine, $C_{1-6}$alkyl, $C_{1-6}$ alkoxy, $C_{1-6}$alkylthio or $C_{1-6}$alkylsulfonyl, $R^{3A}$ represents hydroxy and $R^{4A}$ represents hydrogen or $C_{1-6}$alkyl, or $R^{3A}$ and $R^{4A}$ together may form C=O with the carbon atom to which they are bonded, $R^{6A}$ represents hydrogen, $C_{1-6}$alkyl, where at least one hydrogen of which may be optionally halogen-substituted, $C_{1-6}$alkoxy-$C_{1-6}$alkyl, $C_{1-6}$alkoxy-carbonyl, $C_{1-6}$alkyl-carbonyl, $C_{3-7}$cycloalkyl-carbonyl, or group —$SO_2R^{5A}$, $R^{5A}$ represents $C_{1-6}$alkyl, $C_{1-6}$haloalkyl or cyano-substituted $C_{1-6}$alkyl, and $R^{7A}$ represents hydrogen or $C_{1-6}$alkyl, with the exception of the following cases (T-1) or (T-3);

(T-1) the case in which $X^A$ represents alkyl, and n represents 0, (T-3) the case in which $X^A$ represents halogen, n represents 0, $Z^A$ represents N, $R^{1A}$ and $R^{2A}$ represent methoxy, $R^{3A}$ and $R^{4A}$ represent hydrogen, $R^{3A}$ represents hydroxyl and $R^{4A}$ represents hydrogen, or $R^{3A}$ and $R^{4A}$ together form C=O with the carbon atom to which they are bonded, and $R^{6A}$ represents hydrogen.

3. Compounds set forth in claim 1, wherein
$X^A$ represents hydrogen, fluorine, chlorine, $C_{1-4}$alkyl, $C_{1-4}$alkoxy-carbonyl, $C_{1-4}$alkyl-carbonyl, $C_{3-5}$cycloalkyl-carbonyl, di($C_{1-4}$alkyl)aminocarbonyl, $C_{1-4}$alkoxy, $C_{1-4}$ alkylsulfonyl, $C_{1-4}$alkylsulfonyloxy, di($C_{1-4}$alkyl)amino, $C_{1-4}$haloalkoxy, $C_{1-4}$haloalkylthio, $C_{1-4}$haloalkylsulfinyl, $C_{1-4}$haloalkylsulfonyl, $C_{1-4}$haloalkylsulfonyloxy, formyl, carboxy, cyano, nitro or phenoxy,
$Y^A$ represents fluorine, chlorine, $C_{1-4}$alkyl, where at least one hydrogen of which may be optionally halogen-substituted, $C_{1-4}$alkoxy-$C_{1-4}$alkyl, $C_{1-4}$alkoxy-carbonyl, $C_{1-4}$alkyl-carbonyl, $C_{1-4}$alkoxy, $C_{1-4}$alkylsulfonyl, $C_{1-4}$haloalkoxy, $C_{1-4}$haloalkylthio, $C_{1-4}$ haloalkylsulfinyl, $C_{1-4}$haloalkylsulfonyl, di($C_{1-4}$alkyl)amino, cyano or nitro, and 2 $Y^A$'s may be identical or different each other in case that n is 2,
$Z^A$ represents N,
n represents 0, 1 or 2,
$R^{1A}$ and $R^{2A}$ each independently represents hydrogen, chlorine, $C_{1-4}$alkyl, where at least one hydrogen of which may be optionally halogen-substituted, $C_{3-5}$cycloalkyl, $C_{1-4}$ alkoxy, $C_{1-4}$haloalkoxy or $C_{1-4}$alkylthio,
$R^{3A}$ and $R^{4A}$ each independently represents hydrogen, fluorine, chlorine, $C_{1-4}$alkyl, $C_{1-4}$ alkoxy, $C_{1-4}$alkylthio or $C_{1-4}$alkylsulfonyl,
$R^{3A}$ represents hydroxy and $R^{4A}$ represents hydrogen or $C_{1-4}$alkyl, or
$R^{3A}$ and $R^{4A}$ together may form C=O with the carbon atom to which they are bonded,
$R^{6A}$ represents hydrogen, $C_{1-4}$alkyl, where at least one hydrogen of which may be optionally halogen-substituted, $C_{1-4}$alkoxy-$C_{1-4}$alkyl, $C_{1-4}$alkoxy-carbonyl, $C_{1-4}$alkyl-carbonyl, $C_{3-5}$cycloalkyl-carbonyl, or group —$SO_2R^{5A}$,
$R^{5A}$ represents $C_{1-4}$alkyl, $C_{1-4}$haloalkyl or cyano-substituted $C_{1-4}$alkyl, and
$R^{7A}$ represents hydrogen or $C_{1-4}$alkyl,
with the exception of the following cases (T-1) or (T-3);
(T-1) the case in which $X^A$ represents alkyl, and n represents 0,
(T-3) the case in which $X^A$ represents halogen, n represents 0, $Z^A$ represents N, $R^{1A}$ and $R^{2A}$ represent methoxy, $R^{3A}$ and $R^{4A}$ represent hydrogen, $R^{3A}$ represents hydroxyl and $R^{4A}$ represents hydrogen, or $R^{3A}$ and $R^{4A}$ together form C=O with the carbon atom to which they are bonded, and $R^{6A}$ represents hydrogen.

4. The sulfonanilides of claim 1, wherein:
$X^A$ represents halogen,
$Z^A$ represents N,
n represents 0,
$R^{1A}$ and $R^{2A}$ each independently represent $C_1$-$C_6$-alkoxy,
$R^{3A}$ represents hydroxyl, $R^{4A}$ represents hydrogen, or
$R^{3A}$ and $R^{4A}$ together may form C=O, and
$R^{6A}$ represents $C_1$-$C_4$ alkyl.

5. The sulfonanilides of claim 4, wherein:
$X^A$ represents fluorine,
$R^{1A}$ and $R^{2A}$ each represent methoxy, and
$R^{6A}$ represents methyl.

6. The sulfonanilides of claim 1, wherein:
$X^A$ represents alkyl, halogen, alkoxycarbonyl, acyl, dialkylaminocarbonyl, alkoxy, alkylsulfonyl, alkylsulfonyloxy, dialkylamino, haloalkoxy, haloalkylthio, haloalkylsulfinyl, haloalkylsulfonyl, haloalkylsulfonyloxy, formyl, carboxy, cyano, nitro or phenoxy,
$Z^A$ represents N,
n represents 0,
$R^{1A}$ and $R^{2A}$ each independently represents hydrogen, halogen, cycloalkyl, alkoxy, haloalkoxy, alkylthio, or alkyl that may be optionally substituted by one or more halogens,
$R^{3A}$ and $R^{4A}$ each independently represents hydrogen, halogen, alkyl, alkoxy, alkylthio or alkylsulfonyl, or
$R^{3A}$ represents hydroxy and $R^{4A}$ represents hydrogen or alkyl, or
$R^{3A}$ and $R^{4A}$ together may form C=O with the carbon atom to which they are bonded,
$R^{6A}$ represents hydrogen or alkyl that may be optionally substituted by one or more halogens,
with the exception of the following cases (T-1) or (T-3);
(T-1) the case in which $X^A$ represents alkyl, and n represents 0,
(T-3) the case in which $X^A$ represents halogen, n represents 0, $Z^A$ represents N, $R^{1A}$ and $R^{2A}$ represent methoxy, $R^{3A}$ and $R^{4A}$ represent hydrogen, $R^{3A}$ represents hydroxy and $R^{4A}$ represents hydrogen, or $R^{3A}$ and $R^{4A}$ together form C=O with the carbon atom to which they are bonded, and $R^{6A}$ represents hydrogen.

7. The sulfonanilides of claim 6, wherein:
$X^A$ represents fluorine, chlorine, $C_{1-6}$-alkyl, $C_{1-6}$alkoxy-carbonyl, $C_{1-6}$alkyl-carbonyl, $C_{3-7}$cycloalkyl-carbonyl, di($C_{1-6}$alkyl)aminocarbonyl, $C_{1-6}$alkoxy, $C_{1-6}$alkylsulfonyl, $C_{1-6}$alkylsulfonyloxy, di($C_{1-6}$alkyl)amino, $C_{1-6}$haloalkoxy, $C_{1-6}$haloalkylthio, $C_{1-6}$haloalkylsulfinyl, $C_{1-6}$haloalkylsulfonyl, $C_{1-6}$haloalkylsulfonyloxy, formyl, carboxy, cyano, nitro or phenoxy,
$R^{1A}$ and $R^{2A}$ each independently represents hydrogen, chlorine, $C_{1-6}$alkyl, where at least one hydrogen of which may be optionally halogen-substituted, $C_{3-7}$cycloalkyl, $C_{1-6}$alkoxy, $C_{1-6}$haloalkoxy or $C_{1-6}$alkylthio,
$R^{3A}$ and $R^{4A}$ each independently represents hydrogen, fluorine, chlorine, $C_{1-6}$alkyl, $C_{1-6}$alkoxy, $C_{1-6}$alkylthio or $C_{1-6}$alkylsulfonyl,
$R^{3A}$ represents hydroxy and $R^{4A}$ represents hydrogen or $C_{1-6}$alkyl, or
$R^{3A}$ and $R^{4A}$ together may form C=O with the carbon atom to which they are bonded,
$R^{6A}$ represents hydrogen or $C_{1-6}$alkyl, where at least one hydrogen of which may be optionally halogen-substituted, $R^{5A}$ represents $C_{1-6}$alkyl, $C_{1-6}$haloalkyl or cyano-substituted $C_{1-6}$alkyl, and
with the exception of the following cases (T-1) or (T-3);
(T-1) the case in which $X^A$ represents $C_{1-6}$alkyl, and n represents 0,
(T-3) the case in which $X^A$ represents fluorine or chlorine, n represents 0, $Z^A$ represents N, $R^{1A}$ and $R^{2A}$ represent methoxy, $R^{3A}$ and $R^{4A}$ represent hydrogen, $R^{3A}$ represents hydroxy and $R^{4A}$ represents hydrogen, or $R^{3A}$ and $R^{4A}$ together form C=O with the carbon atom to which they are bonded, and $R^{6A}$ represents hydrogen.

8. The sulfonanilides of claim 7, wherein
$X^A$ represents hydrogen, fluorine, chlorine, $C_{1-4}$alkyl, $C_{1-4}$alkoxy-carbonyl, $C_{1-4}$alkyl-carbonyl, $C_{3-5}$cycloalkyl-carbonyl, di($C_{1-4}$alkyl)aminocarbonyl, $C_{1-4}$alkoxy, $C_{1-4}$alkylsulfonyl, $C_{1-4}$alkylsulfonyloxy, di($C_{1-4}$alkyl)amino, $C_{1-4}$haloalkoxy, $C_{1-4}$haloalkylthio, $C_{1-4}$haloalkylsulfinyl, $C_{1-4}$haloalkylsulfonyl, $C_{1-4}$haloalkyl-sulfonyloxy, formyl, carboxy, cyano, nitro or phenoxy,
$R^{1A}$ and $R^{2A}$ each independently represents hydrogen, chlorine, $C_{1-4}$alkyl, where at least one hydrogen of which may be optionally fluoro-substituted, $C_{3-5}$cycloalkyl, $C_{1-4}$alkoxy, $C_{1-4}$haloalkoxy or $C_{1-4}$alkylthio, $R^{3A}$ and $R^{4A}$ each independently represents hydrogen, fluorine, chlorine, $C_{1-4}$alkyl, $C_{1-4}$alkoxy, $C_{1-4}$alkylthio or $C_{1-4}$alkylsulfonyl, $R^{3A}$ represents hydroxy and $R^{4A}$ represents hydrogen or $C_{1-4}$alkyl, or $R^{3A}$ and $R^{4A}$ together may form C=O with the carbon atom to which they are bonded, $R^{6A}$ represents hydrogen or $C_{1-4}$alkyl, where at least one hydrogen of which may be optionally fluoro-substituted, with the exception of the following cases (T-1) or (T-3);

(T-1) the case in which $X^A$ represents $C_{1-4}$alkyl, and n represents 0, (T-3) the case in which $X^A$ represents fluorine or chlorine, n represents 0, $Z^A$ represents N, $R^{1A}$ and $R^{2A}$ represent methoxy, $R^{3A}$ and $R^{4A}$ represent hydrogen, $R^{3A}$ represents hydroxy and $R^{4A}$ represents hydrogen, or $R^{3A}$ and $R^{4A}$ together form C=O with the carbon atom to which they are bonded, and $R^{6A}$ represents hydrogen.

* * * * *